(12) United States Patent
Bonnert et al.

(10) Patent No.: US 8,436,178 B2
(45) Date of Patent: May 7, 2013

(54) IMIDAZOQUINOLINES WITH IMMUNO-MODULATING PROPERTIES

(75) Inventors: Roger Victor Bonnert, Leicestershire (GB); Thomas McInally, Leicestershire (GB); Stephen Thom, Leicestershire (GB); Hiroki Wada, Leicestershire (GB)

(73) Assignees: AstraZeneca AB, Sodertalje (SE); Dainippon Sumitomo Pharma Co., Ltd., Osaka (JP)

( * ) Notice: Subject to any disclaimer, the term of this patent is extended or adjusted under 35 U.S.C. 154(b) by 443 days.

(21) Appl. No.: 12/596,817

(22) PCT Filed: May 6, 2008

(86) PCT No.: PCT/GB2008/050328
§ 371 (c)(1),
(2), (4) Date: Apr. 30, 2010

(87) PCT Pub. No.: WO2008/135791
PCT Pub. Date: Nov. 13, 2008

(65) Prior Publication Data
US 2010/0280001 A1 Nov. 4, 2010

Related U.S. Application Data

(60) Provisional application No. 60/916,586, filed on May 8, 2007, provisional application No. 61/024,957, filed on Jan. 31, 2008.

(51) Int. Cl.
*C07D 471/02* (2006.01)
(52) U.S. Cl.
USPC .......................................................... 546/82
(58) Field of Classification Search ............... 546/82
See application file for complete search history.

(56) References Cited

U.S. PATENT DOCUMENTS

| | | | |
|---|---|---|---|
| 4,689,338 A | 8/1987 | Gerster | |
| 4,698,348 A | 10/1987 | Gerster | |
| 4,714,701 A | 12/1987 | Beauchamp | |
| 5,736,549 A | 4/1998 | Beasley et al. | |
| 5,994,361 A | 11/1999 | Penney et al. | |
| 6,028,076 A | 2/2000 | Hirota et al. | |
| 6,110,923 A | 8/2000 | Ely | |
| 6,329,381 B1 | 12/2001 | Kurimoto et al. | |
| 6,376,501 B1 | 4/2002 | Isobe et al. | |
| 6,448,236 B1 | 9/2002 | Monaghan | |
| 6,458,798 B1 | 10/2002 | Fujita et al. | |
| 6,541,485 B1 | 4/2003 | Crooks et al. | |
| 6,630,478 B2 | 10/2003 | Diamond et al. | |
| 6,887,880 B2 | 5/2005 | Levy et al. | |
| 6,951,866 B2 | 10/2005 | Fujita et al. | |
| 7,157,465 B2 | 1/2007 | Isobe et al. | |
| 7,521,454 B2 | 4/2009 | Isobe et al. | |
| 7,576,068 B2 | 8/2009 | Averett et al. | |
| 7,642,350 B2 | 1/2010 | Pryde | |
| 7,754,728 B2 | 7/2010 | Isobe et al. | |
| 8,012,964 B2 | 9/2011 | Kurimoto et al. | |
| 8,044,056 B2 | 10/2011 | Isobe et al. | |
| 8,063,051 B2 | 11/2011 | Bonnert et al. | |
| 8,067,411 B2 | 11/2011 | Bonnert et al. | |
| 8,067,413 B2 | 11/2011 | Bonnert et al. | |
| 8,138,172 B2 | 3/2012 | Cook et al. | |
| 2002/0040032 A1 | 4/2002 | Glasky et al. | |
| 2002/0128264 A1 | 9/2002 | Taylor | |
| 2003/0105323 A1 | 6/2003 | Fujita et al. | |
| 2003/0144283 A1 | 7/2003 | Coleman et al. | |
| 2003/0191086 A1 | 10/2003 | Hanus | |
| 2003/0212092 A1 | 11/2003 | Heppner et al. | |
| 2004/0019048 A1 | 1/2004 | Crooks et al. | |
| 2004/0132748 A1 | 7/2004 | Isobe et al. | |
| 2004/0204438 A1 | 10/2004 | Crooks et al. | |
| 2004/0229897 A1 | 11/2004 | Crooks et al. | |

(Continued)

FOREIGN PATENT DOCUMENTS

| | | |
|---|---|---|
| CA | 1220148 | 4/1987 |
| CN | 101239980 | 8/2008 |
| EP | 1035123 | 9/2000 |
| EP | 1541572 | 6/2005 |
| EP | 1550662 | 7/2005 |
| EP | 1728793 | 12/2006 |
| EP | 1908480 | 4/2008 |
| EP | 2138497 | 12/2009 |
| JP | 08-165292 | 6/1996 |
| JP | 347422/1997 | 11/1997 |

(Continued)

OTHER PUBLICATIONS

Venkatesh et al., J. Pharm. Sci. 89, 145-54 (2000) (p. 146, left column).*
Eiho et al. "Mechanism of long-lasting suppression against Th2 immune response in the lung by a novel antedrug TLR7 agonist," European Respiratory Society Annual Congress, Amsterdam, Sep. 24-28, 2011, Abstract and Poster.

(Continued)

*Primary Examiner* — Nizal Chandrakumar
(74) *Attorney, Agent, or Firm* — Morgan, Lewis & Bockius LLP

(57) ABSTRACT

The present invention provides compounds of formula (I)

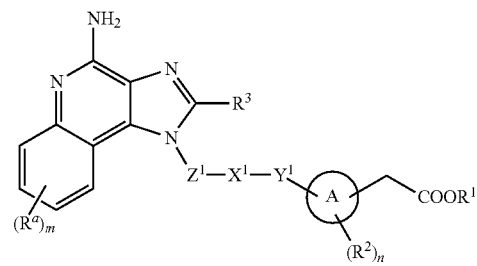

Figure 1B:
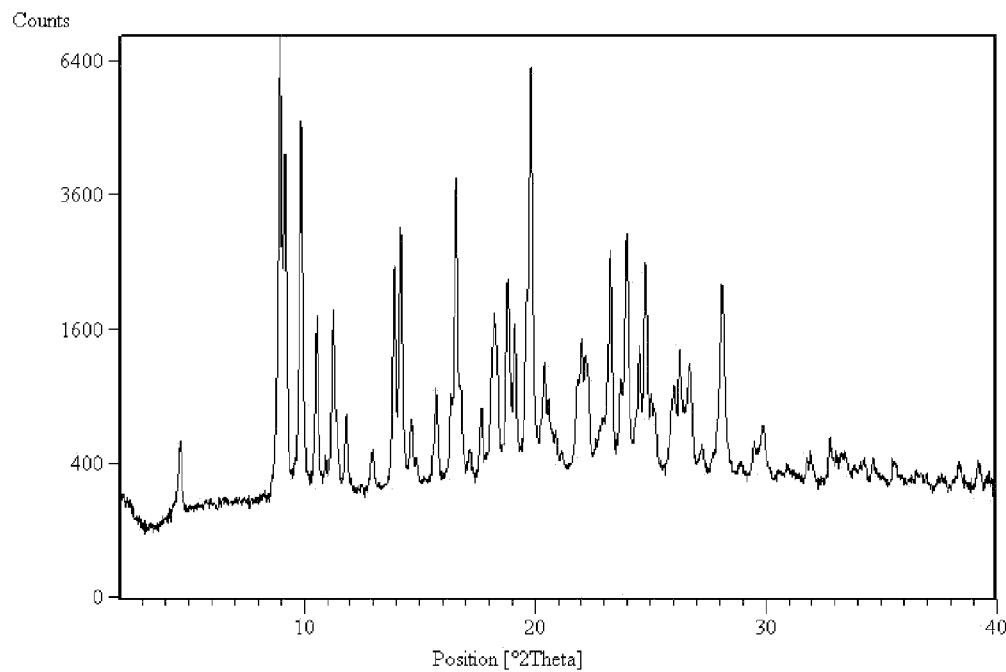

wherein $R^a$, $R^1$, $R^2$, $R^3$, $X^1$, $Y^1$, $Z^1$, A, n and m are as defined in the specification, and pharmaceutically acceptable salts thereof, as well as processes for their preparation, pharmaceutical compositions containing them and their use in therapy.

21 Claims, 9 Drawing Sheets

U.S. PATENT DOCUMENTS

| | | |
|---|---|---|
| 2005/0054590 A1 | 3/2005 | Averett |
| 2005/0119273 A1 | 6/2005 | Lipford et al. |
| 2006/0052403 A1 | 3/2006 | Isobe et al. |
| 2006/0252774 A1 | 11/2006 | Vatner et al. |
| 2007/0037832 A1 | 2/2007 | Isobe et al. |
| 2007/0190071 A1 | 8/2007 | Kurimoto et al. |
| 2007/0225303 A1 | 9/2007 | Ogita et al. |
| 2007/0249638 A1 | 10/2007 | Giorgio et al. |
| 2008/0008682 A1 | 1/2008 | Chong et al. |
| 2008/0269240 A1 | 10/2008 | Hashimoto et al. |
| 2008/0300244 A1 | 12/2008 | Bonnert et al. |
| 2009/0047249 A1 | 2/2009 | Graupe et al. |
| 2009/0082332 A1 | 3/2009 | Abbot et al. |
| 2009/0099216 A1 | 4/2009 | Millichip et al. |
| 2009/0105212 A1 | 4/2009 | Isobe et al. |
| 2009/0118263 A1 | 5/2009 | Hashimoto et al. |
| 2009/0131458 A1 | 5/2009 | Lazarides et al. |
| 2009/0143400 A1 | 6/2009 | McInally et al. |
| 2009/0192153 A1 | 7/2009 | Hashimoto et al. |
| 2009/0202484 A1 | 8/2009 | Chong et al. |
| 2009/0209524 A1 | 8/2009 | Bennett et al. |
| 2009/0281075 A1 | 11/2009 | Roughton et al. |
| 2009/0324551 A1 | 12/2009 | Carson et al. |
| 2009/0325877 A1 | 12/2009 | Grunt et al. |
| 2010/0075995 A1 | 3/2010 | Biggadike et al. |
| 2010/0087443 A1 | 4/2010 | Bonnert et al. |
| 2010/0093998 A1 | 4/2010 | Isobe et al. |
| 2010/0099870 A1 | 4/2010 | Isobe et al. |
| 2010/0120799 A1 | 5/2010 | Lazarides et al. |
| 2010/0130491 A1 | 5/2010 | Bonnert et al. |
| 2010/0240623 A1 | 9/2010 | Cook et al. |
| 2010/0298364 A1 | 11/2010 | Bennett et al. |
| 2011/0028715 A1 | 2/2011 | Isobe et al. |
| 2011/0046369 A1 | 2/2011 | Hashimoto et al. |
| 2011/0054168 A1 | 3/2011 | Kurimoto et al. |
| 2011/0136801 A1 | 6/2011 | Isobe et al. |
| 2011/0306610 A1 | 12/2011 | Kurimoto et al. |

FOREIGN PATENT DOCUMENTS

| | | |
|---|---|---|
| JP | 367449/1997 | 12/1997 |
| JP | 367451/1997 | 12/1997 |
| JP | 10-501533 | 2/1998 |
| JP | 11-180981 | 7/1999 |
| JP | 11-180982 | 7/1999 |
| JP | 11-193282 | 7/1999 |
| JP | 2000-159767 | 6/2000 |
| JP | 2004-137157 | 5/2004 |
| JP | 2005-089334 | 4/2005 |
| WO | WO 95/35297 | 12/1995 |
| WO | WO 96/11200 | 4/1996 |
| WO | WO 98/01448 | 1/1998 |
| WO | WO 99/28321 | 6/1999 |
| WO | WO 99/32122 | 7/1999 |
| WO | WO 00/12487 | 3/2000 |
| WO | WO 00/43394 | 7/2000 |
| WO | WO 00/76505 | 12/2000 |
| WO | WO 00/76519 | 12/2000 |
| WO | WO 01/27131 | 4/2001 |
| WO | WO 02/04449 | 1/2002 |
| WO | WO 02/04451 | 1/2002 |
| WO | WO 02/40481 | 5/2002 |
| WO | WO 02/46193 | 6/2002 |
| WO | WO 02/085905 | 10/2002 |
| WO | WO 03/011864 | 2/2003 |
| WO | WO 2004/011481 | 2/2004 |
| WO | WO 2004/029054 | 4/2004 |
| WO | WO 2004/075865 | 9/2004 |
| WO | WO 2004/087049 | 10/2004 |
| WO | WO 2005/025583 | 3/2005 |
| WO | WO 2005/092892 | 10/2005 |
| WO | WO 2005/092893 | 10/2005 |
| WO | WO 2006/029115 | 3/2006 |
| WO | WO 2006/091394 | 8/2006 |
| WO | WO 2006/129784 | 12/2006 |
| WO | WO 2007/024707 | 3/2007 |
| WO | WO 2007/031726 | 3/2007 |
| WO | WO 2007/034173 | 3/2007 |
| WO | WO 2007/034817 | 3/2007 |
| WO | WO 2007/034881 | 3/2007 |
| WO | WO 2007/034882 | 3/2007 |
| WO | WO 2007/034916 | 3/2007 |
| WO | WO 2007/034917 | 3/2007 |
| WO | WO 2008/004948 | 1/2008 |
| WO | WO 2008/005555 | 1/2008 |
| WO | WO 2008/071976 | 6/2008 |
| WO | WO 2008/101867 | 8/2008 |
| WO | WO 2008/114006 | 9/2008 |
| WO | WO 2008/114008 | 9/2008 |
| WO | WO 2008/114817 | 9/2008 |
| WO | WO 2008/114819 | 9/2008 |
| WO | WO 2009/005687 | 1/2009 |
| WO | WO 2009/062059 | 5/2009 |
| WO | WO 2009/067081 | 5/2009 |
| WO | WO 2009/078798 | 6/2009 |
| WO | WO 2009/091031 | 7/2009 |
| WO | WO 2009/091032 | 7/2009 |
| WO | WO 2009/151910 | 12/2009 |
| WO | WO 2010/018133 | 2/2010 |
| WO | WO 2010/033074 | 3/2010 |
| WO | WO 2010/133885 | 11/2010 |
| WO | WO 2011/068233 | 6/2011 |
| WO | WO 2012/011606 | 1/2012 |

OTHER PUBLICATIONS

Greiff et al. "Repeated intranasal TLR7 stimulation reduces allergen responsiveness in allergic rhinitis," European Respiratory Society Annual Congress, Amsterdam, Sep. 24-28, 2011, Abstract and Poster.

Biffen et al. "Novel TLR7 agonists for the treatment of allergic diseases," Toll 2011 Meeting, Riva del Garda, Italy, May 4-7, 2011, Abstract.

English translation of Opposition against Chilean Patent Application No. 1357-2008.

Chavarot et al. "Synthesis of an adenine-pyridinaldoxime-acridine conjugate for recognition of abasic site lesions in DNA" Tetrahedron 53(40): 13749-13756 (1997).

Drazen "Surgery for Emphysema—Not for Everyone" N. Engl. J. Med. 345(15): 1126-1128 (2001).

Dvorakova et al. "Synthesis of 2'-aminomethyl derivatives of N-(2-(phosphonomethoxyl)ethyl) nucleotide analogues as potential antiviral agents" Journal of Medicinal Chemistry 39(17): 3263-3268 (1996).

Fridkin "Vancomycin-intermediate and -resistant Staphylococcus aureus: what the infectious disease specialist needs to know" Clinical Infectious Diseases 32(1):108-115 (2001).

Hirota et al. "Discovery of 8-hydroxydenines as a novel type of interferon inducer" J. Med. Chem. 45(25):5419-5422 (2002).

Holy et al. "Studies on S-adenosyl-L-homocysteine hydrolase. XVI. 9-(Aminoalkyl)-8-hydroxyadenines: preparation mechanism of formation, and use in affinity chromatography of S-adenosyl-L-homocysteine hydrolase" Collection of Czechoslovak Chemical Communications 51(2): 459-477 (1986).

Isobe et al. "Synthesis and biological evaluation of novel 9-substituted-8-hydroxyadenine derivatives as potent interferon inducers" J. Med. Chem. 49(6):2088-2095 (2006).

Isobe et al. "Synthesis and structure-activity relationships of 2-substituted-8-hydroxyadenine derivatives as orally available interferon inducers without emetic side effects" Bioorganic & Medicinal Chemistry 11:3641-3647 (2003).

Itahara et al. "Control of liquid-crystalline properties by base pairing of adenine and thymine" ChemPhysChem 3(4): 378-379 (2002).

Korc "Pathways for aberrant angiogenesis in pancreatic cancer" Molecular Cancer 2(8):1-8 (2003).

Krueger et al. "Tilorone hydrochloride: an orally active antiviral agent" Science 169(3951):1213-1214 (1970).

Kurimoto et al. "Prodrugs of 9-benzyl-8-hydroxy-2-(2-hydroxyethylthio)adenine: Potent interferon inducing agents in monkeys" Chemical and Pharmaceutical Bulletin 52(4):466-469 (2004).

Kurimoto et al. "Synthesis and biological evaluation of novel 9-substituted-8-hydroxyadenine derivatives as potent interferon inducers" Journal of Medicinal Chemistry 49(6): 2088-2095 (2006).

Kurimoto et al. "Synthesis and evaluation of 2-substituted 8-hydroxyadenines as potent interferon inducers with improved oral bioavailabilities" Bioorganic & Medicinal Chemistry 12:1091-1099 (2004).

Kurimoto et al. "Synthesis and structure-activity relationships of 2-amino-8-hydroxyadenines as orally active interferon inducing agents" Bioorganic & Medicinal Chemistry 11:5501-5508 (2003).

Lee et al. "Activation of anti-hepatitis C virus responses via Toll-like receptor 7" Proc. Natl. Acad. Sci. USA 103(6): 1828-1833 (2006).

Lee et al. "Molecular basis for the immunostimulatory activity of guanine nucleoside analogs: Activation of Toll-like receptor 7" Proc. Natl. Acad. Sci. USA 100(11):6646-6651 (2003).

Mayer et al. "Tilorone hydrochloride: mode of action" Science 169(951): 1214-1215 (1970).

Mogulkoc et al. "Pulmonary function in idiopathic pulmonary fibrosis and referral for lung transplantation" Am J Respir Crit Care Med. 164(1):103-108 (2001).

Nichol et al. "Stimulation of murine interferon by a substituted pyrimidine" Antimicrobial Agents and Chemotherapy 9(3):433-439 (1976).

Palmer et al. "Highly drug-resistant HIV-1 clinical isolates are cross-resistant to many antiretroviral compounds in current clinical development" AIDS 13(6): 661-667 (1999).

Reiter et al. "Cytokine induction in mice by the immunomodulator imiquimod" Journal of Leukocyte Biology 55(2):234-240 (1994).

Spassova et al. "Synthesis of N-(3-azido-2-hydroxypropyl), N-(3-phthalimido-2-hydroxypropyl and N-(3-amino-2-hydroxypropyl) derivatives of heterocyclic bases" Collection of Czechoslovak chemical Communications 59(5): 1153-1174 (1994).

Stringfellow et al. "Antiviral and interferon-inducing properties of 1,5-diamino anthraquinones" Antimicrobial Agents and Chemotherapy 15(1):111-118 (1979).

Zalutsky "Targeted radiotherapy of brain tumours" British Journal of Cancer 90(8):1469-1473 (2004).

"Asthma" (MDAdvice.com) retrieved on Jun. 24, 2010 from the internet (URL:http://www.mdadvice.com/topics/asthma/info/1.htm).

"Chronic obstructive pulmonary disease"(AllRefer.com Health) retrieved on Jun. 24, 2010 from the internet (URL:http://health.allrefer.com/health/chronic-obstructive-pulmonary-disease-prevention.html).

"Respiratory experts call for global approach to treat chronic diseases" (Feb. 13, 2007) retrieved on Jun. 24, 2010 from the internet (URL: http://www.medwire-news.md/48/64443/Respiratory/Respiratory_experts_call_for_global_approach_to_treat_chronic_disease.html).

Aoki et al., "Weekly dosing of AZD8848/DSP-3025, A novel TLR7 agonist antedrug, demonstrates a prolonged period of control against markers of pulmonary inflammation in an alergen challenge model in the mouse" ATS International Conference, New Orleans, May 2010.

Bell et al., "AZD8848/DSP-3025, A novel potent TLR7 agonist antedrug, demonstrates negligible systemic activity and a prolonged period of control after cessation of weekly dosing in a brown norway rat ovalbumin challenge model" ATS International Conference, New Orleans, May 2010.

Biffen et al., "Biological activity of a novel TLR7 agonist antedrug for the treatment of allergic diseases," ATS International Conference, New Orleans, May 2010.

Ikeda et al., "AZD8848/DSP-3025, A novel potent TLR7 agonist antedrug, demonstrates efficacy against airway obstruction and other inflammatory endpoints in guinea pig models of rhinitis and asthma with acute and weekly dosing" ATS International Conference, New Orleans, May 2010.

Kurimoto et al. "Synthesis and biological evaluation of 8-oxoadenine derivatives as Toll-like Receptor 7 agonists introducing the antedrug concept" Journal of Medicinal Chemistry 53(7): 2964-2972 (2010).

Laino, "In small study, imaging detects lung damage in people exposed to secondhand smoke," Oncology Times, 30(2): 15 (Jan. 25, 2008).

Matsui et al., "Mechanisms of inhibition of type-2 cytokines by novel TLR7 agonist antedrugs," ATS International Conference, New Orleans, May 2010.

McInally "Identification and pharmacology of novel TLR7 agonist antedrugs," RSC BMSC Inflammation meeting, Nov. 18, 2010.

McInally et al., "Identification of a novel TLR7 agonist antedrug," EFMC-ISMC 2010, 21st International Symposium on Medicinal Chemistry, Brussels, Belgium, Sep. 5-9, 2010.

Tarkoy et al., "Nucleic-acid analogues with constraint conformational flexibility in the sugar-phosphate backbone ('Bicyclo-DNA')," Helvetica Chimica Acta, 76(1): 481-510 (1993).

Tojo et al., "Synthesis and biological evaluation of a novel TLR7 agonist with an antedrug strategy," EFMC-ISMC 2010, 21st International Symposium on Medicinal Chemistry, Brussels, Belgium, Sep. 5-9, 2010.

* cited by examiner

FIG.1A (MONOSACCHARIN SALT)

| XRPD of Monosaccharin salt of Example 75 | | | XRPD of Monosaccharin salt of Example 75 | | |
|---|---|---|---|---|---|
| 2Ø (°) | d space (Å) | Rel Int (%) | 2Ø (°) | d space (Å) | Rel Int (%) |
| 4.6027 | 19.1988 | 6.01 | 20.3882 | 4.35598 | 13.6 |
| 8.9098 | 9.92524 | 100 | 20.8927 | 4.25192 | 3.95 |
| 9.1314 | 9.6849 | 61.03 | 21.1494 | 4.20089 | 1.58 |
| 9.8454 | 8.98409 | 69.6 | 21.8231 | 4.07272 | 10.91 |
| 10.51 | 8.41743 | 21.3 | 21.9795 | 4.04409 | 17.47 |
| 11.2296 | 7.87957 | 22.53 | 22.2481 | 3.99586 | 12.85 |
| 11.7811 | 7.5119 | 6.96 | 23.2144 | 3.83168 | 35.37 |
| 12.9131 | 6.85585 | 3.57 | 23.6825 | 3.75699 | 10.81 |
| 13.8621 | 6.38856 | 31.7 | 23.9396 | 3.71722 | 39.35 |
| 14.1521 | 6.25829 | 41.66 | 24.4758 | 3.63698 | 14.01 |
| 14.5973 | 6.0684 | 5.88 | 24.74 | 3.59875 | 33.28 |
| 15.7051 | 5.64275 | 10.06 | 25.1925 | 3.53513 | 5.5 |
| 16.3208 | 5.43125 | 8.33 | 26.0071 | 3.42622 | 10.16 |
| 16.5399 | 5.35979 | 53.4 | 26.2171 | 3.39924 | 16.71 |
| 17.133 | 5.17556 | 2.08 | 26.6578 | 3.34404 | 14.3 |
| 17.6229 | 5.03276 | 7.27 | 27.1841 | 3.28049 | 2.35 |
| 18.2299 | 4.86653 | 21.53 | 28.0794 | 3.17789 | 30.19 |
| 18.7762 | 4.72618 | 30.22 | 28.9366 | 3.08566 | 1.08 |
| 19.0702 | 4.65395 | 20.18 | 29.4677 | 3.03125 | 3.24 |
| 19.789 | 4.48651 | 91.01 | 29.8812 | 2.99024 | 5.24 |
| | | | Accuracy - +/- 0.1° 2Ø | | |

FIG. 2A (DISACCHARIN SALT)

| XRPD of Disaccharin salt of Example 76 | | | XRPD of Disaccharin salt of Example 76 | | |
|---|---|---|---|---|---|
| 2Ø (°) | d space (Å) | Rel Int (%) | 2Ø (°) | d space (Å) | Rel Int (%) |
| 5.3416 | 16.54474 | 21.48 | 20.48 | 4.33667 | 11.62 |
| 6.5352 | 13.52536 | 100 | 20.926 | 4.24524 | 18.81 |
| 7.7301 | 11.43711 | 43.63 | 21.3066 | 4.17025 | 70.99 |
| 10.5656 | 8.37323 | 15.03 | 22.0152 | 4.0376 | 23.34 |
| 11.0105 | 8.03589 | 34.62 | 22.2192 | 4.00099 | 36.23 |
| 11.571 | 7.64786 | 85.25 | 22.9506 | 3.87512 | 46.28 |
| 13.4171 | 6.59942 | 46.07 | 23.3028 | 3.81733 | 82.34 |
| 13.9647 | 6.34183 | 9.55 | 23.6699 | 3.75896 | 36.71 |
| 14.5655 | 6.08159 | 6.09 | 23.8781 | 3.72665 | 30.13 |
| 14.9236 | 5.93645 | 8.99 | 24.1747 | 3.68161 | 44.6 |
| 15.4756 | 5.72591 | 22.74 | 24.9916 | 3.56308 | 12.8 |
| 16.0299 | 5.52916 | 16.13 | 25.1745 | 3.53761 | 8.4 |
| 16.299 | 5.43845 | 4.99 | 25.4647 | 3.49794 | 7.32 |
| 16.9477 | 5.23174 | 18.92 | 26.2197 | 3.39891 | 13.45 |
| 17.5357 | 5.0576 | 11.45 | 26.7323 | 3.33489 | 11.63 |
| 18.16 | 4.88512 | 58.41 | 27.255 | 3.27211 | 8.88 |
| 18.4462 | 4.80996 | 43.87 | 27.8797 | 3.20019 | 14.91 |
| 18.9933 | 4.67264 | 19.42 | 28.4616 | 3.13608 | 14.13 |
| 19.2675 | 4.60674 | 58.35 | 29.0496 | 3.07392 | 9.74 |
| 19.6257 | 4.52347 | 50.09 | 29.2983 | 3.0484 | 20.85 |
| 19.9548 | 4.4496 | 28.78 | 29.9366 | 2.98483 | 11.57 |
| 20.0562 | 4.42733 | 21.3 | Accuracy - +/- 0.1° 2Ø | | |

FIG. 3A (DI-1-HYDROXY-2-NAPHTHOIC ACID SALT – POLYMORPH A)

| XRPD of Di-1-hydroxy-2-naphthoic acid salt of Example 77 (Polymorph A) | | |
|---|---|---|
| 2Ø (°) | d space (Å) | Rel Int (%) |
| 4.7239 | 18.70671 | 100 |
| 5.7221 | 15.44541 | 9.69 |
| 6.1232 | 14.43435 | 9.1 |
| 7.653 | 11.55211 | 12.26 |
| 9.4531 | 9.35595 | 23.08 |
| 12.5007 | 7.08107 | 5.48 |
| 16.3724 | 5.41425 | 9.76 |
| 18.318 | 4.84334 | 10.66 |
| 18.9742 | 4.67728 | 6.75 |
| 21.225 | 4.1861 | 8.39 |
| 21.8629 | 4.06539 | 9.02 |
| 24.521 | 3.63038 | 8.04 |
| Accuracy - +/- 0.1° 2Ø | | |

FIG. 3C (DI-1-HYDROXY-2-NAPHTHOIC ACID SALT – POLYMORPH B)

| XRPD of Di-1-hydroxy-2-naphthoic acid salt of Example 77 (Polymorph B) | | | XRPD of Di-1-hydroxy-2-naphthoic acid salt of Example 77 (Polymorph B) | | |
|---|---|---|---|---|---|
| 2Ø (°) | d space (Å) | Rel Int (%) | 2Ø (°) | d space (Å) | Rel Int (%) |
| 4.8063 | 18.38615 | 38.26 | 19.8613 | 4.47034 | 9.24 |
| 5.81 | 15.21174 | 100 | 20.2118 | 4.3936 | 15.96 |
| 9.5943 | 9.21866 | 9.9 | 21.2346 | 4.18424 | 17.11 |
| 10.1504 | 8.71481 | 5.65 | 21.7365 | 4.08874 | 29.77 |
| 11.0872 | 7.98043 | 3.35 | 22.2304 | 3.999 | 7.14 |
| 12.4293 | 7.12159 | 21.53 | 22.4306 | 3.96375 | 9.3 |
| 13.0432 | 6.78776 | 3.79 | 23.0259 | 3.86261 | 9.53 |
| 13.9071 | 6.36798 | 12.1 | 23.8564 | 3.73 | 23.52 |
| 14.7768 | 5.9951 | 38.98 | 24.3758 | 3.65167 | 3.77 |
| 16.125 | 5.49676 | 13.36 | 25.2656 | 3.52506 | 6.94 |
| 16.6667 | 5.3193 | 58.72 | 26.7118 | 3.3374 | 8.59 |
| 18.4539 | 4.80797 | 19.13 | 27.0973 | 3.29079 | 10.21 |
| 18.7766 | 4.72606 | 20.04 | 27.3424 | 3.26185 | 9.6 |
| 19.4876 | 4.55521 | 31.07 | 27.8233 | 3.20656 | 7.54 |
| | | | Accuracy - +/- 0.1° 2Ø | | |

FIG. 4A (DIBENZENE SULPHONIC ACID SALT)

| XRPD of Dibenzene sulphonic acid salt of Example 78 | | | XRPD of Dibenzene sulphonic acid salt of Example 78 | | |
|---|---|---|---|---|---|
| 2Ø (°) | d space (Å) | Rel Int (%) | 2Ø (°) | d space (Å) | Rel Int (%) |
| 5.6755 | 15.57211 | 100 | 19.8994 | 4.46187 | 9.18 |
| 6.1143 | 14.45531 | 2.78 | 20.3201 | 4.37043 | 13.55 |
| 8.1512 | 10.84715 | 1.03 | 20.4911 | 4.33433 | 10.69 |
| 10.9335 | 8.09227 | 10.56 | 20.9469 | 4.24106 | 13.56 |
| 11.4099 | 7.75545 | 1.11 | 21.8147 | 4.07426 | 3.88 |
| 12.2121 | 7.24774 | 3.93 | 22.7755 | 3.90452 | 7.12 |
| 13.1924 | 6.71132 | 7.94 | 23.348 | 3.81006 | 12.08 |
| 14.1561 | 6.25652 | 15.76 | 23.6102 | 3.76833 | 4.41 |
| 14.6713 | 6.03797 | 8.69 | 23.8936 | 3.72427 | 12.9 |
| 14.93 | 5.9339 | 10.83 | 24.4017 | 3.64786 | 12.84 |
| 15.2689 | 5.80297 | 3.81 | 25.3118 | 3.51872 | 5.14 |
| 16.4498 | 5.38894 | 14.64 | 25.55 | 3.48647 | 5.79 |
| 17.269 | 5.13511 | 3.79 | 26.1539 | 3.40731 | 2.14 |
| 17.8509 | 4.969 | 38.94 | 26.6509 | 3.34489 | 6.63 |
| 19.089 | 4.64943 | 13.52 | 28.6269 | 3.11834 | 2.36 |
| 19.363 | 4.58424 | 11.11 | Accuracy - +/- 0.1° 2Ø | | |

FIG. 5A (MANDELIC ACID SALT)

| XRPD of Mandelic acid salt of Example 79 ||| XRPD of Mandelic acid salt of Example 79 |||
|---|---|---|---|---|---|
| 2Ø (°) | d space (Å) | Rel Int (%) | 2Ø (°) | d space (Å) | Rel Int (%) |
| 5.1472 | 17.16896 | 82.35 | 19.7845 | 4.48752 | 23.07 |
| 8.3078 | 10.64308 | 4.02 | 20.231 | 4.38947 | 13.36 |
| 9.0958 | 9.72265 | 100 | 20.7878 | 4.27315 | 15.53 |
| 10.2997 | 8.5888 | 43.04 | 21.1786 | 4.19517 | 98.07 |
| 10.4217 | 8.48848 | 42.71 | 21.6432 | 4.10615 | 22.36 |
| 10.6849 | 8.27997 | 15.5 | 22.0976 | 4.02274 | 3.5 |
| 11.2539 | 7.86259 | 9.93 | 22.5339 | 3.94582 | 18.75 |
| 12.1939 | 7.25851 | 20.59 | 24.3326 | 3.65807 | 30.11 |
| 13.1727 | 6.72132 | 11.23 | 25.088 | 3.54962 | 10.15 |
| 14.3686 | 6.16447 | 7 | 25.4463 | 3.50043 | 10.77 |
| 14.812 | 5.98093 | 24.74 | 26.0294 | 3.42332 | 5.7 |
| 15.0598 | 5.88307 | 25.97 | 26.4733 | 3.36692 | 6.81 |
| 16.0857 | 5.51009 | 7.15 | 26.9757 | 3.30535 | 4.06 |
| 16.4839 | 5.37788 | 21.39 | 27.7609 | 3.21362 | 5.14 |
| 16.9482 | 5.23156 | 3.28 | 28.4138 | 3.14124 | 15.98 |
| 17.6773 | 5.01741 | 35.25 | 30.0483 | 2.97399 | 17.11 |
| 18.0478 | 4.91525 | 43.63 | 33.8863 | 2.64543 | 8.75 |
| 18.2801 | 4.8533 | 19.43 | 34.5222 | 2.59814 | 4.49 |
| 18.8177 | 4.71584 | 9.01 | 36.1464 | 2.48504 | 3.43 |
| 19.5288 | 4.54568 | 19.82 | Accuracy - +/- 0.1° 2Ø |||

FIG. 6A (FUMARIC ACID SALT)

| XRPD of Fumaric acid salt of Example 80 | | | XRPD of Fumaric acid salt of Example 80 | | |
|---|---|---|---|---|---|
| 2Ø (°) | d space (Å) | Rel Int (%) | 2Ø (°) | d space (Å) | Rel Int (%) |
| 3.7157 | 23.77979 | 85.21 | 19.1644 | 4.6313 | 11.9 |
| 7.424 | 11.90803 | 7.02 | 20.163 | 4.40412 | 100 |
| 9.102 | 9.71612 | 45.78 | 20.8172 | 4.26718 | 80.16 |
| 9.3738 | 9.43499 | 21.69 | 21.9414 | 4.05101 | 18.46 |
| 10.2967 | 8.5913 | 43.78 | 22.5111 | 3.94977 | 26.14 |
| 10.975 | 8.06179 | 72.65 | 22.7739 | 3.90478 | 67.34 |
| 11.1962 | 7.90301 | 40.65 | 23.3279 | 3.81329 | 30.59 |
| 13.4704 | 6.57342 | 20.7 | 23.5443 | 3.77873 | 24.66 |
| 13.7631 | 6.43426 | 32.21 | 23.9771 | 3.71148 | 11.39 |
| 14.2837 | 6.20091 | 17.35 | 25.4314 | 3.50245 | 24.21 |
| 14.9399 | 5.93001 | 23.83 | 25.7829 | 3.45549 | 60.28 |
| 15.3787 | 5.76179 | 13.93 | 26.3371 | 3.38403 | 25.4 |
| 16.4489 | 5.38924 | 26.02 | 26.6728 | 3.34219 | 62.3 |
| 16.7137 | 5.30444 | 23.84 | 27.3812 | 3.25732 | 12.4 |
| 17.1441 | 5.17223 | 8.56 | 27.9344 | 3.19405 | 12.42 |
| 17.621 | 5.03332 | 18.29 | 28.4154 | 3.14107 | 24.11 |
| 18.2853 | 4.85193 | 31.96 | 29.4614 | 3.03189 | 7.74 |
| 18.5334 | 4.78753 | 48.57 | 31.1867 | 2.86798 | 13.57 |
| | | | Accuracy - +/- 0.1° 2Ø | | |

FIG. 7A (DIMETHANE SULPHONIC ACID SALT – POLYMORPH A)

| XRPD of Dimethane sulphonic acid salt of Example 81 (Polymorph A) | | | XRPD of Dimethane sulphonic acid salt of Example 81 (Polymorph A) | | |
|---|---|---|---|---|---|
| 2Ø (°) | d space (Å) | Rel Int (%) | 2Ø (°) | d space (Å) | Rel Int (%) |
| 6.0786 | 14.54035 | 100 | 20.0707 | 4.42416 | 19.16 |
| 6.6961 | 13.20073 | 9.25 | 22.0066 | 4.03917 | 4.02 |
| 10.991 | 8.05011 | 9.91 | 22.3345 | 3.9806 | 5.84 |
| 12.131 | 7.29603 | 2.01 | 22.7703 | 3.9054 | 19.61 |
| 13.3765 | 6.61935 | 2.12 | 23.0254 | 3.8627 | 25.61 |
| 15.1162 | 5.86122 | 30.96 | 23.5954 | 3.77065 | 6.24 |
| 15.4675 | 5.7289 | 5.32 | 24.3304 | 3.6584 | 14.24 |
| 16.9466 | 5.23206 | 3.87 | 24.7877 | 3.59193 | 3.93 |
| 17.2331 | 5.14573 | 3.05 | 26.1279 | 3.41064 | 13.3 |
| 17.549 | 5.0538 | 5.61 | 27.081 | 3.29273 | 5.34 |
| 18.2229 | 4.86841 | 23.14 | 29.3297 | 3.0452 | 2.22 |
| 18.812 | 4.71726 | 4.83 | 30.4685 | 2.93393 | 3 |
| 19.1892 | 4.62538 | 5.23 | 31.225 | 2.86455 | 3.12 |
| 19.7243 | 4.50107 | 7.43 | Accuracy - +/- 0.1° 2Ø | | |

FIG. 7C (DIMETHANE SULPHONIC ACID SALT – POLYMORPH B)

| XRPD of Dimethane sulphonic acid salt of Example 81 (Polymorph B) | | |
|---|---|---|
| 2Ø (°) | d space (Å) | Rel Int (%) |
| 6.0724 | 14.55513 | 100 |
| 6.4958 | 13.60735 | 9.48 |
| 7.9999 | 11.05193 | 3 |
| 10.9579 | 8.07434 | 16.28 |
| 13.1171 | 6.74968 | 3.74 |
| 14.4262 | 6.13997 | 19.86 |
| 16.5482 | 5.35713 | 2.46 |
| 17.7999 | 4.98312 | 10.33 |
| 19.54 | 4.54312 | 21.14 |
| 21.3672 | 4.15856 | 6.24 |
| Accuracy - +/- 0.1° 2Ø | | |

IMIDAZOQUINOLINES WITH IMMUNO-MODULATING PROPERTIES

RELATED APPLICATIONS

The present application is a U.S. National Phase Application of International Application No. PCT/GB2008/050328, filed May 6, 2008, which claims the benefit of U.S. Provisional Patent Application No. 60/916,586, filed May 8, 2007, and U.S. Provisional Patent Application No. 61/024,957, filed Jan. 31, 2008, all of which are hereby incorporated by reference in their entirety.

NAMES OF PARTIES TO A JOINT RESEARCH AGREEMENT

The subject matter claimed in this application was made as a result of activities undertaken within the scope of a joint research agreement dated Dec. 19, 2003, between AstraZeneca AB and Sumitomo Pharmaceuticals Co., Ltd. All of the rights and obligations of Sumitomo Pharmaceuticals Co., Ltd. as defined in the joint research agreement between AstraZeneca AB and Sumitomo Pharmaceuticals Co., Ltd. were assumed by Dainippon Sumitomo Pharma Co., Ltd., a company created by the merger of Dainippon Pharmaceuticals Co., Ltd. and Sumitomo Pharmaceuticals Co., Ltd. effective Oct. 3, 2005.

The present invention relates to imidazoquinoline derivatives, processes for their preparation, pharmaceutical compositions containing them and their use in therapy.

The immune system is comprised of innate and acquired immunity, both of which work cooperatively to protect the host from microbial infections. It has been shown that innate immunity can recognize conserved pathogen-associated molecular patterns through toll-like receptors (TLRs) expressed on the cell surface of immune cells. Recognition of invading pathogens then triggers cytokine production (including interferon alpha(IFNα)) and upregulation of co-stimulatory molecules on phagocytes, leading to modulation of T cell function. Thus, innate immunity is closely linked to acquired immunity and can influence the development and regulation of an acquired response.

TLRs are a family of type I transmembrane receptors characterized by an $NH_2$-terminal extracellular leucine-rich repeat domain (LRR) and a COOH-terminal intracellular tail containing a conserved region called the Toll/IL-1 receptor (TIR) homology domain. The extracellular domain contains a varying number of LRR, which are thought to be involved in ligand binding. Eleven TLRs have been described to date in humans and mice. They differ from each other in ligand specificities, expression patterns, and in the target genes they can induce.

Ligands which act via TLRs (also known as immune response modifiers (IRMS)) have been developed, for example, the imidazoquinoline derivatives described in U.S. Pat. No. 4,689,338 which include the product Imiquimod for treating genital warts, and the adenine derivatives described in WO 98/01448 and WO 99/28321.

This patent application describes a class of imidazoquinoline compounds having immuno-modulating properties which act via TLR7 that are useful in the treatment of viral or allergic diseases and cancers.

In accordance with the present invention, there is therefore provided a compound of formula (I)

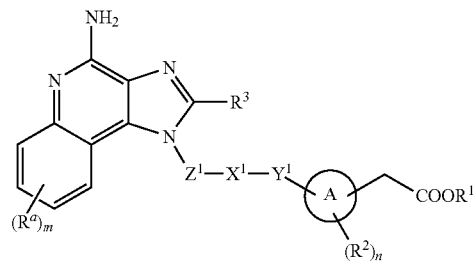

wherein
$R^1$ represents a straight chain $C_1$-$C_6$ alkyl, optionally substituted by one or more substituents independently selected from halogen, cyano, hydroxyl and $C_1$-$C_3$ alkoxy;
$Z^1$ represents a $C_2$-$C_6$ alkylene or $C_3$-$C_8$ cycloalkylene group;
$X^1$ represents $NR^5$, >N—$COR^5$, $CONR^5$, $NR^5CO$, $SO_2NR^5$, >N—$SO_2R^5$, $NR^5SO_2$, $NR^5CONR^6$ or $NR^6CONR^5$, $S(O)_p$ or O;
$Y^1$ represents a single bond or $C_1$-$C_6$ alkylene;
each $R^2$ is independently selected from halogen, cyano, hydroxy, thiol, $C_1$-$C_3$ alkyl, $C_1$-$C_3$ hydroxyalkyl, $C_1$-$C_3$ haloalkyl, $C_1$-$C_3$ alkoxy, $C_1$-$C_3$ haloalkoxy, $C_{1-3}$alkylthio, $C_{1-3}$alkylsulfonyl and $C_{1-3}$alkylsulfinyl;
$R^3$ represents $C_{1-6}$alkyl optionally substituted by $C_{1-6}$alkoxy;
each $R^a$ is independently selected from halogen, cyano, hydroxy, thiol, $C_1$-$C_3$ alkyl, $C_1$-$C_3$ hydroxyalkyl, $C_1$-$C_3$ haloalkyl, $C_1$-$C_3$ alkoxy, $C_1$-$C_3$ haloalkoxy, $C_{1-3}$alkylthio, $C_{1-3}$alkylsulfonyl and $C_{1-3}$alkylsulfinyl;
$R^5$ represents hydrogen, a 3- to 8-membered saturated heterocyclic ring comprising a ring group O, $S(O)_p$ or $NR^{10}$, a $C_1$-$C_6$ alkyl group or $C_3$-$C_6$ cycloalkyl group, the latter two groups being optionally substituted by one or more substituents independently selected from $NR^7R^8$ or $R^9$,
or $R^5$ is a $C_1$-$C_6$ alkylene which may be linked to a carbon atom within a $C_2$-$C_6$alkylene group $Z^1$ so as to form a saturated 4-7 membered nitrogen containing ring;
provided that when $X^1$ is >N—$SO_2R^5$, $R^5$ does not represent hydrogen;
$R^7$ and $R^8$ each independently represent hydrogen, a 3- to 8-membered saturated heterocyclic ring comprising a ring group O, $S(O)_p$ or $NR^{10a}$, $C_1$-$C_6$ alkyl or $C_3$-$C_6$ cycloalkyl, the latter two groups being optionally substituted by one or more groups independently selected from halogen, cyano, $S(O)_qR^{11}$, $OR^{12}$, $CO_2R^{12}$, $OC(O)R^{12}$, $SO_2NR^{12}R^{13}$, $CONR^{12}R^{13}$, $NR^{12}R^{13}$, $NR^{12}SO_2R^{14}$, $NR^{12}COR^{13}$, or a 3- to 8-membered saturated heterocyclic ring comprising a ring group O, $S(O)_p$ or $NR^{10b}$,
or $R^7$ and $R^8$ together with the nitrogen atom to which they are attached form a 3- to 8-membered saturated heterocyclic ring comprising a ring nitrogen atom and optionally one or more further heteroatoms independently selected from nitrogen, oxygen, sulphur and sulphonyl, the heterocyclic ring being optionally substituted by one or more substituents independently selected from halogen, cyano, $S(O)_qR^{15}$, $OR^{15}$, $CO_2R^{15}$, $COR^{15}$, $OC(O)R^{15}$, $SO_2NR^{15}R^{16}$, $CONR^{15}R^{16}$, $NR^{15}R^{16}$, $NR^{15}SO_2R^{17}$, $NR^{15}COR^{16}$, $NR^{15}CO_2R^{16}$, heteroaryl, $C_1$-$C_6$ haloalkyl, $C_3$-$C_8$ cycloalkyl and $C_1$-$C_6$ alkyl, the latter two groups being optionally substituted by one or more groups independently selected from cyano, $S(O)_qR^{18}$, $OR^{18}$, $CO_2R^{18}$, $SO_2NR^{18}R^{19}$, $CONR^{18}R^{19}$ or $NR^{18}R^{19}$;

$R^9$ represents halogen, cyano, $CO_2R^{20}$, $S(O)_qR^{20}$, $OR^{20}$, $SO_2NR^{20}R^{22}$, $CONR^{20}R^{22}$, $NR^{20}SO_2R^{21}$, $NR^{20}CO_2R^{21}$, $NR^{20}COR^{22}$ or a 3- to 8-membered saturated heterocyclic ring comprising a ring group $NR^{10c}$;

$R^{10}$, $R^{10a}$, $R^{10b}$ and $R^{10c}$ independently represent hydrogen, $CO_2R^{23}$, $S(O)_qR^{23}$, $COR^{24}$, or a $C_1$-$C_6$ alkyl, $C_2$-$C_6$ alkenyl, $C_2$-$C_6$ alkynyl or $C_3$-$C_8$ cycloalkyl group, each of which may be optionally substituted by one or more substituents independently selected from halogen, cyano, $OR^{25}$ or $NR^{25}R^{26}$;

$R^6$, $R^{11}$, $R^{12}$, $R^{13}$, $R^{15}$, $R^{16}$, $R^{18}$, $R^{19}$, $R^{20}$, $R^{22}$, $R^{24}$, $R^{25}$ and $R^{26}$ each independently represent hydrogen, $C_1$-$C_6$ alkyl or $C_3$-$C_6$ cycloalkyl;

$R^{14}$, $R^{17}$, $R^{20}$ and $R^{23}$ each independently represent $C_1$-$C_6$ alkyl or $C_3$-$C_6$ cycloalkyl;

m, n, p and q each independently represent an integer 0, 1 or 2; and

A represents a monocyclic or bicyclic $C_6$-$C_{10}$ aryl or a monocyclic or bicyclic $C_5$-$C_{12}$ heteroaryl group containing 1-3 heteroatoms;

or a pharmaceutically acceptable salt thereof.

In the context of the present specification, unless otherwise stated, an alkyl substituent group or an alkyl moiety in a substituent group may be linear or branched. They may for example contain from 1 to 6 carbon atoms. Examples of $C_1$-$C_6$ alkyl groups/moieties include methyl, ethyl, n-propyl, isopropyl, n-butyl, isobutyl, tert-butyl, n-pentyl and n-hexyl. Similarly, an alkylene group/moiety may be linear or branched. Examples of $C_1$-$C_6$ alkylene groups/moieties include methylene, ethylene, n-propylene, n-butylene, n-pentylene, n-hexylene, 1-methylethylene, 2-methylethylene, 1,2-dimethylethylene, 1-ethylethylene, 2-ethylethylene, 1-, 2- or 3-methylpropylene and 1-, 2- or 3-ethylpropylene. An alkenyl or alkynyl group is an unsaturated linear or branched group, containing for example from 2 to 6 carbon atoms. It should be appreciated that, in formula (I), if more than one substituent contains a group or moiety $S(O)_p$ or $S(O)_q$ or if a substituent contains two or more $S(O)_p$ or $S(O)_q$, then each "p" or each "q" independently represents an integer 0, 1 or 2. For example, if $R^7$ represents a $C_3$-$C_6$ cycloalkyl group substituted by two groups $S(O)_qR^{11}$, then each "q" may be the same or different. In the same way, each group "$R^{11}$", where there is more than one such group, may be the same or different.

Cycloalkyl or carbocycle groups are rings containing, for example, from 3 to 8 carbon atoms and are saturated.

Heterocyclic groups are rings which may be saturated, partially unsaturated or unsaturated, and contain from 3 to 20 atoms, at least one and suitably from 1 to 4 atoms are heteroatoms selected from oxygen, sulphur and nitrogen. Rings may be monocyclic, fused, bridged, or spiro bicyclic heterocyclic ring system(s). Monocyclic heterocyclic rings contain from about 3 to 12 ring atoms, with from 1 to 5 heteroatoms selected from N, O, and S, and suitably from 3 to 7 member atoms, in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems.

Examples of heterocyclic groups which are saturated or partially saturated include cyclic ethers (oxiranes) such as ethyleneoxide, tetrahydrofuran, dioxane, and substituted cyclic ethers. Heterocycles containing nitrogen include, for example, azetidine, pyrrolidine, piperidine, piperazine, tetrahydrotriazine, tetrahydropyrazole, and the like. Typical sulfur containing heterocycles include tetrahydrothiophene, dihydro-1,3-dithiol-2-yl, and hexahydrothiepin-4-yl. Other heterocycles include dihydro-oxathiol-4-yl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothiophene. A suitable value for a heterocyclyl group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

Heterocyclic groups which are aromatic in nature are referred to as "heteroaryl" groups. These groups are aromatic mono-, bi-, or polycyclic heterocyclic ring incorporating one or more (for example 1-4) heteroatoms selected from N, O, and S. The term heteroaryl includes both monovalent species and divalent species. Examples of heteroaryl groups include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers ring systems wherein at least one ring is an aromatic ring containing 1 or more heteroatoms selected from O, S and N and one or more of the other rings is a non-aromatic, saturated or partially unsaturated ring optionally containing one or more heteroatoms selected from O, S and N, for example 1,2,3,4-tetrahydro-1, 8-naphthyridinyl, 1,2,3,4-tetrahydropyrido[2,3-b]pyrazinyl and 3,4-dihydro-2H-pyrido[3,2-b][1,4]oxazinyl.

A preferred heteroaryl group is a 5-7 member aromatic ring or 6,6- or 6,5-fused bicyclic ring containing one or more ring heteroatoms selected from N, S, O. Examples include pyridine, pyrimidine, thiazole, oxazole, pyrazole, imidazole, furan, isoxazole, pyrrole, isothiazole and azulene, naphthyl, indene, quinoline, isoquinoline, indole, indolizine, benzo[b]furan, benzo[b]thiophene, 1H-indazole, benzimidazole, benzthiazole, benzoxazole, purine, 4H-quinolizine, cinnoline, phthalazine, quinazoline, quinoxaline, 1,8-naphthyridine, pteridine and quinolone.

Preferably $R^1$ represents a straight chain $C_{1-6}$alkyl group optionally substituted by $C_{1-3}$alkoxy, for example, methyl, ethyl, n-propyl, n-butyl, methoxymethyl or methoxyethyl. In a particular embodiment $R^1$ is methyl.

In a particular embodiment. $Z^1$ is a $C_{2-6}$alkylene, in particular a straight chain $C_{2-6}$alkylene group, for example a straight chain $C_{2-4}$alkylene group. A particular example of $Z^1$ is n-propylene.

In a particular embodiment, $X^1$ represents $NR^5$, $>N—COR^5$, $NR^5CO$, $NR^5SO_2$ or $>N—SO_2R^5$. (For the avoidance of doubt, within the definition of $X^1$, the first atom appearing is linked to the $Z^1$ group. Thus, when $X^1$ is $SO_2NR^5$, the sulphur atom is linked to the $Z^1$ group and the nitrogen atom is linked to the $Y^1$ group.)

In another embodiment, $X^1$ represents $NR^5$ or >N—$COR^5$.

Where $R^6$ is present in any group $X^1$, it is suitably selected from hydrogen or $C_{1-6}$alkyl such as methyl.

A particular example of $X^1$ is a group $NR^5$.

Another particular example of an $X^1$ group is >N—$COR^5$.

Particular examples of $R^5$ groups include hydrogen or a $C_{1-6}$alkyl optionally substituted by one or more substituents independently selected from $NR^7R^8$ or $R^9$, where $R^7$, $R^8$ and $R^9$ are as defined above.

For instance, $R^5$ represents a $C_1$-$C_6$ alkyl or $C_1$-$C_4$ alkyl optionally substituted by one or more substituents independently selected from $NR^7R^8$ or $R^9$, where $R^7$, $R^8$ and $R^9$ are as defined above.

In particular, $R^5$ is a $C_1$-$C_6$ alkyl, particularly $C_1$-$C_3$ alkyl such as methyl, ethyl or n-propyl, optionally substituted by one or more substituents independently selected from $NR^7R^8$ where $R^7$ and $R^8$ are as defined above.

In yet a further embodiment, $R^5$ is a $C_1$-$C_6$ alkylene which may be linked to a carbon atom within a $C_2$-$C_6$ alkylene group $Z^1$ so as to form a saturated 4-7 membered nitrogen containing ring. In particular, $R^5$ is linked to a carbon atom in the $Z^1$ chain so as to form for example, where $X^1$ is a group $NR^5$, a piperidine ring.

In a particular embodiment, $Y^1$ represents $C_1$-$C_6$ alkylene, such as a $CH_2$ group.

In a further embodiment, where A is a heteroaryl group, it is suitably a monocyclic ring containing six atoms, one or two of which are nitrogen. Thus particular examples of heteroaryl groups A include pyridyl and pyrimidinyl, suitably pyridyl.

A particular example of ring A is phenyl.

Where present, $R^2$ is suitably halogen such as fluoro or chloro, cyano, hydroxy, thiol, $C_1$-$C_3$ alkyl such as methyl, $C_1$-$C_3$ hydroxyalkyl such as hydroxymethyl, $C_1$-$C_3$ haloalkyl such as trifluoromethyl, $C_1$-$C_3$ alkoxy such as methoxy or ethoxy, $C_1$-$C_3$ haloalkoxy such as trifluoromethoxy, $C_{1-3}$alkylthio such as methylthio, $C_{1-3}$alkylsulfonyl such as methylsulfonyl or $C_{1-3}$alkylsulfinyl such as methylsulfinyl.

Preferably however, n is 0.

In a particular embodiment, $R^3$ represents a $C_{1-6}$alkyl group optionally substituted by a $C_{1-4}$alkoxy group. Examples of alkyl groups include methyl, ethyl, iso-propyl, n-propyl, and n-butyl. A particular example of $R^3$ is n-butyl. Particular examples of an alkoxy substituted alkyl group $R^3$ are ethoxymethyl and methoxyethyl.

Where present, each $R^a$ suitably independently represents halogen such as chloro or fluoro, cyano, hydroxy, thiol, $C_1$-$C_3$ alkyl such as methyl, $C_1$-$C_3$ hydroxyalkyl such as hydroxymethyl, $C_1$-$C_3$ haloalkyl such as trifluoromethyl, $C_1$-$C_3$ alkoxy such as methoxy or ethoxy, $C_1$-$C_3$ haloalkoxy such as trifluoromethoxy, $C_{1-3}$alkylthio such as methylthio, $C_{1-3}$alkylsulfonyl such as methylsulfonyl or $C_{1-3}$alkylsulfinyl such as methylsulfinyl.

Suitably however, m is 0.

$R^7$ and $R^8$ each independently represent hydrogen, a 3- to 8- or 5- to 6-membered saturated heterocyclic ring comprising a ring group O, $S(O)_p$ or $N^{10a}$, $C_1$-$C_6$, $C_1$-$C_4$, or $C_1$-$C_2$ alkyl or $C_3$-$C_6$ or $C_5$-$C_6$ cycloalkyl, the latter two groups being optionally substituted by one or more (e.g. one, two, three or four) groups independently selected from halogen (e.g. fluorine, chlorine, bromine or iodine), cyano, $S(O)_qR^{11}$, $OR^{12}$, $CO_2R^{12}$, $OC(O)R^{12}$, $SO_2NR^{12}R^{13}$, $CONR^{12}R^{13}$, $NR^{12}R^{13}$, $NR^{12}SO_2R^{14}$, $NR^{12}COR^{13}$, or a 3- to 8- or 5- to 6-membered saturated heterocyclic ring comprising a ring group O, $S(O)_p$ or $NR^{10b}$, or $R^7$ and $R^8$ together with the nitrogen atom to which they are attached form a 3- to 8-membered saturated heterocyclic ring comprising a ring nitrogen atom and optionally one or more (e.g. one, two or three) further heteroatoms independently selected from nitrogen, oxygen, sulphur and sulphonyl (such as piperidinyl, piperazinyl, morpholinyl or pyrrolidinyl), the heterocyclic ring being optionally substituted by one or more (e.g. one, two, three or four) substituents independently selected from halogen (e.g. fluorine, chlorine, bromine or iodine), cyano, $S(O)_qR^{15}$, $OR^{15}$, $CO_2R^{15}$, $COR^{15}$, $OC(O)R^{15}$, $SO_2NR^{15}R^{16}$, $CONR^{15}R^{16}$, $NR^{15}R^{16}$, $NR^{15}SO_2R^{17}$, $NR^{15}COR^{16}$, $NR^{15}CO_2R^{16}$, heteroaryl (particularly pyrimidinyl), $C_1$-$C_6$, or $C_1$-$C_4$, or $C_1$-$C_2$ haloalkyl (e.g. trifluoromethyl, trifluoromethoxy or pentafluoroethyl), $C_3$-$C_8$ or $C_5$-$C_6$ cycloalkyl and $C_1$-$C_6$, or $C_1$-$C_4$, or $C_1$-$C_2$ alkyl, the latter two groups being optionally substituted by one or more (e.g. one, two, three or four) groups independently selected from cyano, $S(O)_qR^{18}$, $OR^{18}$, $CO_2R^{18}$, $SO_2NR^{18}R^{19}$, $CONR^{18}R^{19}$ or $NR^{18}R^{19}$.

In one embodiment, $R^7$ and $R^8$ each independently represent hydrogen, a 5- to 6-membered saturated heterocyclic ring comprising a ring group O or $NR^{10a}$, or a $C_1$-$C_6$, or $C_1$-$C_4$, or $C_1$-$C_2$ alkyl group optionally substituted by one or more (e.g. one, two, three or four) groups independently selected from halogen (e.g. fluorine, chlorine, bromine or iodine), cyano, $S(O)_qR^{11}$, $OR^{12}$, $CO_2R^{12}$, $OC(O)R^{12}$, $SO_2NR^{12}R^{13}$, $CONR^{12}R^{13}$, $NR^{12}R^{13}$, $NR^{12}SO_2R^{14}$, $NR^{12}COR^{13}$, or a 3- to 8- or 5- to 6-membered saturated heterocyclic ring comprising a ring group O, $S(O)_p$ or $NR^{10b}$.

In another embodiment, $R^7$ and $R^8$ each independently represent hydrogen, a 5- to 6-membered saturated heterocyclic ring comprising a ring group O or $NR^{10a}$, or a $C_1$-$C_4$ alkyl group optionally substituted by one or two groups independently selected from halogen (e.g. fluorine, chlorine, bromine or iodine), cyano, $S(O)_qR^{11}$, $OR^{12}$, $CO_2R^{12}$, $OC(O)R^{12}$, $SO_2NR^{12}R^{13}$, $CONR^{12}R^{13}$, $NR^{12}R^{13}$, $NR^{12}SO_2R^{14}$, $NR^{12}COR^{13}$, or a 3- to 8- or 5- to 6-membered saturated heterocyclic ring comprising a ring group O, $S(O)_p$ or $NR^{10b}$.

In a further embodiment, $R^7$ and $R^8$ each independently represent a 5- to 6-membered saturated heterocyclic ring comprising a ring group O or $NR^{10a}$ (such as tetrahydropyranyl or N-acetylpiperidinyl) or a $C_1$-$C_4$ alkyl group optionally substituted by $OR^{12}$.

In an alternative embodiment, $R^7$ and $R^8$ together with the nitrogen atom to which they are attached form a 3- to 8-membered, particularly 4- to 7- or 5- to 6-membered, saturated heterocyclic ring comprising a ring nitrogen atom and optionally one or more further heteroatoms independently selected from nitrogen, oxygen, sulphur and sulphonyl, the heterocyclic ring being optionally substituted by one or more (e.g. one, two, three or four) substituents independently selected from halogen (e.g. fluorine, chlorine, bromine or iodine), cyano, $S(O)_qR^{15}$, $OR^{15}$, $CO_2R^{15}$, $COR^{15}$, $CONR^{15}R^{16}$, $NR^{15}CO_2R^{16}$, heteroaryl and $C_1$-$C_6$, or $C_1$-$C_4$, or $C_1$-$C_2$ alkyl, the alkyl group being optionally substituted by one or more (e.g. one, two, three or four) groups independently selected from cyano, $S(O)_qR^{18}$, $OR^{18}$, $CO_2R^{18}$, $SO_2NR^{18}R^{19}$, $CONR^{18}R^{19}$ or $NR^{18}R^{19}$.

According to a further embodiment, $R^7$ and $R^8$ together with the nitrogen atom to which they are attached form a 4- to 7-membered saturated heterocyclic ring comprising a ring nitrogen atom and optionally one further heteroatom selected from nitrogen and oxygen, the heterocyclic ring being optionally substituted by one or two substituents independently selected from $S(O)_qR^{15}$, $OR^{15}$, $CO_2R^{15}$, $COR^5$, $CONR^{15}R^{16}$, $NR^{15}CO_2R^{16}$, pyrimidinyl and $C_1$-$C_2$ alkyl, the alkyl group being optionally substituted by one or two groups independently selected from $OR^{18}$ and $CO_2R^{18}$.

Examples of compounds of the invention include:

Methyl 2-(4-((3-(4-amino-2-butyl-1H-imidazo[4,5-c]quinolin-1-yl)propylamino)methyl)phenyl)acetate, Methyl 2-(3-((3-(4-amino-2-butyl-1H-imidazo[4,5-c]quinolin-1-yl)propylamino)methyl)phenyl)acetate, Methyl 2-(4-((N-(3-(4-amino-2-butyl-1H-imidazo[4,5-c]quinolin-1-yl)propyl)-2-(dimethylamino)acetamido)methyl)phenyl)acetate, Methyl 2-(3-((N-(3-(4-amino-2-butyl-1H-imidazo[4,5-c]quinolin-1-yl)propyl)-2-(dimethylamino)acetamido)methyl)phenyl)acetate, Methyl 2-(3-((4-((4-amino-2-(2-methoxyethyl)-1H-imidazo[4,5-c]quinolin-1-yl)methyl)piperidin-1-yl)methyl)phenyl)acetate di-trifluoroacetate salt, Methyl[4-({[3-(4-amino-2-butyl-1H-imidazo[4,5-c]quinolin-1-yl)propyl][2-(dimethylamino)ethyl]amino}methyl)phenyl]acetate, Methyl 2-(3-((N-(3-(4-amino-2-(ethoxymethyl)-1H-imidazo[4,5-c]quinolin-1-yl)propyl)-2-(dimethylamino)acetamido)methyl)phenyl)acetate, Methyl 2-(3-(((3-(4-amino-2-butyl-1H-imidazo[4,5-c]quinolin-1-yl)propyl)(1-methylpiperidin-4-yl)amino)methyl)phenyl)acetate, Methyl 2-(4-(((3-(4-amino-2-butyl-1H-imidazo[4,5-c]quinolin-1-yl)propyl)(1-methylpiperidin-4-yl)amino)methyl)phenyl)acetate, Methyl 2-(4-((N-(3-(4-amino-2-butyl-1H-imidazo[4,5-c]quinolin-1-yl)propyl)-2-(4-methylpiperazin-1-yl)acetamido)methyl)phenyl)acetate, Methyl 2-(3-(((3-(4-amino-2-butyl-1H-imidazo[4,5-c]quinolin-1-yl)propyl)(3-(dimethylamino)propyl)amino)methyl)phenyl)acetate, Methyl 2-(3-(((3-(4-amino-2-butyl-1H-imidazo[4,5-c]quinolin-1-yl)propyl)(3-morpholinopropyl)amino)methyl)phenyl)acetate, Methyl 2-(3-(((3-(4-amino-2-butyl-1H-imidazo[4,5-c]quinolin-1-yl)propyl)(3-(ethyl(methyl)amino)propyl)amino)methyl)phenyl)acetate, Methyl 2-(3-(((3-(4-amino-2-butyl-1H-imidazo[4,5-c]quinolin-1-yl)propyl)(3-(4-methylpiperazin-1-yl)propyl)amino)methyl)phenyl)acetate, Methyl 2-(4-((N-(3-(4-amino-2-butyl-1H-imidazo[4,5-c]quinolin-1-yl)propyl)-2-(methylsulfonyl)acetamido)methyl)phenyl)acetate, Methyl 2-(4-((N-(3-(4-amino-2-butyl-1H-imidazo[4,5-c]quinolin-1-yl)propyl)acetamido)methyl)phenyl)acetate, Methyl 2-(4-((N-(3-(4-amino-2-butyl-1H-imidazo[4,5-c]quinolin-1-yl)propyl)-2-morpholinoacetamido)methyl)phenyl)acetate, Methyl 2-(4-((N-(3-(4-amino-2-butyl-1H-imidazo[4,5-c]quinolin-1-yl)propyl)-2-((2-methoxyethyl)(methyl)amino)acetamido)methyl)phenyl)acetate, Methyl 2-(4-((2-(4-acetylpiperazin-1-yl)-N-(3-(4-amino-2-butyl-1H-imidazo[4,5-c]quinolin-1-yl)propyl)acetamido)methyl)phenyl)acetate, (R)-Methyl 2-(4-((N-(3-(4-amino-2-butyl-1H-imidazo[4,5-c]quinolin-1-yl)propyl)-2-(3-hydroxypyrrolidin-1-yl)acetamido)methyl)phenyl)acetate, Methyl 2-(4-((N-(3-(4-amino-2-butyl-1H-imidazo[4,5-c]quinolin-1-yl)propyl)-2-(4-(pyrimidin-2-yl)piperazin-1-yl)acetamido)methyl)phenyl)acetate, Ethyl 4-(2-((3-(4-amino-2-butyl-1H-imidazo[4,5-c]quinolin-1-yl)propyl)(4-(2-methoxy-2-oxoethyl)benzyl)amino)-2-oxoethyl)piperazine-1-carboxylate, Methyl 2-(4-((N-(3-(4-amino-2-butyl-1H-imidazo[4,5-c]quinolin-1-yl)propyl)-2-(4-(ethylsulfonyl)piperazin-1-yl)acetamido)methyl)phenyl)acetate, Methyl 2-(4-((N-(3-(4-amino-2-butyl-1H-imidazo[4,5-c]quinolin-1-yl)propyl)-2-(piperidin-1-yl)acetamido)methyl)phenyl)acetate, Methyl 2-(4-((N-(3-(4-amino-2-butyl-1H-imidazo[4,5-c]quinolin-1-yl)propyl)-2-(4-(tert-butoxycarbonylamino)piperidin-1-yl)acetamido)methyl)phenyl)acetate, Methyl 2-(4-((N-(3-(4-amino-2-butyl-1H-imidazo[4,5-c]quinolin-1-yl)propyl)-2-(4-(tert-butoxycarbonyl(methyl)amino)piperidin-1-yl)acetamido)methyl)phenyl)acetate, Ethyl 2-(1-(2-((3-(4-amino-2-butyl-1H-imidazo[4,5-c]quinolin-1-yl)propyl)(4-(2-methoxy-2-oxoethyl)benzyl)amino)-2-oxoethyl)piperidin-4-yl)acetate, Methyl 1-(2-((3-(4-amino-2-butyl-1H-imidazo[4,5-c]quinolin-1-yl)propyl)(4-(2-methoxy-2-oxoethyl)benzyl)amino)-2-oxoethyl)piperidine-4-carboxylate, Methyl 2-(4-((N-(3-(4-amino-2-(2-methoxyethyl)-1H-imidazo[4,5-c]quinolin-1-yl)propyl)-2-(piperidin-1-yl)acetamido)methyl)phenyl)acetate, Methyl 2-(4-((N-(3-(4-amino-2-(2-methoxyethyl)-1H-imidazo[4,5-c]quinolin-1-yl)propyl)-2-(dimethylamino)acetamido)methyl)phenyl)acetate, Methyl 2-(3-((N-(3-(4-amino-2-(2-methoxyethyl)-1H-imidazo[4,5-c]quinolin-1-yl)propyl)-2-(piperidin-1-yl)acetamido)methyl)phenyl)acetate, Methyl 2-(4-((N-(3-(4-amino-2-(2-methoxyethyl)-1H-imidazo[4,5-c]quinolin-1-yl)propyl)-2-((2-methoxyethyl)(methyl)amino)acetamido)methyl)phenyl)acetate, Methyl 2-(4-((N-(3-(4-amino-2-(2-methoxyethyl)-1H-imidazo[4,5-c]quinolin-1-yl)propyl)-3-(piperidin-1-yl)propanamido)methyl)phenyl)acetate, Methyl 2-(4-(((3-(4-amino-2-(2-methoxyethyl)-1H-imidazo[4,5-c]quinolin-1-yl)propyl)(3-morpholinopropyl)amino)methyl)phenyl)acetate, (S)-Methyl 2-(4-((N-(3-(4-amino-2-(2-methoxyethyl)-1H-imidazo[4,5-c]quinolin-1-yl)propyl)-2-(2-(methoxymethyl)pyrrolidin-1-yl)acetamido)methyl)phenyl)acetate, (R)-Methyl 2-(4-((N-(3-(4-amino-2-(2-methoxyethyl)-1H-imidazo[4,5-c]quinolin-1-yl)propyl)-2-(2-(methoxymethyl)pyrrolidin-1-yl)acetamido)methyl)phenyl)acetate, Methyl 2-(4-((N-(3-(4-amino-2-(2-methoxyethyl)-1H-imidazo[4,5-c]quinolin-1-yl)propyl)-2-(pyrrolidin-1-yl)acetamido)methyl)phenyl)acetate, Methyl 2-(4-((N-(3-(4-amino-2-(2-methoxyethyl)-1H-imidazo[4,5-c]quinolin-1-yl)propyl)-2-((2-hydroxyethyl)(methyl)amino)acetamido)methyl)phenyl)acetate, Methyl 2-(3-((N-(3-(4-amino-2-butyl-1H-imidazo[4,5-c]quinolin-1-yl)propyl)-2-((2-methoxyethyl)(methyl)amino)acetamido)methyl)phenyl)acetate, Methyl 2-(3-((N-(3-(4-amino-2-butyl-1H-imidazo[4,5-c]quinolin-1-yl)propyl)-2-(butyl(methyl)amino)acetamido)methyl)phenyl)acetate, Methyl 3-((N-(3-(4-amino-2-butyl-1H-imidazo[4,5-c]quinolin-1-yl)propyl)-2-(dipropylamino)acetamido)methyl)phenyl)acetate, Methyl 2-(3-((N-(3-(4-amino-2-butyl-1H-imidazo[4,5-c]quinolin-1-yl)propyl)-2-(bis(2-hydroxyethyl)amino)acetamido)methyl)phenyl)acetate, Methyl 2-(3-((N-(3-(4-amino-2-butyl-1H-imidazo[4,5-c]quinolin-1-yl)propyl)-2-(methyl(tetrahydro-2H-pyran-4-yl)amino)acetamido)methyl)phenyl)acetate, Methyl 2-(3-((N-(3-(4-amino-2-butyl-1H-imidazo[4,5-c]quinolin-1-yl)propyl)-2-(azetidin-1-yl)acetamido)methyl)phenyl)acetate, Methyl 2-(3-((N-(3-(4-amino-2-butyl-1H-imidazo[4,5-c]quinolin-1-yl)propyl)-2-(3-hydroxyazetidin-1-yl)acetamido)methyl)phenyl)acetate, Methyl 2-(3-((N-(3-(4-amino-2-butyl-1H-imidazo[4,5-c]quinolin-1-yl)propyl)-2-(pyrrolidin-1-yl)acetamido)methyl)phenyl)acetate, Methyl 2-(3-((N-(3-(4-amino-2-butyl-1H-imidazo[4,5-c]quinolin-1-yl)propyl)-2-(3-hydroxypyrrolidin-1-yl)acetamido)methyl)phenyl)acetate, (R)-Methyl 2-(3-((N-(3-(4-amino-2-butyl-1H-imidazo[4,5-c]quinolin-1-yl)propyl)-2-(3-hydroxypyrrolidin-1-yl)acetamido)methyl)phenyl)acetate, Methyl 2-(3-((N-(3-(4-amino-2-butyl-1H-imidazo[4,5-c]quinolin-1-yl)propyl)-2-(piperidin-1-yl)acetamido)methyl)phenyl)acetate, Methyl 2-(3-((N-(3-(4-amino-2-butyl-1H-imidazo[4,5-c]quinolin-1-yl)propyl)-2-(4-hydroxypiperidin-1-yl)acetamido)methyl)phenyl)acetate, Methyl 2-(3-((N-(3-(4-amino-2-butyl-1H-imidazo[4,5-c]quinolin-1-yl)propyl)-2-(4-methoxypiperidin-1-yl)acetamido)methyl)phenyl)acetate, Methyl 2-(3-((N-(3-(4-amino-2-butyl-1H-imidazo[4,5-c]quinolin-1-yl)propyl)-2-(4-(dimethylcarbamoyl)piperidin-1-yl)acetamido)methyl)phenyl)acetate, Methyl 2-(3-((N-(3-(4-amino-2-butyl-1H-imidazo[4,5-c]quinolin-1-yl)propyl)-2-morpholinoacetamido)methyl)phenyl)acetate, Methyl 2-(3-((N-(3-(4-amino-2-butyl-1H-imidazo[4,5-c]quinolin-1-yl)propyl)-2-((2S,6R)-2,6-dimethylmorpholino)acetamido)methyl)phenyl)acetate, Methyl 2-(3-((N-(3-(4-amino-2-butyl-1H-imidazo[4,5-c]quinolin-1-yl)propyl)-2-(4-methylpiperazin-1-yl)acetamido)methyl)phenyl)acetate, Methyl 2-(3-((N-(3-(4-amino-2-butyl-1H-imidazo[4,5-c]quinolin-1-yl)propyl)-2-(4-(2-hydroxyethyl)piperazin-1-yl)acetamido)methyl)phenyl)acetate, Methyl 2-(3-((N-(3-(4-amino-2-butyl-1H-imidazo[4,5-c]quinolin-1-yl)propyl)-2-(4-(2-methoxyethyl)piperazin-1-yl)acetamido)methyl)phenyl)acetate, Methyl 2-(3-((2-(4-acetylpiperazin-1-yl)-N-(3-(4-amino-2-butyl-1H-imidazo[4,5-c]quinolin-1-yl)propyl)acetamido)methyl)phenyl)acetate, Methyl 2-(3-((N-(3-(4-amino-2-butyl-1H-imidazo[4,5-c]quinolin-1-yl)propyl)-2-(4-(methylsulfonyl)piperazin-1-yl)acetamido)methyl)phenyl)acetate, Methyl 2-(3-((N-(3-(4-amino-2-butyl-1H-imidazo[4,5-c]quinolin-1-yl)propyl)-2-(azepan-1-yl)acetamido)methyl)phenyl)acetate, Methyl 2-(3-((N-(3-(4-amino-2-butyl-1H-imidazo[4,5-c]quinolin-1-yl)propyl)-2-(1,4-oxazepan-4-yl)acetamido)methyl)phenyl)acetate, Methyl 2-(3-((N-(3-(4-amino-2-butyl-1H-imidazo[4,5-c]quinolin-1-yl)propyl)-2-(4-methyl-1,4-diazepan-1-yl)acetamido)methyl)phenyl)acetate, Methyl 2-(3-((2-(4-acetyl-1,4-diazepan-1-yl)-N-(3-(4-amino-2-butyl-1H-imidazo[4,5-c]quinolin-1-yl)propyl)acetamido)methyl)phenyl)acetate, Methyl 2-(3-((N-(3-(4-amino-2-butyl-1H-imidazo[4,5-c]quinolin-1-yl)propyl)-2-(4-(ethylcarbamoyl)-1,4-diazepan-1-yl)acetamido)methyl)phenyl)acetate, Methyl 2-(3-((N-(3-(4-amino-2-butyl-1H-imidazo[4,5-c]quinolin-1-yl)propyl)-2-(4-(methylsulfonyl)-1,4-diazepan-1-yl)acetamido)methyl)phenyl)acetate, Methyl 2-(4-((N-(3-(4-amino-2-butyl-1H-imidazo[4,5-c]quinolin-1-yl)propyl)-2-(4-(2-methoxyethyl)piperazin-1-yl)acetamido)methyl)phenyl)acetate, Methyl 2-(4-((2-(4-acetyl-1,4-diazepan-1-yl)-N-(3-(4-amino-2-butyl-1H-imidazo[4,5-c]quinolin-1-yl)propyl)acetamido)methyl)phenyl)acetate, Methyl 2-(4-((N-(3-(4-amino-2-butyl-1H-imidazo[4,5-c]quinolin-1-yl)propyl)-2-(4-(methylsulfonyl)-1,4-diazepan-1-yl)acetamido)methyl)phenyl)acetate, Methyl 2-(4-((2-((1-acetylpiperidin-4-yl)(methyl)amino)-N-(3-(4-amino-2-butyl-1H-imidazo[4,5-c]quinolin-1-yl)propyl)acetamido)methyl)phenyl)acetate, Methyl 2-(4-((N-(3-(4-amino-2-(2-methoxyethyl)-1H-imidazo[4,5-c]quinolin-1-yl)propyl)-2-(4-methylpiperazin-1-yl)acetamido)methyl)phenyl)acetate, Methyl 2-(4-((N-(3-(4-amino-2-(2-methoxyethyl)-1H-imidazo[4,5-c]quinolin-1-yl)propyl)-2-(4-(2-methoxyethyl)piperazin-1-yl)acetamido)methyl)phenyl)acetate, Methyl 2-(3-((N-(3-(4-amino-2-(2-methoxyethyl)-1H-imidazo[4,5-c]quinolin-1-yl)propyl)-2-(4-methylpiperazin-1-yl)acetamido)methyl)phenyl)acetate, Methyl 2-(3-((N-(3-(4-amino-2-(2-methoxyethyl)-1H-imidazo[4,5-c]quinolin-1-yl)propyl)-2-(4-(2-methoxyethyl)piperazin-1-yl)acetamido)methyl)phenyl)acetate.

and pharmaceutically acceptable salts of any one thereof.

The present invention further provides a process for the preparation of a compound of formula (I) or a pharmaceutically acceptable salt thereof as defined above which comprises either:

a) where $X^1$ is a group $NR^5$, reacting a compound of formula (II)

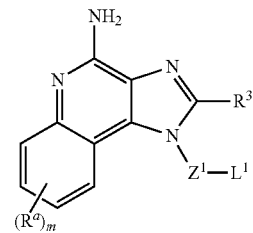

(II)

wherein $Z^1$, $R^3$, $R^a$ and m are as defined in formula (I) and $L^1$ is a leaving group, with a compound of formula (III)

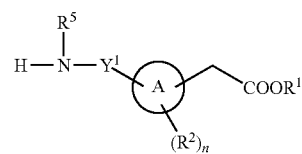

(III)

where $Y^1$, $R^1$, $R^2$, $R^5$, A and n are as defined in formula (I); or b) where $X^1$ is a group $NR^5$ and $Y^1$ is $C_1$-$C_6$ alkylene, reacting a compound of formula (IV)

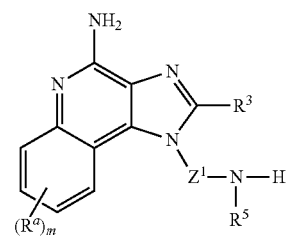

(IV)

where $R^a$, $R^3$, $R^5$, $Z^1$ and m are as defined in formula (I), with a compound of formula (V)

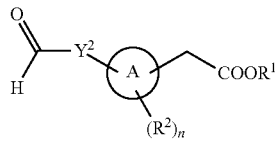
(V)

where $R^1$, $R^2$, A and n are as defined in formula (I) and $Y^2$ is a bond or a $C_{1-5}$alkylene group in the presence of a suitable reducing agent (e.g. sodium triacetoxyborohydride); or (c) where $X^1$ is a group $NR^5$, O or S, reacting a compound of formula (VI)

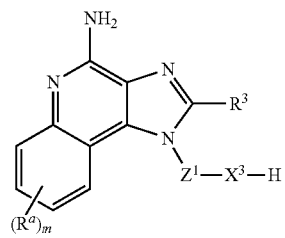
(VI)

wherein $X^3$ is a group $NR^5$, O or S, and $Z^1$, $R^3$, $R^5$, $R^a$ and m are as defined in formula (I), with a compound of formula (VII)

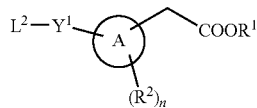
(VII)

where $Y^1$, $R^1$, $R^2$, A and n are as defined in formula (I) and $L^2$ is a leaving group; or (d) where $X^1$ is a group $S(O)_p$ where p is 1 or 2, oxidation of a compound of formula (I) where $X^1$ is S; or (e) where $X^1$ is a group $NR^5CO$, $NR^5SO_2$, $NR^5CONR^6$ or $NR^6CONR^5$, reacting a compound of formula (IVA)

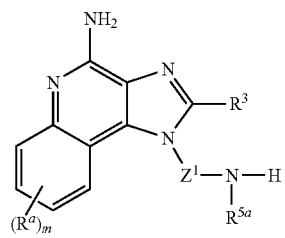
(IVA)

where $R^a$, $R^3$, $Z^1$ and m are as defined in relation to formula (I) and $R^{5a}$ is a group $R^5$ or $R^6$ as defined in relation to formula (I), with a compound of formula (VIII)

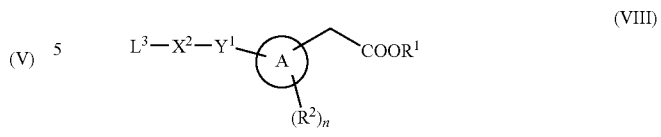
(VIII)

where $L^3$ is a leaving group such as halo, $X^2$ is a CO, $SO_2$, $CONR^6$ or $CONR^5$ group respectively, and $Y^1$, $R^1$, $R^2$, A and n are as defined in relation to formula (I); or (f) where $X^1$ is $CONR^5$ or $SO_2NR^5$, reacting a compound of formula (IX)

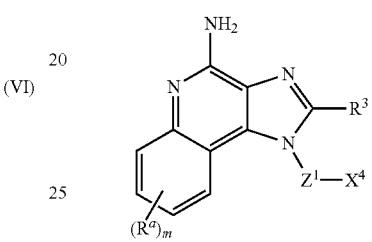
(IX)

where $X^4$ is an activated acid such as an acid chloride or $SO_2Cl$, $R^a$, $R^3$, $Z^1$ and m are as defined in formula (I), with a compound of formula (III) as defined above; or (h) where $X^1$ is $>N-COR^5$ or $>N-SO_2R^5$, reacting a compound of formula (I) where $X^1$ is $NR^5$ where $R^5$ is hydrogen with a compound of formula (X) or (XI) respectively

$$L^4\text{-}COR^5 \qquad (X)$$

$$L^4\text{-}SO_2R^5 \qquad (XI)$$

where $L^4$ is a leaving group such as halo for instance chloro, and $R^5$ is defined in relation to formula (I);

and thereafter, if desired or necessary, carrying out one or more of the following steps:

converting the compound obtained to a further compound of formula (I)

removal of any protecting groups forming a pharmaceutically acceptable salt of the compound.

In reaction (a) and (c) above, suitable leaving groups $L^1$ and $L^2$ are halogen atoms such as bromine, or chlorine, as well as an activated alcohol such as mesylate or tosylate. The reactions may conveniently be carried out in an organic solvent such as acetonitrile, 1-methyl-2-pyrrolidinone or N,N-dimethylformamide at a temperature, for example, in the range from 0 to 150° C. The reaction may be suitably effected by the presence of a base (e.g. sodium carbonate or potassium carbonate).

In process (b), the reaction may conveniently be carried out in an organic solvent such as 1-methyl-2-pyrrolidinone, 1,2-dichloroethane or tetrahydrofuran at a temperature, for example, in the range from 0 to 100° C.

Compounds of formula (II) may be prepared as illustrated in the reaction scheme A:

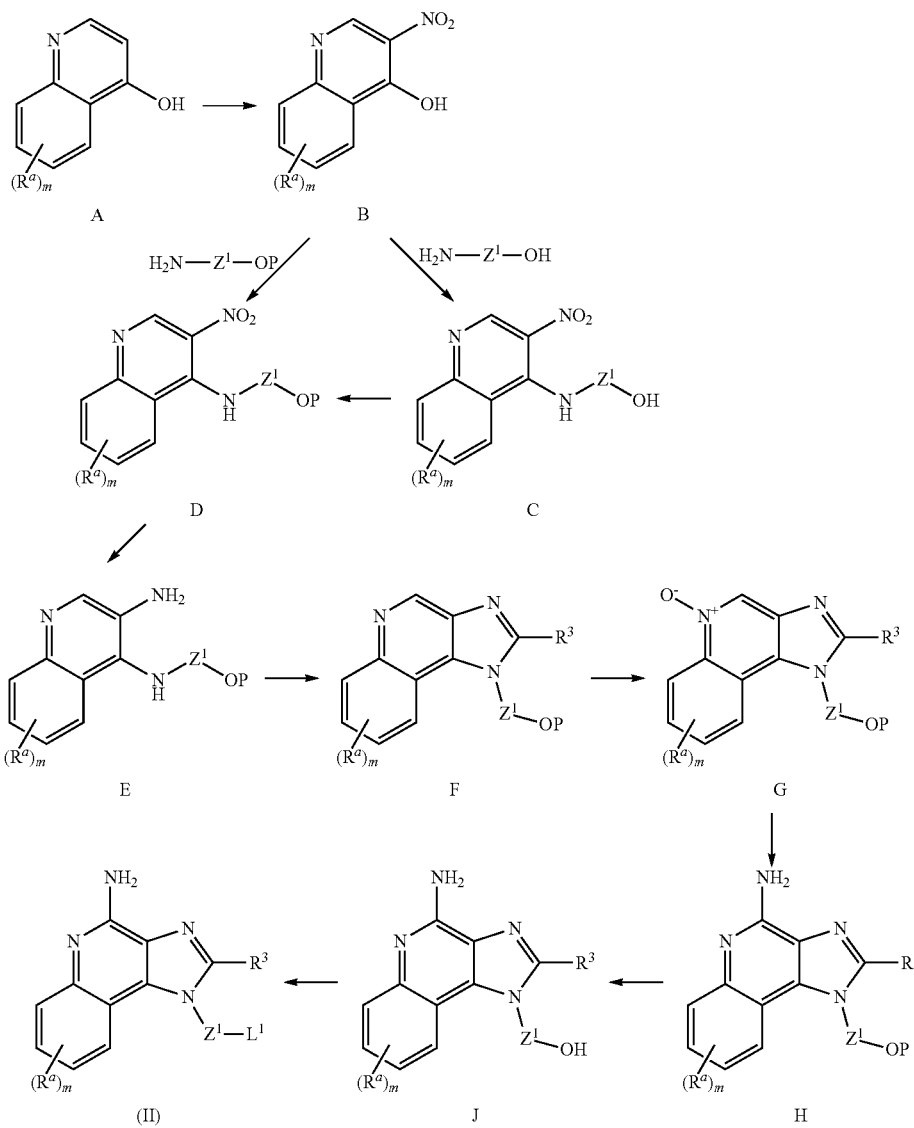

Scheme A where $R^a$, m, $R^3$ and $Z^1$ are as defined in relation to formula (I) and P is a protecting group.

The compound of formula (B) is prepared by nitration of a compound of formula (A). Suitable nitrating agents include nitric acid. The reaction is suitably effected in an organic solvent such as an organic acid such as propionic acid. The reaction may be carried out at elevated temperature, for example from room temperature to 150° C.

Compounds of formula (C) may be prepared by reacting the compound of formula (B) with a mixture of thionyl chloride and DMF to give the aryl chloride which can then be displaced with an aminoalkanol. The chlorination is suitably carried out in a solvent such as dichloromethane, preferably at elevated temperature. The displacement of the chloride with an aminoalkanol, is suitably carried out in the presence of a base for example triethylamine or Hunigs base and in an organic solvent such as dichloromethane, at a temperature in the range from 0 to 40° C.

Compounds of formula (D) are prepared by adding a suitable protecting group to the hydroxy terminal group. This can be effected using conventional chemistry as outlined for example in 'Protective Groups in Organic Synthesis' by Theodora Green (publisher: John Wiley & Sons). A suitable protecting group P for the hydroxy group is, for example, an alkanoyl group such as acetyl, an aroyl group, for example benzoyl, or an arylmethyl group, for example benzyl, or a silyl group for example tert-butyl(dimethyl)silyl. Compounds of formula (D) may also be prepared by adding a protected aminoalkanol to a compound of formula (B), using the same conditions as above.

The compound of formula (D) is then reduced to form a compound of formula (E). Suitable reducing agents include iron powder in a suitable solvent such as acetic acid or sodium borohydride in the presence of a suitable catalyst such as a 15% of nickel chloride in a suitable solvent such as methanol or hydrogenation. Suitable hydrogenation conditions include the use of hydrogen gas at elevated pressure, for example at 2-5 Bar in the presence of a suitable catalyst such as a 1% platinum on carbon catalyst. The reaction is suitably effected at room temperature.

Compounds of formula (E) are then cyclised to form the compound of formula (F). Suitable cyclisation conditions include reaction with an acid chloride in the presence of a base such as triethylamine in a suitable solvent such as N-methyl pyrrolidinone or an acid in the presence of a coupling reagent such as O-(7-azabenzotriazol-1-yl)-N,N,N',N'-tetramethyluroniumhexafluorophosphat purum (HATU) in the presence of a base such as triethylamine in a suitable solvent such as N-methyl pyrrolidine. Alternatively the compound of formula (F) may be prepared by cyclisation reaction with an orthoester in a suitable solvent such as N-methyl pyrrolidinone in the presence of a suitable catalyst such as 10 mol % of toluensulphuric acid. The reaction is suitably effected at elevated temperatures, for example from 30-150° C.

Compounds of formula (F) may be oxidised to compounds of formula (G) by reaction with an oxidising agent such as meta-chloroperoxybenzoic acid or hydrogen peroxide. The reaction is suitably effected in an organic solvent such as dichloromethane or ethanol at reduced temperatures for example in the range of −10° C. to room temperature.

Subsequently, the compound of formula (G) is reacted with p-toluenesulphonyl chloride and aqueous ammonia to convert it to the compound of formula (H). The reaction is suitably effected in an organic solvent such as dichloromethane. Temperatures in the range from 0-40° C. and conveniently at room temperature are suitably employed.

Deprotection of the resultant compound of formula (H) yields a compound of formula (J). The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively a benzyl group may be removed, for example, by hydrogenation over a catalyst such as palladium-on-carbon.

The product of formula (J) is then converted to a compound of formula (II) by formation of a suitable leaving group such as halo, for instance chloro or bromo, or an activated alcohol such as a mesylate or tosylate. For example, the chloride may be formed by reacting the compound of formula (J) with thionyl chloride. Preferably in a solvent such as dichloromethane at a temperature between 20-40° C.

Compounds of formulae (IV) and (IVA) may be prepared by an analogous route as illustrated in Scheme B.

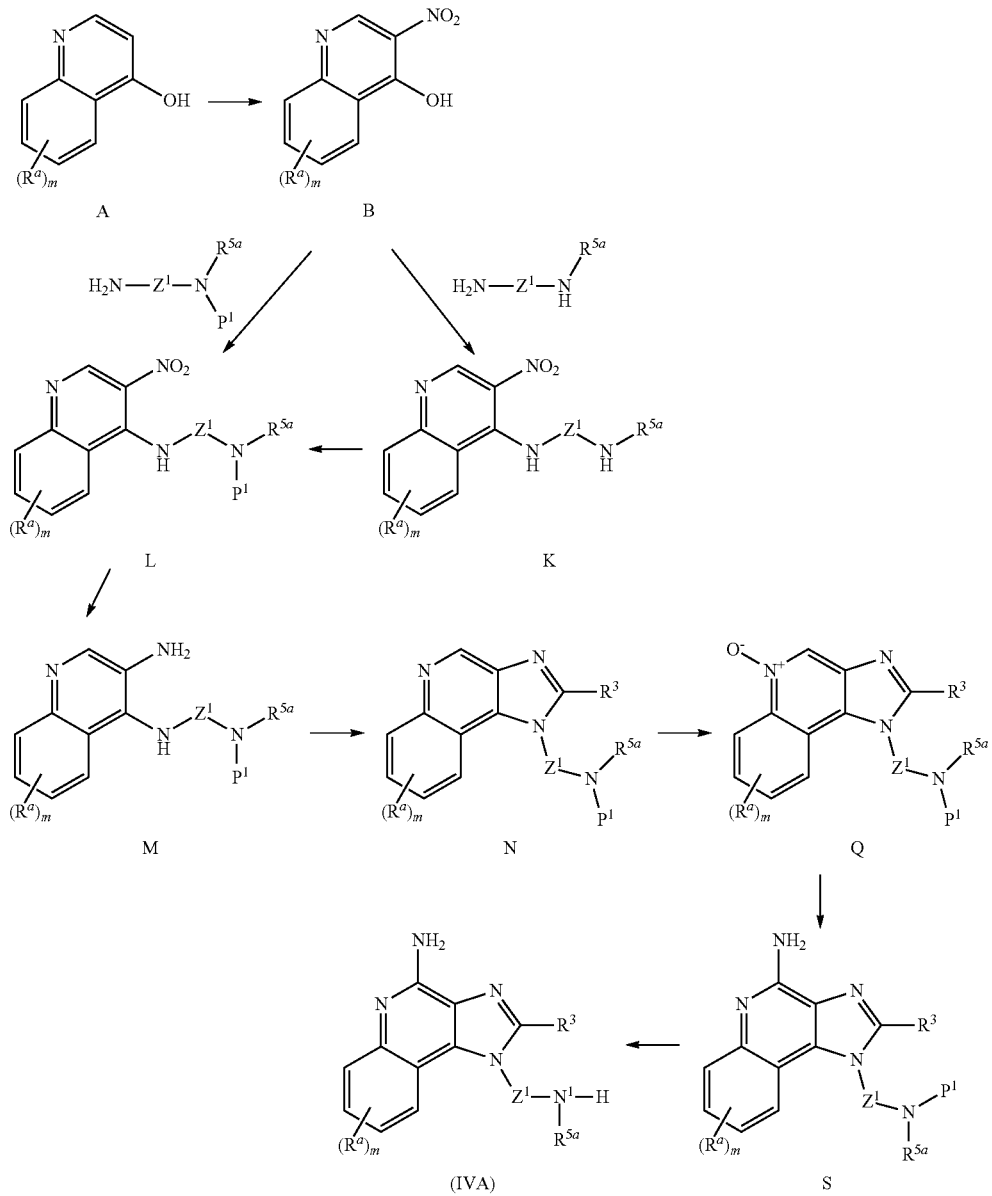

Scheme B where $R^a$, m, $R^3$ and $Z^1$ are as defined in relation to formula (I), $R^{5a}$ is as defined in relation to formula (IVA) and $P^1$ is an amino protecting group.

Compounds of formula (K) or (L) may be prepared by reacting the compound of formula (B) with a mixture of thionyl chloride and DMF to give the aryl chloride which can then be displaced with a di-amino alkane, or a protected form thereof. The chlorination is suitably carried out in a solvent such as dichloromethane, preferably at elevated temperature. The displacement of the chloride with a di-amino alkane, or a protected form thereof, is suitably carried out in the presence of a base for example triethylamine or Hunigs base and in an organic solvent such as dichloromethane, at a temperature in the range from 0 to 40° C.

Where a diaminoalkane is used, a compound of formula (K) is prepared which may be subsequently protected to form a compound of formula (L) using conventional methods.

A suitable protecting group $P^1$ is for example, a group such as an alkoxycarbonyl group, for example a methoxycarbonyl, ethoxycarbonyl or t-butoxycarbonyl group, an arylmethoxycarbonyl group, for example benzyloxycarbonyl. A suitable alternative protecting group for a primary amino group is, for example, a phthaloyl group.

Reduction of the product of formula (L) using for example analogous conditions to those described above for the reduction of the compound of formula (D), will yield a compound of formula (M). This in turn may be cyclised to a compound of formula (N) using conditions analogous to those described above for the cyclisation of the compound of formula (E), oxidised to a compound of formula (Q) using conditions analogous to those described above for the oxidation of the compound of formula (F), and the product reacted with p-toluenesulphonyl chloride and aqueous ammonia to form the compound of formula (S) using for example conditions analogous to those described above for the preparation of the compound of formula (H).

Deprotection of the resultant compound of formula (S) yields a compound of formula (IV). The deprotection conditions for the above protecting groups necessarily vary with the choice of protecting group. Thus, for example, an alkoxycarbonyl group may be removed for example, by hydrolysis with a suitable base such as an alkali metal hydroxide, for example lithium or sodium hydroxide. Alternatively an alkoxycarbonyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A phthaloyl protecting group which be removed by treatment with an alkylamine, for example dimethylaminopropylamine, or with hydrazine.

Suitably in Scheme B, $R^5$ is hydrogen, which may be converted to a different $R^5$ group later, for example once the compound of formula (IV) has been converted to a compound of formula (I).

Compounds of formula (VI) where $X^1$ is $NR^5$ may be prepared by reacting compounds of formula (II) with compounds of formula (XII)

$R^5NH_2$ (XII)

Coupling conditions will be similar to those described above for the reactions (a) and (c).

Compounds of formula (I) may be converted to other compounds of formula (I) using conventional methods. For example, in process (h) above, compounds where $R^5$ is hydrogen may be reacted with compounds of formula (X) or (XI);

$L^4\text{-COR}^5$ (X)

or

$L^4\text{-SO}_2R^5$ (XI)

where $L^4$ is a leaving group such as halo for instance chloro, and $R^5$ is defined in relation to formula (I). The reaction is suitably carried out in an organic solvent such as acetonitrile, dimethylformamide and/or dichloromethane optionally in the presence of a base such as triethylamine. Temperatures in the range from 0 to 150° C. are suitably employed.

Similarly, oxidation of compounds of formula (I) during process (d) above can be carried out under conventional conditions, for example by reaction with an oxidising agent such as meta-chloroperoxybenzoic acid or hydrogen peroxide. The reaction is suitably effected in an organic solvent such as dichloromethane or ethanol at temperatures for example in the range of 0-40° C.

Compounds of formula (IX) above where $X^4$ is an activated acid such as an acid chloride are suitably prepared by a reaction as set out in Scheme C.

Scheme C

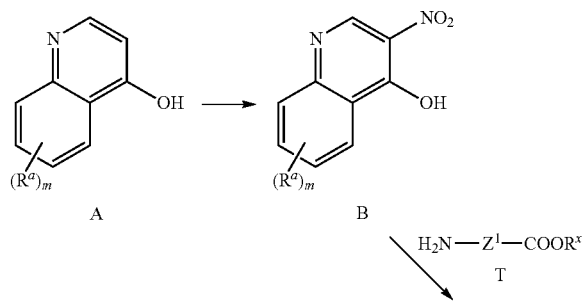

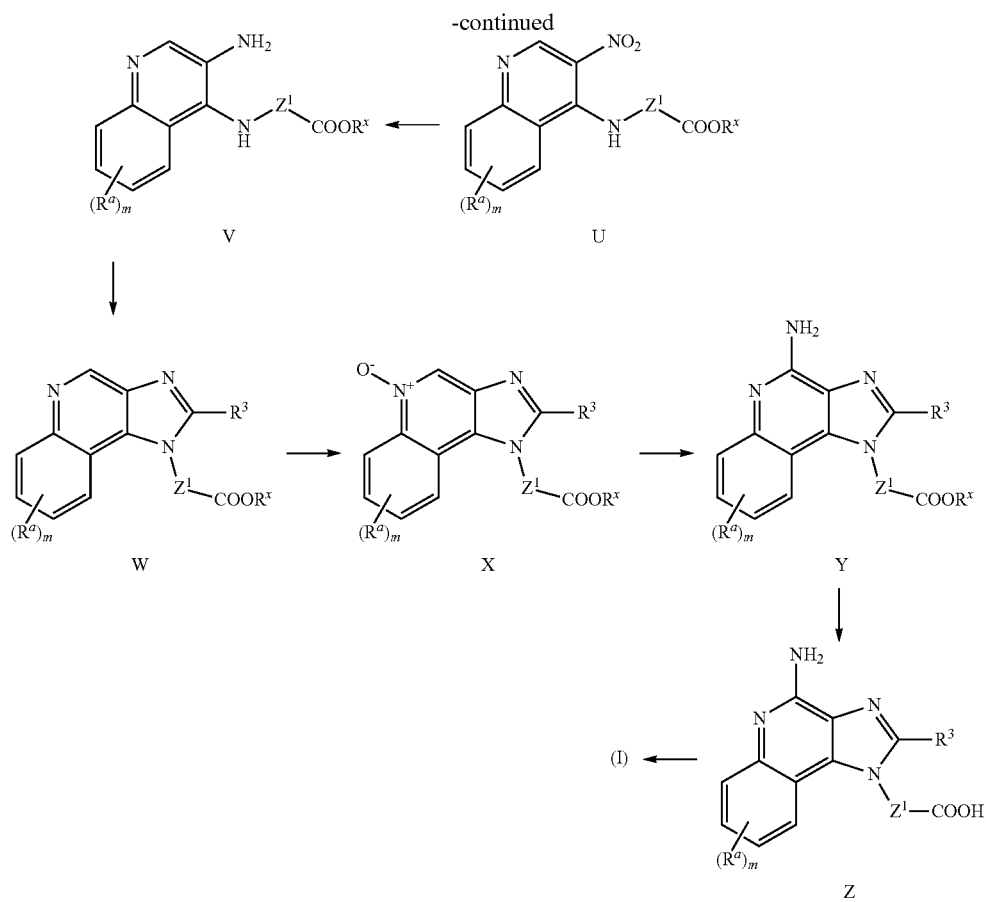

Conditions used for the reactions shown in Scheme C are generally similar to those used in analogous steps in Scheme B. A compound of formula Y may be converted to a compound of formula Z with a base such as lithium or sodium hydroxide, in a suitable solvent such as tetrahydrofuran or methanol and water. Alternatively the ester may be hydrolysed under acidic conditions such as aqueous HCl, preferably at elevated temperature. A compound of formula (I) may be prepared from a compound of formula (Z) by activation of the acid to an acyl halide, such as chloride with a reagent such as thionyl chloride then treated with a compound of formula (III). The formation of the acid chloride may conveniently be carried out neat or in an organic solvent such as dichloromethane at a temperature, for example, in the range from 0 to 80° C. The activated acid is then treated with a compound of formula (III), the reaction may conveniently be carried out in an organic solvent such as tetrahydrofuran or dimethylformamide, with a base such as triethylamine at a temperature, for example, in the range from 0 to 80° C. Alternatively the acid may be activated with a coupling agent such as 1,3-dicyclohexylcarbodiimide or benzotriazol-1-yloxytripyrrolidinophosphonium hexafluorophosphate.

Compounds of formula (IX) above where $X^4$ is $SO_2Cl$ may be prepared by reacting a compound of formula (II) with sodium sulphite, then treatment of the sulphonate with a chlorinating reagent such as thionyl chloride or phosphorous pentachloride to give the sulphonyl chloride. The sulphonyl chloride may then be reacted with a compound of formula (III) to give a compound of formula (I). The reaction may conveniently be carried out in an organic solvent such as tetrahydrofuran or dichloromethane, with a base such as triethylamine at a temperature, for example, in the range from 0 to 80° C.

A compound of formula (I) in which $X^1$ is $NR^5$ and $R^5$ is hydrogen may be converted to a corresponding compound of formula (I) in which $R^5$ is —$COCH_2NR^7R^8$ by reaction with chloroacetyl chloride followed by an amine of formula $R^7R^8NH$ where $R^7$ and $R^8$ are as defined above. The first stage is suitably carried out in an organic solvent such as dichloromethane or acetonitrile, with one equivalent of chloroacetyl chloride. Temperatures in the range from 0° C. to 50° C. are suitably employed. In the second stage the reaction is suitably carried out in an organic solvent such as dichloromethane or acetonitrile, with excess of an amine $R^7R^8NH$. Temperatures in the range from 0° C. to 100° C. are suitably employed.

A compound of formula (I) in which $X^1$ is $NR^5$ and $R^5$ is hydrogen may also be converted to a corresponding compound of formula (I) in which $R^5$ is a $C_1$-$C_6$ alkyl (e.g. propyl) group substituted by $NR^7R^8$ by reaction with a compound of formula (XX), $L^{10}$-$R^5$, where $L^{10}$ is a leaving group such as halo for instance chloro and $R^5$ is as defined above. The reaction is suitably carried out in an organic solvent such as dimethylformaldehyde or acetonitrile, with preferably one equivalent of formula (XX) compound optionally in the presence of a base such as triethylamine and a salt such as sodium iodide or potassium iodide. Temperatures in the range from 0° C. to 100° C. are suitably employed.

A compound of formula (I) in which $X^1$ is $NR^5$ and $R^5$ is a $C_1$-$C_6$ alkyl (e.g. propyl) group substituted by $NR^7R^8$ may also be prepared by reacting a compound of formula (XIII)

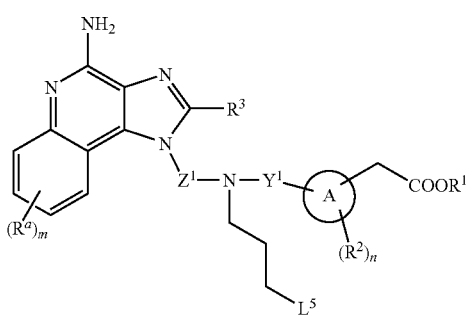

(XIII)

where $L^5$ is a leaving group for example chloro or mesylate and m $R^a$, $R^1$, n, $R^2$, $R^3$, A, $Z^1$ and $Y^1$ are as defined above, with an amine of formula (XXI), $R^7R^8NH$, where $R^7$ and $R^8$ are as defined above. The reaction may be carried out using an excess of the amine $R^7R^8NH$ in an organic solvent such as DMF or dioxane at a temperature in the range of, for example, 40° C.-150° C. Sodium iodide may be used as an additive in the reaction.

A compound of formula (XIII) may be prepared from a corresponding compound of formula (XIV)

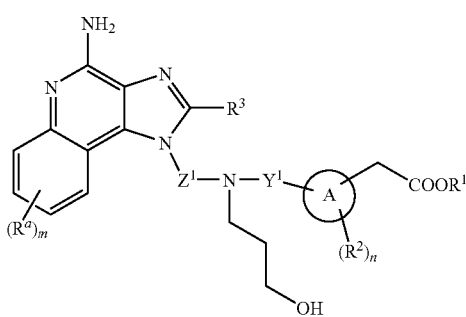

(XIV)

The alcohol may be converted into a leaving group using conventional methods, for example, by reaction with thionyl chloride in an appropriate solvent such as DCM at a temperature from 20-100° C.

A compound of formula (XIV) may be formed using the route in scheme A and the chemistry above.

Compounds of formulae (III), (V), (VII), (VIII), A, (XII), (XX) and (XXI) are known compounds or can be prepared from known compounds by conventional methods.

It will be appreciated by those skilled in the art that in the processes of the present invention certain functional groups such as hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a hydrochloride, hydrobromide, trifluoroacetate, sulphate, phosphate, acetate, fumarate, maleate, tartrate, lactate, citrate, pyruvate, succinate, oxalate, methanesulphonate or p-toluenesulphonate. Preferred salts include dimethane sulphonic acid, monosaccharin, disaccharin, di-1-hydroxy-2-naphthoic acid (di-xinafoate), dibenzenesulphonic acid (di-besylate), mandelic and fumaric acid salts.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) and their pharmaceutically acceptable salts have activity as pharmaceuticals, in particular as modulators of toll-like receptor (especially TLR7) activity, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;
6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;
7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and,
8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, para-influenza; bacterial diseases such as tuberculosis and mycobacterium avium, leprosy; other infectious diseases, such as fungal diseases, chlamydia, candida, aspergillus, cryptococcal meningitis, pneumocystis carnii, cryptosporidiosis, histoplasmosis, toxoplasmosis, trypanosome infection and leishmaniasis.

The compounds of formula (I) and their pharmaceutically acceptable salts have antedrug properties. An antedrug is defined as an active synthetic derivative that is designed to undergo biotransformations to a readily excretable less active form upon entry into the systemic circulation, therefore minimizing systemic side-effects. Thus, on administration, a compound of the invention is rapidly degraded enzymatically to yield a degradation product having a substantially reduced medical effect. A medical effect as defined herein means a pharmacological activity of the compound of the invention, including specifically interferon inducing activity and/or suppression of IL-4/IL-5 production activity.

The medical effect of the degradation product is preferably 10 times, more preferably 100 times less than that of the compound of the invention (i.e. parent compound).

The pharmacological activity can be measured using methods known in the art, preferably using in vitro evaluation methods such as commercially available ELISA kits or the biological assay described in Example 7 of the present specification.

Thus, the present invention provides a compound of formula (I) or a pharmaceutically-acceptable salt thereof as hereinbefore defined for use in therapy.

In a further aspect, the present invention provides the use of a compound of formula (I) or a pharmaceutically acceptable salt thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In particular, the compounds of the invention may be used in the treatment of asthma, COPD, allergic rhinitis, allergic conjunctivitis, atopic dermatitis, cancer, hepatitis B, hepatitis C, HIV, HPV, bacterial infections and dermatosis.

The anti-cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4- fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-yl-propoxy)quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The invention still further provides a method of treating, or reducing the risk of, an obstructive airways disease or condition (e.g. asthma or COPD) which comprises administering to a patient in need thereof a therapeutically effective amount of a compound of formula (I) or a pharmaceutically acceptable salt thereof as hereinbefore defined.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

Dry powder formulations and pressurized HFA aerosols of the compounds of the invention (including pharmaceutically acceptable salts) may be administered by oral or nasal inhalation. For inhalation, the compound is desirably finely divided. The finely divided compound preferably has a mass median diameter of less than 10 micrometres (μm), and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound of the invention with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure.

This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the abovementioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention may also be administered in conjunction with other compounds used for the treatment of the above conditions.

The invention therefore further relates to combination therapies wherein a compound of the invention or a pharmaceutical composition or formulation comprising a compound of the invention is administered concurrently or sequentially or as a combined preparation with another therapeutic agent or agents, for the treatment of one or more of the conditions listed.

In particular, for the treatment of the inflammatory diseases COPD, asthma and allergic rhinitis the compounds of the invention may be combined with agents such as tumour necrosis factor alpha (TNF-alpha) inhibitors such as anti-TNF monoclonal antibodies (for example Remicade, CDP-870 and adalimumab) and TNF receptor immunoglobulin molecules (such as Enbrel); non-selective cyclo-oxygenase COX-1/COX-2 inhibitors whether applied topically or systemically (such as piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (such as meloxicam, celecoxib, rofecoxib, valdecoxib, lumarocoxib, parecoxib and etoricoxib); glucocorticosteroids (whether administered by topical,oral, intramuscular, intravenous, or intra-articular routes); methotrexate, lefunomide; hydroxychloroquine, d-penicillamine, auranofin or other parenteral or oral gold preparations.

The present invention still further relates to the combination of a compound of the invention and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY×1005.

The present invention further relates to the combination of a compound of the invention and a receptor antagonist for leukotrienes (LT B4, LTC4, LTD4, and LTE4) selected from the group consisting of the phenothiazin-3-1s such as L-651, 392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY× 7195.

The present invention still further relates to the combination of a compound of the invention and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention and a gastroprotective histamine type 2 receptor antagonist.

The present invention further relates to the combination of a compound of the invention and an antagonist of the histamine type 4 receptor.

The present invention still further relates to the combination of a compound of the invention and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention and an anticholinergic agent including muscarinic receptor (M1, M2, and M3) antagonists such as atropine, hyoscine, glycopyrrrolate, ipratropium bromide, tiotropium bromide, oxitropium bromide, pirenzepine or telenzepine.

The present invention still further relates to the combination of a compound of the invention together with a beta-adrenoceptor agonist (including beta receptor subtypes 1-4) such as isoprenaline, salbutamol, formoterol, salmeterol, terbutaline, orciprenaline, bitolterol mesylate, and pirbuterol.

The present invention further relates to the combination of a compound of the invention and a chromone, such as sodium cromoglycate or nedocromil sodium.

The present invention still further relates to the combination of a compound of the invention together with an insulin-like growth factor type I (IGF-1) mimetic.

The present invention still further relates to the combination of a compound of the invention and a glucocorticoid, such as flunisolide, triamcinolone acetonide, beclomethasone dipropionate, budesonide, fluticasone propionate, ciclesonide or mometasone furoate.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12.

The present invention still further relates to the combination of a compound of the invention together with modulators of chemokine receptor function such as antagonists of CCR1, CCR2, CCR2A, CCR2B, CCR3, CCR4, CCR5, CCR6, CCR7, CCR8, CCR9, CCR10 and CCR11 (for the C-C family); CXCR1, CXCR2, CXCR3, CXCR4 and CXCR5 (for the C-X-C family) and CX3CR1 for the C-X3-C family.

The present invention still further relates to the combination of a compound of the invention together with a cytokine or modulator of cytokine function, including alpha-, beta-, and gamma-interferon; interleukins (IL) including IL1 to 15, and interleukin antagonists or inhibitors, including agents which act on cytokine signalling pathways.

The present invention still further relates to the combination of a compound of the invention together with an immunoglobulin (Ig) or Ig preparation or an antagonist or antibody modulating Ig function such as anti-IgE (omalizumab).

The present invention further relates to the combination of a compound of the invention and another systemic or topically-applied anti-inflammatory agent, such as thalidomide or a derivative thereof, a retinoid, dithranol or calcipotriol.

The present invention further relates to the combination of a compound of the invention together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

A compound of the invention can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The present invention will be further explained by reference to the following illustrative examples.

EXPERIMENTAL

Unless otherwise stated organic solutions were dried over magnesium sulphate. RPHPLC means reversed phase preparative HPLC using Waters Symmetry C8, Xterra, Xbridge or Phenomenex Gemini columns using acetonitrile and either aqueous ammonium acetate, ammonia, formic acid or trifluoroacetic acid as buffer where appropriate. Column chromatography was carried out on silica gel. Treating with SCX means the mixture was absorbed on SCX and eluted with an appropriate solvent such as methanol or acetonitrile then the free base product eluted with aqueous ammonia/methanol.

The following abbreviations are used;

| | |
|---|---|
| EtOAc | ethyl acetate |
| DCM | dichloromethane |
| NMP | N-methylpyrrolidinone |
| NBS | N-bromosuccinimide |
| DMF | N,N-dimethylformamide |
| DMSO | dimethylsulfoxide |
| THF | tetrahydrofuran |

-continued

| | |
|---|---|
| MeOH | methanol |
| TFA | trifluoroacetic acid |
| HCl | hydrogen chloride |
| $K_2CO_3$ | potassium carbonate |
| $NaHCO_3$ | sodium hydrogen carbonate |
| TEA | triethylamine |
| MeCN | acetonitrile |
| HATU | O-(7-azabezotriazol-1-yl)-N,N,N',N'-tetramethyluronium hexafluorophosphate |
| EDCI | N-(3-dimethylaminopropyl)-N'-ethylcarbodiimide hydrochloride |
| HOBt | 1-hydroxybenzotriazole |
| rt | room temperature |
| h | hours |
| min | minutes |
| M | molar |
| MS | mass spectrometry |
| PyBop | Benzotriazol-l-yloxytripyrrolidinophosphonium hexafluorophosphate |
| APCI | atmospheric chemical ionisation method |
| ESI | electron spray ionisation method |
| NMR | nuclear magnetic resonance |

Instrument Details:

XRPD—PANalytical CubiX PRO machine in Ø-Ø configuration over the scan range 2° to 40° 2Ø with 100-second exposure per 0.02° increment. The X-rays were generated by a copper long-fine focus tube operated at 45 kV and 40 mA. The wavelength of the copper X-rays was 1.5418 Å. The Data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.

DSC thermograms were measured using a TA Q1000 Differential Scanning Calorimeter, with aluminium pans and pierced lids. The sample weights varied between 0.3 to 5 mg. The procedure was carried out under a flow of nitrogen gas (50 mL/min) and the temperature studied from 25 to 300° C. at a constant rate of temperature increase of 10° C. per minute.

Example 1

Methyl 2-(4-((3-(4-amino-2-butyl-1H-imidazo[4,5-c]quinolin-1-yl)propylamino)methyl)phenyl)acetate

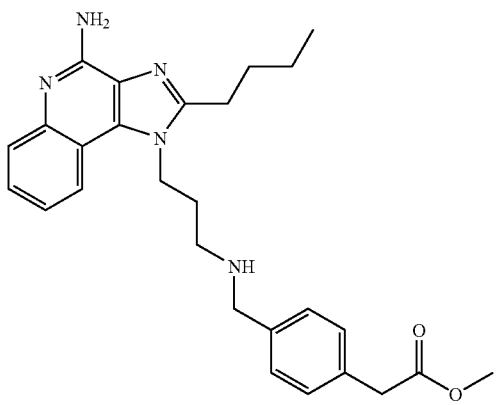 [SMILES: CCCCc1nc2c(N)nc3ccccc3c2n1CCCNCc1ccc(CC(=O)OC)cc1]

(i) 3-Nitroquinolin-4-ol

4-Hydroxyquinoline (22.2 g) and propionic acid (200 mL) were combined and heated to 125° C. Nitric acid (21.5 mL) was added dropwise over 1.5 h. The reaction mixture was stirred at reflux temperature for a further 15 min and cooled to rt. The mixture was diluted with ethanol and the solid was collected by vacuum filtration. The solid was washed with ethanol, water then ethanol. The residue was refluxed in ethanol and the hot mixture was filtered and dried to give the subtitle compound. Yield: 22 g $^1$H NMR δ (DMSO-$d_6$) 13.00 (1H, s), 9.19 (1H, s), 8.26 (1H, m), 7.81 (1H, ddd), 7.75-7.71 (1H, m), 7.53 (1H, ddd)

(ii) tert-Butyl{3-[(3-nitroquinolin-4-yl)amino]propyl}carbamate

To a stirred solution of 3-nitroquinolin-4-ol (8.15 g) in DCM (100 mL) was added DMF (3.33 mL) and thionyl chloride (3.47 mL) and the reaction mixture was refluxed for 2.5 h when all solids dissolved. The solution was cooled to 0° C. and a solution of (3-aminopropyl)-carbamic acid tert-butyl ester (8.3 g) and $Et_3N$ (6.5 mL) in DCM (20 mL) was added dropwise. The reaction mixture was stirred overnight then poured into saturated sodium bicarbonate solution and the product extracted using DCM. The combined organic layer were washed with brine, water, dried, filtered and the solvents evaporated. The residue was triturated with diethylether to leave the subtitle compound (13 g).

$^1$H NMR δ ($CDCl_3$) 9.66 (1H, s), 9.36 (1H, s), 8.32 (1H, d), 8.00 (1H, d), 7.77 (1H, t), 7.49 (1H, ddd), 4.65 (1H, s), 4.01 (2H, dd), 3.33 (2H, q), 2.02 (2H, quintet), 1.40 (9H, s)

MS: APCI (+ve): 347

(iii) tert-Butyl{3-[(3-aminoquinolin-4-yl)amino]propyl}carbamate

The product from step (ii) (12 g) was dissolved in dry THF (250 mL), 1% Pt/C catalyst (3 g) was added and the reaction mixture hydrogenated ($H_2$ pressure: 3 bar) for 72 h at rt. The product was filtered through a glass fibre filter paper and purified via neutral Aluminum oxide column eluting with 4% MeOH in DCM and further purified via RPHPLC to give subtitle compound, yield 1.3 g.

$^1$H NMR δ ($CD_3OD$) 8.34 (1H, s), 8.09-8.02 (1H, m), 7.80-7.74 (1H, m), 7.44-7.38 (2H, m), 3.34-3.30 (2H, m), 3.21-3.10 (2H, m), 1.78-1.67 (2H, m), 1.42 (9H, s)

(iv) tert-Butyl[3-(2-butyl-1H-imidazo[4,5-c]quinolin-1-yl)propyl]carbamate

The product from step (iii) (1.23 g) was dissolved in NMP (25 mL) and valeryl chloride (0.46 mL) was added dropwise. The reaction mixture was stirred for 1.5 h at rt, heated to 50° C. for 24 h then heated to 80° C. for 2 days. The solvent was evaporated and the reaction mixture poured into DCM. The solid precipitate was filtered off and the filtrate was purified on silica eluting with 10% MeOH in DCM to give subtitle compound (0.9 g).

$^1$H NMR δ ($CDCl_3$) 9.29 (1H, s), 8.28 (1H, dd), 8.20 (1H, d), 7.72-7.59 (2H, m), 4.80-4.69 (1H, m), 4.60 (2H, t), 3.03-2.92 (2H, m), 2.72 (1H, s), 2.21-2.09 (2H, m), 1.57-1.50 (2H, m), 1.48 (9H, s), 1.02 (3H, t) 2H under NMP peak MS: APCI (+ve): 383

(v) tert-Butyl[3-(2-butyl-5-oxido-1H-imidazo[4,5-c]quinolin-1-yl)propyl]carbamate The product from step (iv) (0.9 g) was dissolved in DCM (25 mL) and cooled to 5° C. 3-Chloroperoxybenzoic acid (0.203 g) was added and the reaction was allowed to warm to rt. The reaction mixture was stirred for 2 h, more 3-chloroperoxybenzoic acid (0.30 g) was added and the reaction mixture stirred for a further 2 h. The reaction mixture was poured into saturated sodium bisulfate solution, extracted with DCM, dried, filtered and evaporated to give the subtitle (0.9 g).

MS: APCI (+ve): 399

(vi) tert-Butyl[3-(4-amino-2-butyl-1H-imidazo[4,5-c]quinolin-1-yl)propyl]carbamate p-Toluenesulphonyl chloride (0.43 g) was added portionwise to a vigourously stirred mixture of the product from step (v) (0.9 g) in DCM (25 mL) and ammonium hydroxide solution (35%, 2.5 mL) at 0° C. The mixture was allowed to warm to rt over 2 h then partitioned between water/DCM, washed with saturated sodium bicarbonate solution, dried, filtered and the solvent evaporated. The solid product was triturated with diethylether to give the subtitle compound (0.6 g).
MS: APCI (+ve): 398

(vii) 1-(3-Aminopropyl)-2-butyl-1H-imidazo[4,5-c]quinolin-4-amine

The product from step (vi) (0.6 g) was dissolved in DCM (5 mL) and TFA (5 mL) was added. The reaction mixture was stirred for 20 min, the solvents were evaporated and the product purified via SCX resin, eluting with ammonia in MeOH solution (3.5%). Yield 380 mg.
$^1$H NMR δ (CDCl$_3$) 8.06 (1H, d), 7.83 (1H, d), 7.50 (1H, t), 7.33 (1H, t), 4.59 (2H, t), 3.02-2.80 (4H, m), 2.15-1.97 (2H, m), 1.96-1.77 (2H, m), 1.60-1.41 (2H, m), 1.01 (3H, t).
MS: APCI (+ve): 298

(viii) Methyl 2-(4-((3-(4-amino-2-butyl-1H-imidazo[4,5-c]quinolin-1-yl)propylamino)methyl)phenyl)acetate The product from step (vii) (55 mg) was combined with methyl (4-formylphenyl)acetate (0.0329 g) and stirred in THF (15 mL) for 16 h. Sodium borohydride (0.015 g) was added followed by MeOH (3 drops) and the reaction mixture was stirred for 1 h. The reaction mixture was diluted with MeOH and purified via RPHPLC to give the title compound. Yield 17 mg.
$^1$H NMR δ (DMSO-d$_6$) 8.12 (1H, d), 7.60 (1H, d), 7.40 (1H, t), 7.30 (2H, d), 7.23-7.16 (3H, m), 6.41 (2H, s), 4.58 (2H, t), 3.71-3.63 (4H, m), 3.60 (3H, s), 2.93 (2H, t), 2.63-2.57 (2H, m), 2.02-1.92 (2H, m), 1.83-1.73 (2H, m), 1.47-1.37 (2H, m), 1.00-0.89 (3H, m).
MS: APCI (+ve): 460

Example 2

Methyl 2-(3-((3-(4-amino-2-butyl-1H-imidazo[4,5-c]quinolin-1-yl)propylamino)methyl)phenyl)acetate

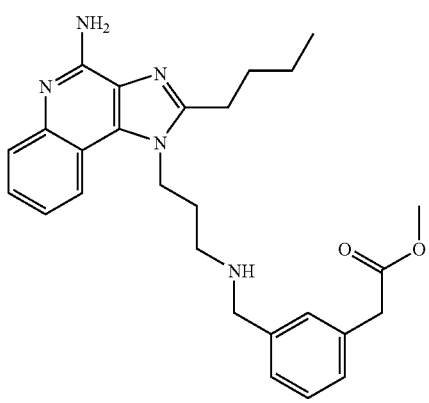 [SMILES: CCCCc1nc2c(N)nc3ccccc3c2n1CCCNCc1cccc(CC(=O)OC)c1]

The title compound was prepared by the method of example 1 using methyl (3-formylphenyl)acetate (34 mg) to afford the title compound, 13 mg as a white solid.

$^1$H NMR δ (DMSO-d$_6$) 8.13 (1H, d), 7.60 (1H, d), 7.40 (1H, t), 7.28-7.23 (3H, m), 7.21-7.16 (1H, m), 7.15-7.11 (1H, m), 6.41 (2H, s), 4.62-4.54 (2H, m), 3.69 (2H, s), 3.65 (2H, s), 3.60 (3H, s), 2.94 (2H, t), 2.63-2.58 (2H, m), 2.02-1.91 (2H, m), 1.84-1.73 (2H, m), 1.44 (2H, q), 0.95 (3H, t)
MS: APCI (+ve): 460

Example 3

Methyl 2-(4-((N-(3-(4-amino-2-butyl-1H-imidazo[4,5-c]quinolin-1-yl)propyl)-2-(dimethylamino)acetamido)methyl)phenyl)acetate

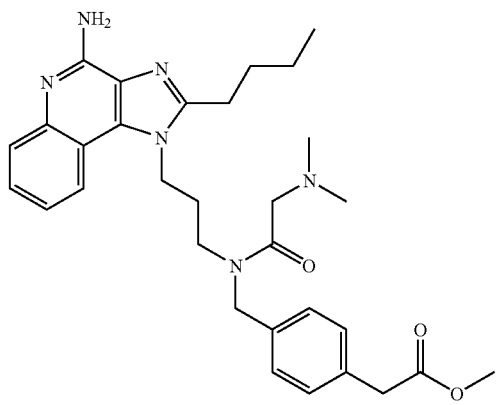 [SMILES: CCCCc1nc2c(N)nc3ccccc3c2n1CCCN(Cc1ccc(CC(=O)OC)cc1)C(=O)CN(C)C]

The product from example 1 (15 mg) was dissolved in a mixture of DMF:DCM, 1:1 (5 mL) and N,N-dimethylglycyl chloride hydrochloride salt (8 mg) and Et$_3$N (0.01 mL) were added. The reaction mixture was stirred for 72 h. More N,N-dimethylglycyl chloride hydrochloride salt (0.050 g) and Et$_3$N (0.06 mL) were added, the mixture was stirred for a further 16 h. The product was purified via RPHPLC.
$^1$H NMR δ (CD$_3$OD) 8.05-7.96 (1H, m), 7.73-7.66 (1H, m), 7.54-7.45 (1H, m), 7.38-7.29 (1H, m), 7.17-7.01 (4H, m), 4.63-4.45 (4H, m), 3.63 (3H, s), 3.56 (2H, s), 3.51-3.33 (2H, m), 3.01 (1H, s), 2.94-2.85 (2H, m), 2.28 (3H, s), 2.22-2.13 (1H, m), 2.04 (4H, s), 1.88-1.78 (2H, m), 1.52-1.42 (2H, m), 1.35-1.25 (1H, m), 1.00 (3H, s)
MS: APCI (+ve): 545

Example 4

Methyl 2-(3-((N-(3-(4-amino-2-butyl-1H-imidazo[4,5-c]quinolin-1-yl)propyl)-2-(dimethylamino)acetamido)methyl)phenyl)acetate

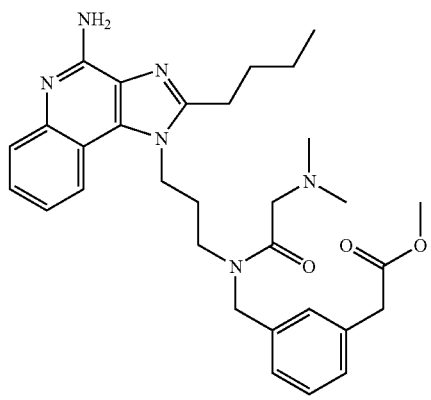 [SMILES: CCCCc1nc2c(N)nc3ccccc3c2n1CCCN(Cc1cccc(CC(=O)OC)c1)C(=O)CN(C)C]

The title compound was prepared by the method of example 3 using the product from example 2 (27 mg) to afford the title compound 3 mg as a colourless gum.

$^1$H NMR δ (CD$_3$OD) 8.04-7.95 (1H, m), 7.73-7.65 (1H, m), 7.53-7.44 (1H, m), 7.37-7.30 (1H, m), 7.20-7.13 (1H, m), 7.11-6.98 (3H, m), 4.62 (1H, s), 4.57-4.44 (3H, m), 3.63-3.55 (2H, m), 3.55-3.39 (3H, m), 3.26 (1H, s), 3.01 (1H, s), 2.94-2.83 (2H, m), 2.28 (3H, s), 2.22-2.11 (1H, m), 2.07-1.95 (4H, m), 1.88-1.77 (2H, m), 1.52-1.41 (2H, m), 1.35-1.24 (2H, m), 1.02-0.91 (3H, m)

MS: APCI (+ve): 545

Example 5

Methyl 2-(3-((4-((4-amino-2-(2-methoxyethyl)-1H-imidazo[4,5-c]quinolin-1-yl)methyl)piperidin-1-yl)methyl)phenyl)acetate di-trifluoroacetate salt

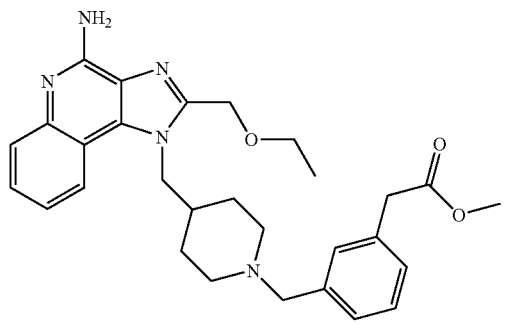 [SMILES: CCOCc1nc2c(N)nc3ccccc3c2n1CC1CCN(Cc2cccc(CC(=O)OC)c2)CC1]

(i) 2-(Ethoxymethyl)-1-(piperidin-4-ylmethyl)-1H-imidazo[4,5-c]quinolin-4-amine, di-trifluoroacetate salt The subtitle compound was prepared by the method of example 1 steps (i)-(vii) using tert-butyl 4-(aminomethyl)piperidine-1-carboxylate and ethoxyacetyl chloride.

MS: APCI (+ve): 340

(ii) Methyl 2-(3-((4-((4-amino-2-(2-methoxyethyl)-1H-imidazo[4,5-c]quinolin-1-yl)methyl)piperidin-1-yl)methyl)phenyl)acetate di-trifluoroacetate salt A mixture of the product from step (i) (0.14 g), methyl[3-(bromomethyl)phenyl]acetate (0.07 g) and K$_2$CO$_3$ (0.25 g) in DMF (5 mL) were stirred at rt for 18 h. The mixture was filtered then purified by RPHPLC. The product was dissolved in methanol/TFA mixture (4 mL 10/1), the solvent evaporated under reduced pressure and the residue triturated with diethylether, yield 25 mg.

$^1$H NMR δ (DMSO-d$_6$) 14.06 (1H, brs); 9.69 (1H, brs); 8.25 (1H, d); 7.83 (1H, d); 7.75 (1H, t); 7.58 (1H, t); 7.44-7.34 (4H, m); 4.79 (2H, s); 4.65 (2H, s); 4.21 (2H, s); 3.70 (2H, s); 3.63-3.55 (5H, m); 3.33 (2H, d); 2.90-2.75 (2H, m); 2.18 (1H, brs); 1.79-1.62 (4H, m); 1.18 (3H, t)

MS: APCI (+ve): 502

Example 6

Methyl[4-({[3-(4-amino-2-butyl-1H-imidazo[4,5-c]quinolin-1-yl)propyl][2-(dimethylamino)ethyl]amino}methyl)phenyl]acetate

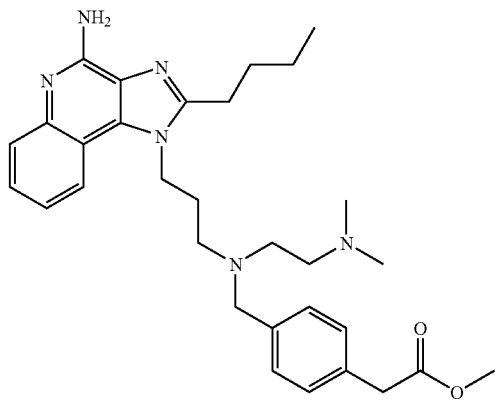 [SMILES: CCCCc1nc2c(N)nc3ccccc3c2n1CCCN(CCN(C)C)Cc1ccc(CC(=O)OC)cc1]

(i) N-(3-{[tert-Butyl(dimethyl)silyl]oxy}propyl)-3-nitroquinolin-4-amine

To a stirred solution of 3-nitro-quinolin-4-ol (5 g) in DCM (70 mL) was added DMF (2.3 mL) then thionyl chloride (2.1 mL) and the reaction mixture was refluxed for 3 h. The solution was cooled to 0° C. and 3-{[tert-butyl(dimethyl)silyl]oxy}propan-1-amine (6 g) was added followed by dropwise addition of Et$_3$N (12 mL). The reaction mixture was stirred at rt for 2 h, then partitioned between DCM and saturated NaHCO$_3$ solution. The organic layer was washed with water, dried, and the solvent evaporated under reduced pressure. The residue was triturated with iso-hexane to leave the subtitle compound (8.7 g).

MS: ESI (+ve): 362

(ii) N$^4$-(3-{[tert-Butyl(dimethyl)silyl]oxy}propyl)quinoline-3,4-diamine

A mixture of the product from step (i) (8.5 g), iron powder (14 g) in acetic acid was stirred at rt for 3 h the partitioned between EtOAc/water. The organics were separated, washed with saturated NaHCO$_3$ solution, brine, dried and evaporated under reduced pressure, yield 4.85 g.

MS: ESI (+ve): 332

(iii) 3-(2-Butyl-1H-imidazo[4,5-c]quinolin-1-yl)propyl pentanoate

Valeryl chloride was added to a solution of the product from step (ii) (4.85 g) in NMP at rt. The mixture was stirred at rt for 15 min, heated at 100° C. for 6 h, cooled, and partitioned between EtOAc/saturated NaHCO$_3$ solution. The organics were separated washed with water, dried and evaporated under reduced pressure. The residue was purified by chromatography on silica eluting with EtOAc, yield 2.15 g.

MS: ESI (+ve): 368

(iv) 3-(2-Butyl-5-oxido-1H-imidazo[4,5-c]quinolin-1-yl)propyl pentanoate

3-Chloroperoxybenzoic acid (1.6 g) was added to a solution of the product from step (iii) (2.15 g) in DCM (30 mL) at 5° C. The reaction mixture was allowed to warm to rt, stirred for 18 h and partitioned between DCM/saturated sodium bisulfate solution. The organics were separated washed with saturated NaHCO$_3$ solution, water, dried and evaporated under reduced pressure. Yield 1.77 g MS: ESI (+ve): 384

(v) 3-(4-Amino-2-butyl-1H-imidazo[4,5-c]quinolin-1-yl)propan-1-ol p-Toluenesulphonyl chloride (0.93 g) was added portionwise to a vigourously stirred mixture of the product from step (iv) (1.77 g) in DCM (50 mL) and ammonium hydroxide solution (35%, 5 mL) at rt. The reaction mixture was stirred for 3 h then partitioned between water/DCM. The organics were washed with saturated NaHCO$_3$ solution, water, dried, and the solvent evaporated under reduced pressure. The residue was dissolved in MeOH (40 mL), water (20 mL) then 6M NaOH solution (2 mL) added and the mixture stirred at rt for 18 h. The solid formed was filtered off washed with water and dried, yield 965 mg.

MS: ESI (+ve): 299

(vi) N'-[3-(4-Amino-2-butyl-1H-imidazo[4,5-c]quinolin-1-yl)propyl]-N,N-dimethylethane-1,2-diamine A mixture of the product from step (v) (0.96 g) and thionyl chloride (10 mL) in DCM (20 mL) was heated under reflux for 6 h then evaporated under reduced pressure. The residue was dissolved in acetonitrile (20 mL) then N,N-dimethylethylenediamine (10 mL) added and the mixture heated under reflux for 24 h. The solvent was removed under reduced pressure and the residue purified by RPHPLC, yield 0.512 g.

MS: APCI (+ve): 369

(vii) Methyl[4-({[3-(4-amino-2-butyl-1H-imidazo[4,5-c]quinolin-1-yl)propyl][2-(dimethylamino)ethyl]amino}methyl)phenyl]acetate A mixture of the product from step (vi) (0.25 g), methyl (4-formylphenyl)acetate (0.15 g) and sodium triacetoxyborohydride (0.2 g) in NMP (10 mL) was stirred at rt for 18 h then heated at 45° C. for 3 h. A further portion of methyl(4-formylphenyl)acetate (0.1 g) and sodium triacetoxyborohydride (0.2 g) were added then stirred at 45° C. for 6 h. The mixture was purified by RPHPLC, yield 0.035 g.

$^1$H NMR δ (DMSO-d$_6$) 8.02 (1H, d); 7.62 (1H, d); 7.40 (1H, t); 7.28 (2H, d); 7.21 (2H, d); 7.13 (1H, t); 6.47 (2H, s); 4.49-4.45 (2H, m); 3.66 (2H, s); 3.60 (2H, s); 3.59 (2H, s); 2.89 (2H, t); 2.61 (2H, t); 2.35 (2H, t); 2.07 (6H, s); 1.96-1.90 (2H, m); 1.82-1.74 (2H, m); 1.47-1.38 (2H, m); 0.94 (3H, t)

MS: APCI (+ve): 531

Example 7

Methyl 2-(3-((N-(3-(4-amino-2-(ethoxymethyl)-1H-imidazo[4,5-c]quinolin-1-yl)propyl)-2-(dimethylamino)acetamido)methyl)phenyl)acetate

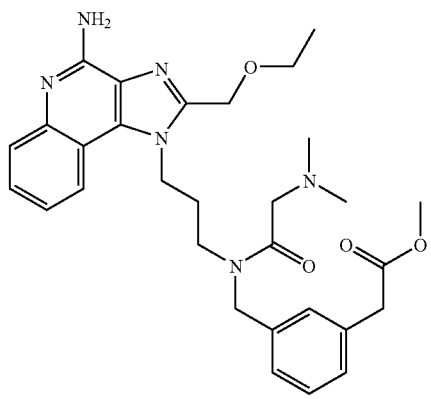 [SMILES: CCOCc1nc2c(N)nc3ccccc3c2n1CCCN(Cc1cccc(CC(=O)OC)c1)C(=O)CN(C)C]

(i) tert-Butyl[3-(2-ethoxymethyl-1H-imidazo[4,5-c]quinolin-1-yl)propyl]carbamate The product from example 1 step (iii) (790 mg) was dissolved in NMP (5 mL), then EDCI (1.44 g), HOBt (1 g), methoxyacetic acid (0.71 mL) and Et$_3$N (1 mL) were added. The mixture was stirred at 40° C. for 15 h then heated at 60° C. for 5 h. After cooling to rt, the crude mixture was dissolved in diethyl ether, washed with brine, dried and evaporated under reduced pressure, which afforded 600 mg of the subtitle product.

MS APCI+ve: 385

(ii) tert-Butyl[3-(2-ethoxymethyl-5-oxido-1H-imidazo[4,5-c]quinolin-1-yl)propyl]carbamate The subtitle compound was prepared by the method of example 1 step (v) using the product from step (i).
MS APCI+ve: 401

(iii) tert-Butyl[3-(4-amino-2-ethoxymethyl-1H-imidazo[4,5-c]quinolin-1-yl)propyl]carbamate The subtitle compound was prepared by the method of example 1 step (vi) using the product from step (ii).
MS APCI+ve: 400

(iv) 1-(3-Aminopropyl)-2-(ethoxymethyl)-1H-imidazo[4,5-c]quinolin-4-amine

The subtitle compound was prepared by the method of example 1 step (vii) using the product from step (iii)
MS APCI+ve: 300

(v) Methyl 2-(3-((3-(4-amino-2-(ethoxymethyl)-1H-imidazo[4,5-c]quinolin-1-yl)propylamino)methyl)phenyl)acetate Methyl 2-(3-formylphenyl)acetate (199 mg) was added to the product of step (iv) (334 mg) in THF (20 mL) at 25° C.

under nitrogen. The resulting solution was stirred at rt for 6 h. Sodium triacetoxyborohydride (1183 mg) was added to the reaction mixture at rt under nitrogen and the mixture was stirred at rt for 15 h. The reaction mixture was quenched with water and dissolved in MeOH. The product was purified via RPHPLC, which afforded 25 mg of the desired product as a white solid.

MS APCI+ve: 462

(vi) Methyl 2-(3-((N-(3-(4-amino-2-(ethoxymethyl)-1H-imidazo[4,5-c]quinolin-1-yl)propyl)-2-chloroacetamido)methyl)phenyl)acetate Chloroacetyl chloride (0.059 mL) was added to the product of step (v) (25 mg) in MeCN (2 mL) at rt under nitrogen. The resulting solution was stirred at rt for 2 h, then concentrated in vacuo and azeotroped with toluene, yield 30 mg.

MS APCI+ve: 538

(vii) Methyl(3-{[[3-(4-amino-2-ethoxymethyl-1H-imidazo[4,5-c]quinolin-1-yl)propyl](N,N-dimethylglycyl)amino]methyl}phenyl)acetate The product from step (vi) (30 mg) was dissolved in DMF (2 mL) then a solution of dimethylamine (2M in THF, 0.279 mL) was added at rt under nitrogen. The resulting solution was stirred at rt for 16 h. The mixture was purified by RPHPLC to give the title compound, yield 4.5 mg.

$^1$H NMR δ (CD$_3$OD) 8.05-7.95 (1H, m), 7.75-7.65 (1H, m), 7.50-7.44 (1H, m), 7.39-7.35 (1H, m), 7.20-7.15 (1H, m), 7.14-7.07 (3H, m), 4.87-4.57 (8H, m), 3.64-3.54 (6H, m), 3.33-3.05 (4H, m), 2.31-2.05 (7H, m), 1.26-1.00 (3H, m)

MS APCI+ve: 547

Example 8

Methyl 2-(3-(((3-(4-amino-2-butyl-1H-imidazo[4,5-c]quinolin-1-yl)propyl)(1-methylpiperidin-4-yl)amino)methyl)phenyl)acetate

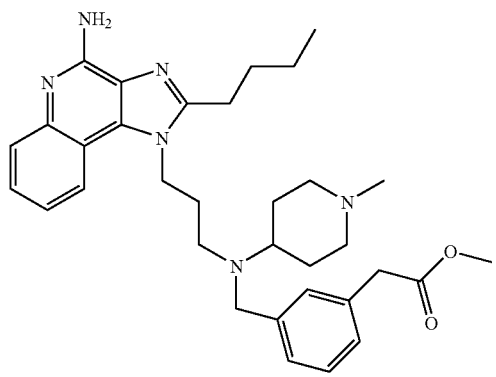 [SMILES: CCCCc1nc2c(N)nc3ccccc3c2n1CCCN(Cc1cccc(CC(=O)OC)c1)C1CCN(C)CC1]

(i) 2-Butyl-1-(3-(1-methylpiperidin-4-ylamino)propyl)-1H-imidazo[4,5-c]quinolin-4-amine Sodium triacetoxyborohydride (1.07 g) was added to a stirred mixture of the product from example 1 step (vii) (502 mg) and 1-methylpiperidin-4-one (0.21 mL) in NMP (2 mL) at rt. The resulting solution was stirred at 50° C. for 3 h, then purified by SCX, yield 335 mg.

MS: APCI (+ve): 395

(ii) Methyl 2-(3-(((3-(4-amino-2-butyl-1H-imidazo[4,5-c]quinolin-1-yl)propyl)(1-methylpiperidin-4-yl)amino)methyl)phenyl)acetate A solution of methyl 2-(3-formylphenyl)acetate (0.15 g) dissolved in NMP (10 mL) was added to a stirred solution of the product from step (i) (0.36 g) in NMP (10 mL) at rt. Sodium triacetoxyborohydride (0.90 g) was added to the mixture, the temperature was increased to 50° C. and the reaction mixture stirred for 24 h. The resulting solution was dissolved in methanol (0.5 mL), acidified with acetic acid (0.5 mL) and purified by SCX. The crude product was further purified by RPHPLC to give the title product, yield 22 mg.

$^1$H NMR δ (DMSO-d$_6$) 7.95 (1H, d); 7.59 (1H, d); 7.38 (1H, m); 7.27-7.04 (5H, m); 6.41 (2H, brs); 4.34 (2H, m); 3.62 (3H, m); 3.50 (2H, s); 3.29 (3H, s); 2.90-2.65 (4H, m); 2.30-2.40 (4H, m); 1.85-1.24 (9H, m); 0.92 (3H, t)

MS: APCI (+ve): 557

Example 9

Methyl 2-(4-(((3-(4-amino-2-butyl-1H-imidazo[4,5-c]quinolin-1-yl)propyl)(1-methylpiperidin-4-yl)amino)methyl)phenyl)acetate

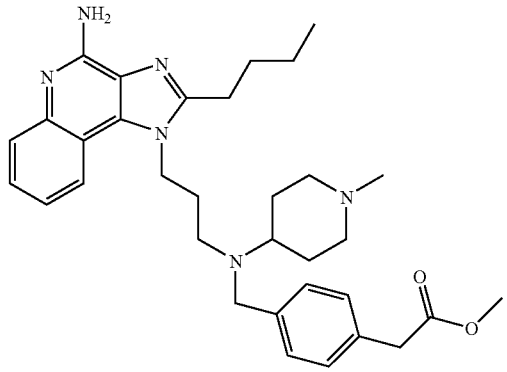 [SMILES: CCCCc1nc2c(N)nc3ccccc3c2n1CCCN(Cc1ccc(CC(=O)OC)cc1)C1CCN(C)CC1]

(i) 2-(4-(((3-(4-Amino-2-butyl-1H-imidazo[4,5-c]quinolin-1-yl)propyl)(1-methylpiperidin-4-yl)amino)methyl)phenyl)acetic acid A solution of 2-(4-formylphenyl)acetic acid (0.14 g) dissolved in NMP (10 mL) was added to a stirred solution of the product from example 8 step (i) (0.34 g) in NMP (10 mL) at rt. Sodium triacetoxyborohydride (0.90 g) was added and the mixture heated at 50° C. for 24 h. The resulting solution was dissolved in methanol (0.5 mL), acidified with acetic acid (0.5 mL) and and purified by SCX. The crude product was further purified by RPHPLC to give the subtitle product, yield 0.25 g.

MS: APCI (+ve): 543

(ii) Methyl 2-(4-(((3-(4-amino-2-butyl-1H-imidazo[4,5-c]quinolin-1-yl)propyl)(1-methylpiperidin-4-yl)amino)methyl)phenyl)acetate Sulfuric acid (1 mL) was added to the product from step (i) (250 mg) in MeOH (10 mL). The mixture was stirred at rt for 15 h, then the solvent evaporated under reduced pressure. The residue was purified by RPHPLC to afford the title compound, yield 6.2 mg.

¹H NMR δ (CD₃OD) 8.05 (1H, d); 7.72 (1H, d); 7.45 (1H, m); 7.25-7.20 (5H, m); 3.70-3.62 (5H, m); 3.35-2.70 (8H, m); 2.29 (3H, s); 2.15-1.24 (13H, m); 0.92 (3H, t)

MS: APCI (+ve): 557

Example 10

Methyl 2-(4-((N-(3-(4-amino-2-butyl-1H-imidazo[4,5-c]quinolin-1-yl)propyl)-2-(4-methylpiperazin-1-yl)acetamido)methyl)phenyl)acetate

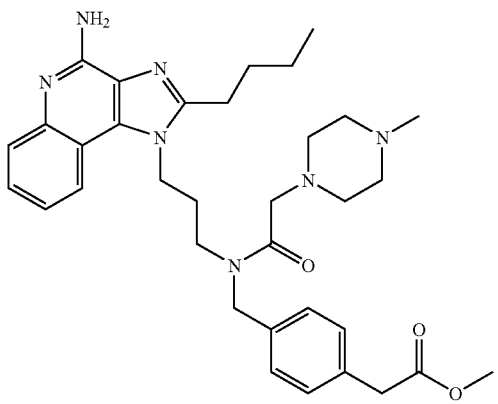 [SMILES: CCCCc1nc2c(N)nc3ccccc3c2n1CCCN(Cc1ccc(CC(=O)OC)cc1)C(=O)CN1CCN(C)CC1]

The title compound was prepared by the method of example 7 steps (vi)-(vii) using the product from example 1 and methyl piperazine.

¹H NMR δ (DMSO-d₆) 8.05 (1H, m), 7.65 (1H, m), 7.45 (1H, m), 7.15-7.05 (5H, m), 4.65-4.40 (7H, m), 3.71-3.60 (5H, m), 3.45-2.20 (15H, m), 2.00-1.25 (5H, m), 0.95 (3H, t)

MS: APCI (+ve): 600

Example 11

Methyl 2-(3-(((3-(4-amino-2-butyl-1H-imidazo[4,5-c]quinolin-1-yl)propyl)(3-(dimethylamino)propyl)amino)methyl)phenyl)acetate

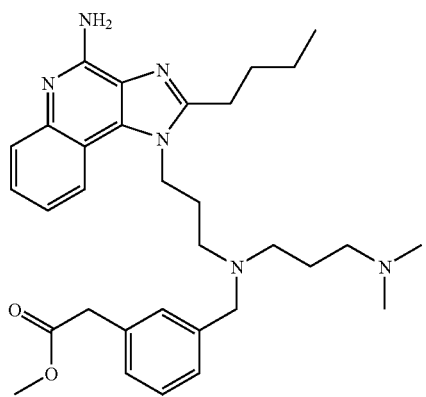 [SMILES: CCCCc1nc2c(N)nc3ccccc3c2n1CCCN(CCCN(C)C)Cc1cccc(CC(=O)OC)c1]

(i) 3-(3-Nitroquinolin-4-ylamino)propan-1-ol

Thionyl chloride (6.3 mL) was added to a mixture of 3-nitroquinolin-4-ol (15 g) and DMF (6.9 mL) in DCM (200 mL). The mixture was heated under reflux for 3 h then cooled to 0° C. 3-Amino-1-propanol (7.3 mL) was added slowly followed by dropwise addition of TEA (36 mL) and the mixture stirred at rt for 3 h. The precipitate was filtered, washed with DCM then water. The DCM filtrate was washed with water and evaporated under reduced pressure then combined with the filtered solid. The combined solids were triturated with ether and filtered to give a yellow solid, 19.2 g MS: APCI (+ve): 248

(ii) N-(3-(tert-Butyldimethylsilyloxy)propyl)-3-nitroquinolin-4-amine tert-Butyldimethylchlorosilane (18 g) was added to a mixture of the product from step (ii) (19.2 g) and imidazole (15 g) in DMF (200 mL). The mixture was stirred at rt for 16 h then partitioned between diethyl ether and water. The organics were separated, washed with water, dried, and evaporated under reduced pressure. The residue was triturated with isohexane and filtered to give 21.8 g of a yellow solid.

MS: APCI (+ve): 362

(iii) N⁴-(3-(tert-Butyldimethylsilyloxy)propyl)quinoline-3,4-diamine

Iron powder (10 g) was added to a solution of the product from step (ii) (20 g) in acetic acid (200 mL) and MeOH (100 mL). The mixture was stirred at rt for 30 min then evaporated under reduced pressure. The residue was partitioned between DCM and water, the organics separated, washed with aq NaHCO₃ solution, water, dried, and evaporated under reduced pressure. The residue was purified by chromatography on silica eluting with 3-5% MeOH in DCM to give a brown oil, 10.1 g.

MS: APCI (+ve): 332

(iv) 2-Butyl-1-(3-(tert-butyldimethylsilyloxy)propyl)-1H-imidazo[4,5-c]quinoline Pentanoyl chloride (3.7 mL) was added dropwise to a stirred solution of the product from step (iii) (10 g) and TEA (5 mL) in NMP (110 mL) at rt under nitrogen. The mixture was stirred at rt for 2 h then heated to 100° C. for 6 h. After cooling, the reaction mixture was partitioned between diethyl ether/water, the organics were separated, washed with water, dried, and evaporated under reduced pressure. The residue was purified by chromatography on silica eluting with 50-70% EtOAc/isohexane, yield 6.58 g.

1H NMR δ (CDCl₃) 9.29 (s, 1H); 8.34-8.26 (m, 2H); 7.69-7.58 (m, 2H); 4.68 (t, 2H); 3.78 (t, 2H); 3.00 (t, 2H); 2.20-2.11 (m, 2H); 2.00-1.90 (m, 2H); 1.59-1.47 (m, 2H); 1.02 (H, 3H); 0.99 (s, 9H); 0.14 (s, 6H)

(v) 2-Butyl-1-(3-(tert-butyldimethylsilyloxy)propyl)-1H-imidazo[4,5-c]quinolin-4-amine 3-Chloroperoxybenzoic acid (4 g) was added portionwise to a solution of the product from step (iv) (6.5 g) in DCM (100 mL) at 0-5° C. The mixture was warmed to rt, stirred for 3 h then partitioned between DCM and aq sodium metabisulphite solution. The organics were separated, washed with aq NaHCO₃ solution, water, dried, and evaporated under reduced pressure. The residue was dissolved in DCM (100mL) then 0.88 aq ammonia (12 mL) was added followed by p-toluenesulphonyl chloride (3.24 g) portionwise with vigorous stirring over 5 min. The mixture was stirred for 3 h then partitioned between DCM and water, the organics were separated, washed with aq NaHCO₃ solution, brine, dried, and evaporated under reduced pressure. Yield 6.7 g.
MS: APCI (+ve): 414

(vi) 3-(4-Amino-2-butyl-1H-imidazo[4,5-c]quinolin-1-yl)propan-1-ol, dihydrochloride 4M HCl in dioxane (12 mL) was added to a solution of the product from step (v) (6.7 g) in MeOH (100 mL) and stirred at rt for 18 h. The solvent was evaporated under reduced pressure, the residue triturated with diethyl ether, filtered and dried. Yield 5.53 g.
MS: APCI (+ve): 299

(vii) 3-(3-(4-Amino-2-butyl-1H-imidazo[4,5-c]quinolin-1-yl)propylamino)propan-1-ol A mixture of the product from step (vi) (5.53 g) and thionyl chloride (15 mL) in DCM (100 mL) was heated under reflux for 3 h then evaporated under reduced pressure. To the residue was added DMSO (10 mL), acetonitrile (80 mL) and 3-amino-1-propanol (25 mL) and the mixture heated under reflux for 4 h. The mixture was cooled and partitioned between water and EtOAc, the aqueous layer was extracted with EtOAc (4×400 mL), the organics were combined, dried, and evaporated under reduced pressure. The residue was triturated with ether and filtered, yield 4.21 g.
MS: APCI (+ve): 356

(viii) Methyl 2-(3-(((3-(4-amino-2-butyl-1H-imidazo[4,5-c]quinolin-1-yl)propyl)(3-hydroxypropyl)amino)methyl)phenyl)acetate A mixture of the product from step (vii) (2 g), methyl 2-(3-(bromomethyl)phenyl)acetate (1.4 g) and potassium carbonate (2.1 g) in DMF (20 mL) was stirred at rt under nitrogen for 24 h. The mixture was partitioned between DCM/water, the organics separated, washed with water, dried, and evaporated under reduced pressure. The residue was purified by chromotography on silica eluting with DCM/MeOH/Et₃N (1000/50/3). Yield 2.43 g of solid.
MS: APCI (+ve): 518

(ix) Methyl 2-(3-(((3-(4-amino-2-butyl-1H-imidazo[4,5-c]quinolin-1-yl)propyl)(3-chloropropyl)amino)methyl)phenyl)acetate A mixture of the product from step (viii) (2.43 g) and thionyl chloride (10 mL) in DCM (30 mL) was stirred at rt for 4 h then evaporated under reduced pressure to give the subtitle compound. Used crude in next step.
MS: APCI (+ve): 536/8

(x) Methyl 2-(3-(((3-(4-amino-2-butyl-1H-imidazo[4,5-c]quinolin-1-yl)propyl)(3-(dimethylamino)propyl)amino)methyl)phenyl)acetate A solution of dimethylamine in THF (2M, 6 mL) was added to a mixture of the product from step (ix) (1.17 mmol) and sodium iodide (250 mg) in DMF (5 mL) at rt. The mixture was heated at 55° C. in a sealed vessel for 24 h, cooled, filtered and the filtrate purifed by RPHPLC. The fractions containing the desired compound were evaporated to dryness and the residue triturated with ether/isohexane, 270 mg.
¹H NMR DMSO-d6: δ 8.00 (d, 1H); 7.60 (d, 1H); 7.38 (t, 1H); 7.29-7.21 (m, 3H); 7.15-7.09 (m, 2H); 6.42 (s, 2H); 4.46 (t, 1H); 3.64 (s, 2H); 3.58 (s, 2H); 3.54 (s, 3H); 2.89 (t, 2H); 2.58 (t, 2H); 2.42 (t, 2H); 2.16 (t, 2H); 2.05 (s, 6H); 1.96-1.91 (m, 2H); 1.81-1.73 (m, 2H); 1.63-1.56 (m, 2H); 1.46-1.37 (m, 2H); 0.93 (t, 3H).
MS: Multimode+: 545.

Example 12

Methyl 2-(3-(((3-(4-amino-2-butyl-1H-imidazo[4,5-c]quinolin-1-yl)propyl)(3-morpholinopropyl)amino)methyl)phenyl)acetate

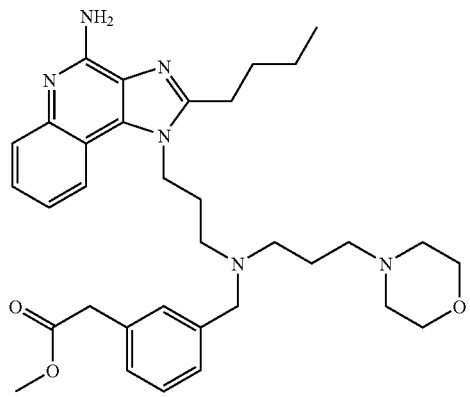 [SMILES: CCCCc1nc2c(N)nc3ccccc3c2n1CCCN(CCCN1CCOCC1)Cc1cccc(CC(=O)OC)c1]

The title compound was prepared by the method of example 11 step (x) using the product from example 11 step (ix) (627 mg) and morpholine (1 ml) to give product as a white solid 165 mg.
¹H NMR DMSO-d6: δ 8.01 (d, 1H); 7.60 (d, 1H); 7.39 (t, 1H); 7.27-7.12 (m, 5H); 6.46 (s, 2H); 4.47 (t, 2H); 3.64 (s, 2H); 3.57 (s, 2H); 3.55 (s, 3H); 3.47-3.45 (t, 4H); 2.89 (t, 2H); 2.58 (t, 2H); 2.42 (t, 2H); 2.23-2.19 (m, 6H); 1.99-1.91 (m, 2H); 1.81-1.74 (m, 2H); 1.63-1.56 (m, 2H); 1.46-1.37 (m, 2H); 0.93 (t, 3H).
MS: Multimode+: 587

Example 13

Methyl 2-(3-(((3-(4-amino-2-butyl-1H-imidazo[4,5-c]quinolin-1-yl)propyl)(3-(ethyl(methyl)amino)propyl)amino)methyl)phenyl)acetate

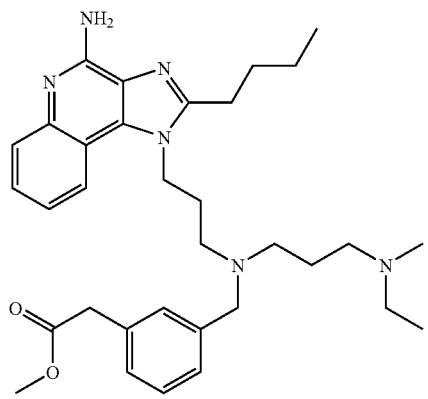 [SMILES: CCCCc1nc2c(N)nc3ccccc3c2n1CCCN(CCCN(C)CC)Cc1cccc(CC(=O)OC)c1]

The title compound was prepared by the method of example 11 step (x) using the product of example 11 step (ix) (627 mg) and N-ethylmethylamine (1 ml) as a white solid 65 mg.

¹H NMR DMSO-d6: δ 8.01 (d, 1H); 7.60 (d, 1H); 7.39 (t, 1H); 7.29-7.09 (m, 5H); 6.43 (s, 2H); 4.45 (t, 2H); 3.64 (s, 2H); 3.57 (s, 2H); 3.54 (s, 3H); 2.89 (t, 2H); 2.58 (t, 2H); 2.41 (t, 2H); 2.28-2.21 (m, 4H); 2.04 (s, 3H); 1.96-1.92 (m, 2H); 1.81-1.74 (m, 2H); 1.63-1.56 (m, 2H); 1.44-1.39 (m, 2H); 0.93 (t, 3H); 0.89 (t, 3H).
MS: Multimode+: 559

Example 14

Methyl 2-(3-(((3-(4-amino-2-butyl-1H-imidazo[4,5-c]quinolin-1-yl)propyl)(3-(4-methylpiperazin-1-yl)propyl)amino)methyl)phenyl)acetate

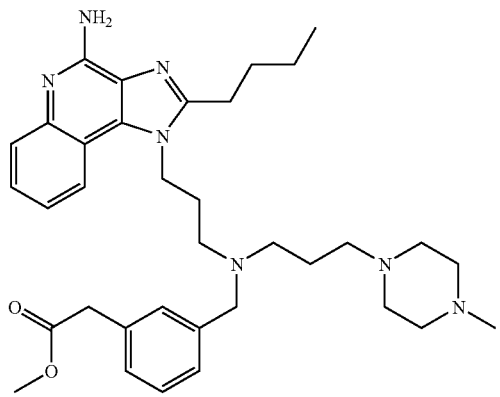 [SMILES: CCCCc1nc2c(N)nc3ccccc3c2n1CCCN(CCCN1CCN(C)CC1)Cc1cccc(CC(=O)OC)c1]

The title compound was prepared by the method of example 11step (x) using the product of example11 step (ix) (627 mg) and N-methylpiperazine (1 ml) as a colourless gum 120 mg.
¹H NMR DMSO-d6: δ 8.00 (d, 1H); 7.60 (d, 1H); 7.38 (t, 1H); 7.29-7.10 (m, 5H); 6.42 (s, 2H); 4.46 (t, 2H); 3.64 (s, 2H); 3.57 (s, 2H); 3.54 (s, 3H); 2.89 (t, 2H); 2.58 (t, 2H); 2.41 (t, 2H); 2.33-2.13 (brm, 10H); 2.08 (s, 3H); 1.98-1.90 (m, 2H); 1.81-1.73 (m, 2H); 1.63-1.55 (m, 2H); 1.46-1.37 (m, 2H); 0.94 (t, 3H).
MS: Multimode+: 600

Example 15

Methyl 2-(4-((N-(3-(4-amino-2-butyl-1H-imidazo[4,5-c]quinolin-1-yl)propyl)-2-(methylsulfonyl)acetamido)methyl)phenyl)acetate

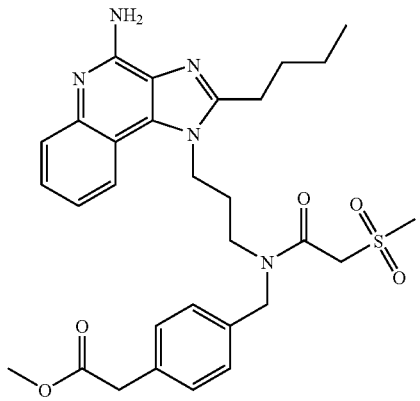

To a solution of the product from example 1 (221 mg) in DCM (10 mL) was added 2-(methylsulfonyl)acetic acid (66.4 mg) followed by TEA (0.201 mL) and HATU (201 mg). The reaction mixture was stirred at rt for 16 h then the solvents were evaporated. The crude product was purified by RPHPLC to afford the title compound (120 mg) as a white solid.

¹H NMR DMSO-d6: δ 8.07-7.93 (m, 1H), 7.66-7.56 (m, 1H), 7.47-7.37 (m, 1H), 7.29-7.04 (m, 5H), 6.43 (s, 2H), 4.71 (s, 1H), 4.59-4.37 (m, 5H), 3.67-3.55 (m, 5H), 3.15 (s, 3H), 2.93-2.80 (m, 2H), 2.72 (s, 1H), 2.10-1.93 (m, 2H), 1.84-1.68 (m, 2H), 1.49-1.32 (m, 2H), 1.30-1.19 (m, 1H), 0.95 (t, 3H)
MS: 580 ES+

Example 16

Methyl 2-(4-((N-(3-(4-amino-2-butyl-1H-imidazo[4,5-c]quinolin-1-yl)propyl)acetamido)methyl)phenyl)acetate

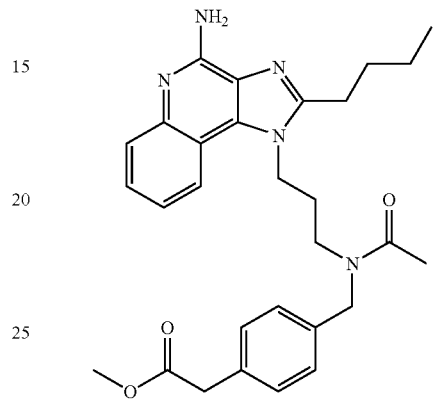

The product from example 1 (142 mg) was dissolved in DCM (5 mL) and TEA (0.065 mL) was added. The reaction mixture was cooled to 0° C. Acetyl chloride (0.029 mL) was added and the reaction mixture stirred for 30 min. The solvents were evaporated and the residue was taken up in MeOH and purified by RPHPLC to afford the title compound (40 mg) as a white solid.
¹H NMR DMSO-d6: δ 8.02-7.91 (m, 1H), 7.66-7.56 (m, 1H), 7.47-7.36 (m, 1H), 7.28-7.18 (m, 2H), 7.17-7.07 (m, 3H), 6.43 (d, 2H), 4.58 (s, 1H), 4.49-4.38 (m, 2H), 3.65 (s, 1H), 3.62-3.56 (m, 3H), 3.49-3.40 (m, 2H), 3.17 (d, 1H), 2.92-2.81 (m, 2H), 2.07 (d, 2H), 2.04-1.94 (m, 2H), 1.81-1.71 (m, 2H), 1.47-1.39 (m, 2H), 1.26-1.22 (m, 2H), 0.95 (t, 3H)
MS: 502 ES+

Example 17

Methyl 2-(4-((N-(3-(4-amino-2-butyl-1H-imidazo[4,5-c]quinolin-1-yl)propyl)-2-morpholinoacetamido)methyl)phenyl)acetate

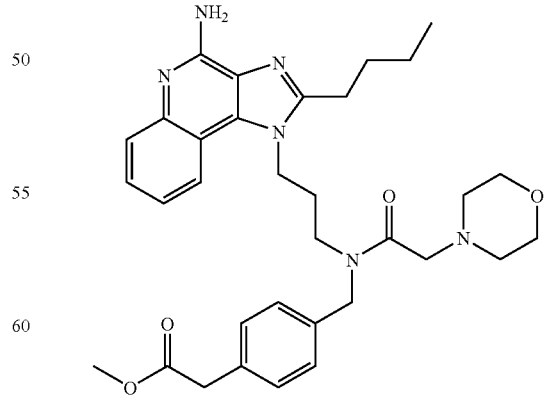

The title compound was prepared by the method of example 7 steps (vi)-(vii) using the product from example 1 (500 mg) and morpholine (0.9 ml), to give a yellow gum (102 mg).

¹H NMR DMSO-d6: δ 8.06-7.93 (m, 1H), 7.64-7.58 (m, 1H), 7.46-7.40 (m, 1H), 7.26-7.20 (m, 2H), 7.16 (d, 2H), 7.11-7.05 (m, 1H), 6.43 (d, 2H), 4.67 (s, 1H), 4.59-4.50 (m, 1H), 4.48-4.38 (m, 2H), 4.11-4.04 (m, 1H), 3.66-3.61 (m, 2H), 3.60 (s, 3H), 3.51-3.37 (m, 8H), 2.90-2.81 (m, 2H), 2.27-2.21 (m, 1H), 2.14-2.05 (m, 1H), 2.03-1.91 (m, 1H), 1.79-1.72 (m, 2H), 1.46-1.38 (m, 2H), 1.29-1.21 (m, 2H), 0.98-0.90 (m, 3H)

MS: 587 ES+

Example 18

Methyl 2-(4-((N-(3-(4-amino-2-butyl-1H-imidazo[4,5-c]quinolin-1-yl)propyl)-2-((2-ethoxyethyl)(methyl)amino)acetamido)methyl)phenyl)acetate

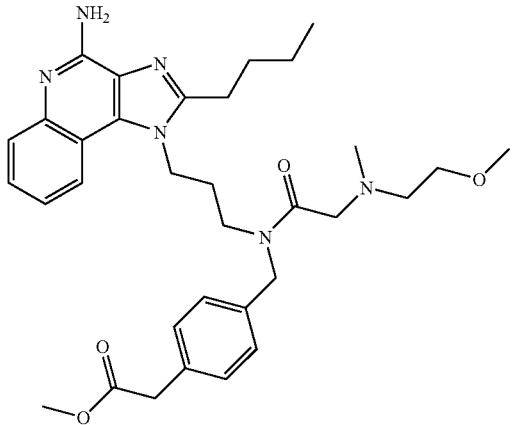 [SMILES: CCCCc1nc2c(N)nc3ccccc3c2n1CCCN(Cc1ccc(CC(=O)OC)cc1)C(=O)CN(C)CCOC]

The title compound was prepared by the method of example 7 steps (vi)-(vii) using the product from example 1 (500 mg) and N-(2-methoxyethyl)methylamine (0.97 mg), to give a yellow gum (62 mg).

¹H NMR DMSO-d6: δ 8.03-7.93 (m, 1H), 7.64-7.58 (m, 1H), 7.46-7.39 (m, 1H), 7.29-7.19 (m, 2H), 7.19-7.07 (m, 3H), 6.43 (s, 2H), 4.70 (s, 1H), 4.54-4.37 (m, 3H), 3.67-3.55 (m, 5H), 3.52-3.37 (m, 2H), 3.31-3.17 (m, 3H), 3.16-3.07 (m, 3H), 2.86 (td, 2H), 2.59-2.54 (m, 1H), 2.24 (s, 2H), 2.14-2.02 (m, 3H), 2.00-1.88 (m, 1H), 1.82-1.70 (m, 2H), 1.49-1.38 (m, 2H), 1.29-1.18 (m, 1H), 0.94 (t, 3H)

MS: 589 ES+

Example 19

Methyl 2-(4-((2-(4-acetylpiperazin-1-yl)-N-(3-(4-amino-2-butyl-1H-imidazo[4,5-c]quinolin-1-yl)propyl)acetamido)methyl)phenyl)acetate

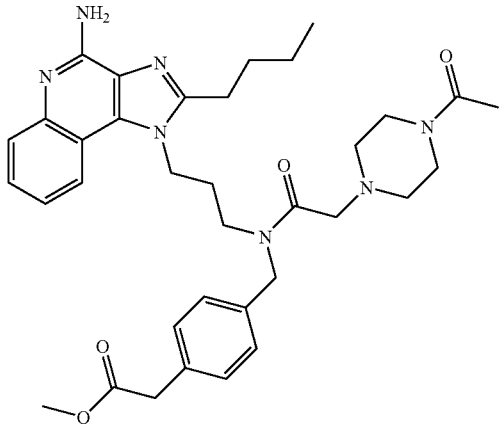 [SMILES: CCCCc1nc2c(N)nc3ccccc3c2n1CCCN(Cc1ccc(CC(=O)OC)cc1)C(=O)CN1CCN(C(C)=O)CC1]

The title compound was prepared by the method of example 7 steps (vi)-(vii) using the product from example 1 (500 mg) and 1-acetylpiperazine (1.2 g), to give a white solid (152 mg).

¹H NMR DMSO-d6: δ 8.06-7.92 (m, 1H), 7.64-7.57 (m, 1H), 7.46-7.39 (m, 1H), 7.28-7.13 (m, 4H), 7.12-7.04 (m, 1H), 6.48-6.40 (m, 2H), 4.69-4.61 (m, 1H), 4.59-4.52 (m, 1H), 4.49-4.38 (m, 2H), 3.66-3.62 (m, 2H), 3.60 (s, 3H), 3.49-3.38 (m, 2H), 3.28-3.23 (m, 4H), 2.91-2.81 (m, 2H), 2.70-2.61 (m, 2H), 2.45-2.33 (m, 2H), 2.23 (d, 2H), 1.98 (s, 3H), 1.77 (s, 2H), 1.43 (t, 2H), 0.94 (m, 3H)

MS: Multimode+: 628

Example 20

(R)-Methyl 2-(4-((N-(3-(4-amino-2-butyl-1H-imidazo[4,5-c]quinolin-1-yl)propyl)-2-(3-hydroxypyrrolidin-1-yl)acetamido)methyl)phenyl)acetate

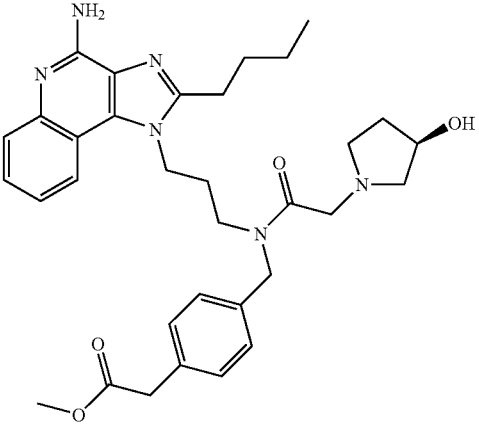 [SMILES: CCCCc1nc2c(N)nc3ccccc3c2n1CCCN(Cc1ccc(CC(=O)OC)cc1)C(=O)CN1CC[C@@H](O)C1]

The title compound was prepared by the method of example 7 steps (vi)-(vii) using the product from example 1 (500 mg) and R-(+)-pyrrolidin-3-ol (813 mg), to give a white solid (25 mg).

¹H NMR DMSO-d6: δ 8.02-7.93 (m, 1H), 7.64-7.59 (m, 1H), 7.46-7.39 (m, 1H), 7.27-7.19 (m, 2H), 7.18-7.14 (m, 2H), 7.12-7.08 (m, 1H), 6.46-6.41 (m, 2H), 4.69-4.64 (m, 1H), 4.55-4.50 (m, 1H), 4.45-4.39 (m, 2H), 3.62 (s, 3H), 3.50-3.35 (m, 2H), 3.25-3.13 (m, 4H), 2.89-2.83 (m, 2H), 2.79-2.77 (m, 1H), 2.70-2.64 (m, 1H), 2.42-2.24 (m, 2H), 2.10-2.01 (m, 2H), 1.99-1.90 (m, 2H), 1.82-1.73 (m, 2H), 1.56-1.35 (m, 3H), 0.98-0.91 (m, 3H)

MS: Multimode+: 587

Example 21

Methyl 2-(4-((N-(3-(4-amino-2-butyl-1H-imidazo[4,5-c]quinolin-1-yl)propyl)-2-(4-(pyrimidin-2-yl)piperazin-1-yl)acetamido)methyl)phenyl)acetate

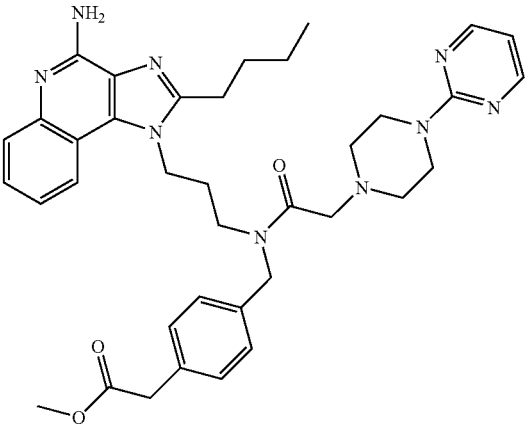 [SMILES: CCCCc1nc2c(N)nc3ccccc3c2n1CCCN(Cc1ccc(CC(=O)OC)cc1)C(=O)CN1CCN(c2ncccn2)CC1]

The title compound was prepared by the method of example 7 steps (vi)-(vii) using the product from example 1 (1.06 mg) and 2-(piperazin-1-yl)pyrimidine (0.32 mg) to give 40 mg as a white solid.

¹H NMR DMSO-d6: δ 8.34 (dd, 2H), 8.05-7.94 (m, 1H), 7.66-7.55 (m, 1H), 7.46-7.34 (m, 1H), 7.30-7.16 (m, 3H), 7.11-7.07 (m, 1H), 6.66-6.57(m, 1H), 6.50-6.41 (m, 2H), 4.74-4.66 (m, 1H), 4.61-4.52 (m, 1H), 4.50-4.39 (m, 2H), 3.66-3.50 (m, 3H), 3.53-3.30 (m, 6H), 3.27 (s, 3H), 3.13 (s, 2H), 2.86 (t, 2H), 2.39-2.28 (m, 2H), 2.18-2.08 (m, 1H), 2.04-1.94 (m, 3H), 1.82-1.72 (m, 2H), 1.47-1.35 (m, 2H), 1.29-1.18 (m, 1H), 0.99-0.85 (m, 3H)

MS: Multimode +: 664

Example 22

Ethyl 4-(2-((3-(4-amino-2-butyl-1H-imidazo[4,5-c]quinolin-1-yl)propyl)(4-(2-methoxy-2-oxoethyl)benzyl)amino)-2-oxoethyl)piperazine-1-carboxylate

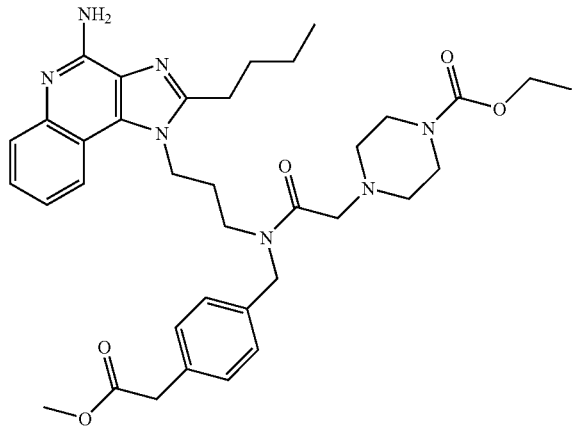 [SMILES: CCCCc1nc2c(N)nc3ccccc3c2n1CCCN(Cc1ccc(CC(=O)OC)cc1)C(=O)CN1CCN(C(=O)OCC)CC1]

The title compound was prepared by the method of example 7 steps (vi)-(vii) using the product from example 1 (230 mg) and ethyl piperazine-1-carboxylate (339 mg). The crude product was purified by RPHPLC and the resulting residue was triturated with a 1:1 mixture of ethyl aceate:ether to give the title compound as a white solid (74 mg).

¹H NMR DMSO-d6: δ 8.04-7.94 (m, 1H), 7.64-7.58 (m, 1H), 7.44-7.39 (m, 1H), 7.27-7.21 (m, 1H), 7.18-7.12 (m, 3H), 7.07 (d, 1H), 6.46-6.40 (m, 2H), 4.66 (s, 1H), 4.54 (s, 1H), 4.47-4.38 (m, 2H), 4.07-3.95 (m, 3H), 3.64-3.58 (m, 4H), 3.47-3.37 (m, 3H), 3.25-3.20 (m, 3H), 3.05-3.02 (m, 2H), 2.88-2.81 (m, 2H), 2.42-2.36 (m, 2H), 2.26-2.20 (m, 2H), 2.14-2.04 (m, 2H), 2.03-1.92 (m, 2H), 1.81-1.71 (m, 2H), 1.48-1.36 (m, 2H), 1.16 (dt, 3H), 0.94 (td, 3H)

MS: Multimode +: 658

Example 23

Methyl 2-(4-((N-(3-(4-amino-2-butyl-1H-imidazo[4,5-c]quinolin-1-yl)propyl)-2-(4-(ethylsulfonyl)piperazin-1-yl)acetamido)methyl)phenyl)acetate

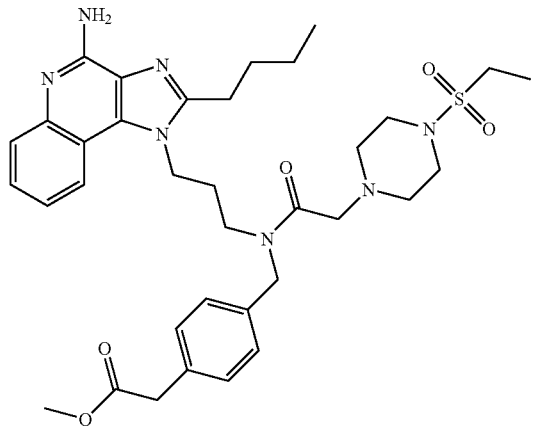 [SMILES: CCCCc1nc2c(N)nc3ccccc3c2n1CCCN(Cc1ccc(CC(=O)OC)cc1)C(=O)CN1CCN(S(=O)(=O)CC)CC1]

The title compound was prepared by the method of example 7 steps (vi)-(vii) using the product from example 1 (230 mg) and 1-(ethylsulfonyl)piperazine (382 mg). The crude product was purified as in example 22 to give the title compound as a white solid (72 mg).

¹H NMR DMSO-d6: δ 8.00 (dd, 1H), 7.64-7.55 (m, 1H), 7.47-7.38 (m, 1H), 7.31-7.22 (m, 1H), 7.21-7.12 (m, 3H), 7.13-7.04 (m, 1H), 6.51-6.39 (m, 2H), 4.69-4.60 (m, 1H), 4.61-4.52 (m, 1H), 4.47-4.38 (m, 2H), 3.68-3.56 (m, 5H), 3.48-3.38 (m, 2H), 3.28-3.23 (m, 2H), 3.11-3.00 (m, 4H), 2.99-2.91 (m, 4H), 2.89-2.82 (m, 2H), 2.36-2.30 (m, 3H), 2.15-1.92 (m, 2H), 1.81-1.73 (m, 2H), 1.46-1.38 (m, 2H), 1.20-1.12 (m, 3H), 0.98-0.90 (m, 3H)

MS: Multimode+: 678

Example 24

Methyl 2-(4-((N-(3-(4-amino-2-butyl-1H-imidazo[4,5-c]quinolin-1-yl)propyl)-2-(piperidin-1-yl)acetamido)methyl)phenyl)acetate

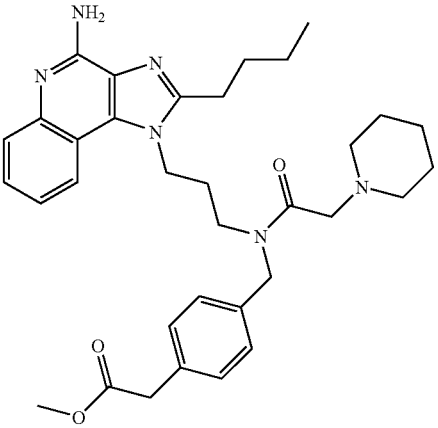 [SMILES: CCCCc1nc2c(N)nc3ccccc3c2n1CCCN(Cc1ccc(CC(=O)OC)cc1)C(=O)CN1CCCCC1]

The title compound was prepared by the method of example 7 steps (vi)-(vii) using the product from example 1 (230 mg) and piperidine (183 mg). The crude product was purified by RPHPLC and the resulting residue was triturated with ethyl acetate to give the title compound as a white solid (25 mg).

¹H NMR DMSO-d6: δ 8.03-7.92 (m, 1H), 7.60 (d, 1H), 7.45-7.40 (m, 1H), 7.26-7.20 (m, 2H), 7.19-7.14 (m, 2H), 7.11-7.03 (m, 1H), 6.45-6.40 (m, 1H), 4.72-4.66 (m, 1H), 4.57-4.51 (m, 1H), 4.48-4.37 (m, 2H), 3.65-3.58 (m, 5H), 3.53-3.35 (m, 2H), 3.14-3.08 (m, 2H), 2.97-2.91 (m, 2H), 2.90-2.78 (m, 3H), 2.38-2.30 (m, 2H), 2.16-1.87 (m, 2H), 1.84-1.72 (m, 3H), 1.49-1.19 (m, 8H), 0.94 (td, 3H).

MS: Multimode+: 585

Example 25

Methyl 2-(4-((N-(3-(4-amino-2-butyl-1H-imidazo[4,5-c]quinolin-1-yl)propyl)-2-(4-(tert-butoxycarbonylamino)piperidin-1-yl)acetamido)methyl)phenyl)acetate

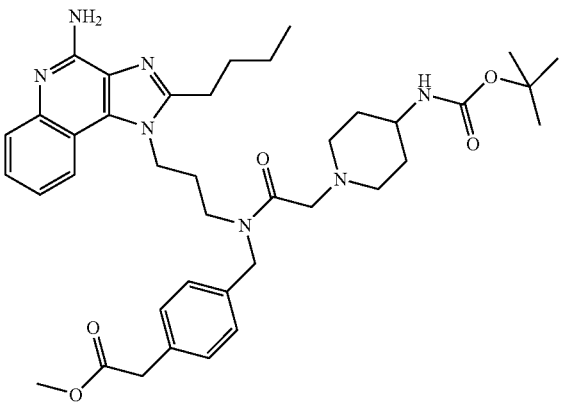 [SMILES: CCCCc1nc2c(N)nc3ccccc3c2n1CCCN(Cc1ccc(CC(=O)OC)cc1)C(=O)CN1CCC(NC(=O)OC(C)(C)C)CC1]

The title compound was prepared by the method of example 7 steps (vi)-(vii) using the product from example 1 (230 mg) and tent-butyl piperidin-4-ylcarbamate (430 mg). The crude product was purified by RPHPLC and the resulting residue was triturated with ethyl acetate to give the title compound as a white solid (87 mg).

¹H NMR DMSO-d6: δ 8.05-7.93 (m, 1H), 7.66-7.54 (m, 1H), 7.48-7.36 (m, 1H), 7.27-7.14 (m, 3H), 7.08-7.03 (m, 1H), 6.75-6.63 (m, 1H), 6.46-6.40 (m, 2H), 4.65-4.60 (m, 1H), 4.58-4.48 (m, 1H), 4.47-4.36 (m, 2H), 3.65-3.58 (m, 2H), 3.48-3.35 (m, 2H), 3.18-3.10 (m, 2H), 2.89-2.81 (m, 3H), 2.80-2.73 (m, 1H), 2.69-2.62 (m, 2H), 2.11-2.01 (m, 4H), 1.97-1.87 (m, 2H), 1.82-1.72 (m, 2H), 1.67-1.56 (m, 2H), 1.48-1.40 (m, 2H), 1.37 (t, 9H), 1.30-1.23 (m, 3H), 0.94 (t, 3H).

MS: Multimode+: 700

Example 26

Methyl 2-(4-((N-(3-(4-amino-2-butyl-1H-imidazo[4,5-c]quinolin-1-yl)propyl)-2-(4-(tert-butoxycarbonyl(methyl)amino)piperidin-1-yl)acetamido)methyl)phenyl)acetate

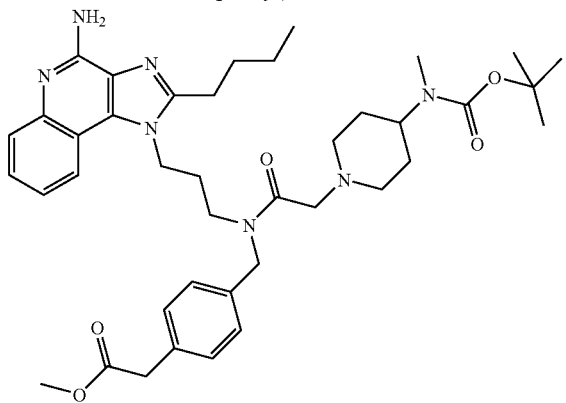

The title compound was prepared by the method of example 7 steps (vi)-(vii) using the product from example 1 (230 mg) and tent-butyl methyl(piperidin-4-yl)carbamate (440 mg). The crude product was purified by RPHPLC and the resulting residue was triturated with ethyl acetate to give the title compound as a white solid (40 mg).

¹H NMR DMSO-d6: δ 8.05-7.94 (m, 1H), 7.64-7.58 (m, 1H), 7.45-7.39 (m, 1H), 7.29-7.20 (m, 1H), 7.19-7.14 (m, 3H), 7.10-7.06 (m, 1H), 6.45-6.40 (m, 2H), 4.70-4.66 (m, 1H), 4.58-4.51 (m, 2H), 4.48-4.38 (m, 2H), 3.65 (s, 3H), 3.61 (s, 3H), 3.51-3.38 (m, 3H), 3.18-3.14 (m, 1H), 2.98-2.95 (m, 1H), 2.89-2.81 (m, 3H), 2.68-2.59 (m, 2H), 2.16-1.86 (m, 6H), 1.85-1.71 (m, 2H), 1.53-1.38 (m, 6H), 1.39-1.34 (m, 9H), 0.94 (td, 3H).

MS: Multimode+: 714

Example 27

Ethyl 2-(1-(2-((3-(4-amino-2-butyl-1H-imidazo[4,5-c]quinolin-1-yl)propyl)(4-(2-methoxy-2-oxoethyl)benzyl)amino)-2-oxoethyl)piperidin-4-yl)acetate

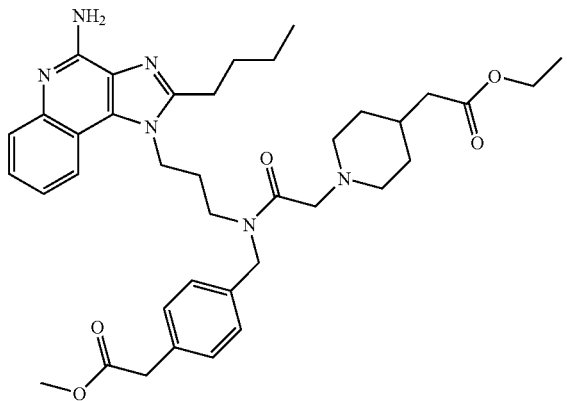 [SMILES: CCCCc1nc2c(N)nc3ccccc3c2n1CCCN(Cc1ccc(CC(=O)OC)cc1)C(=O)CN1CCC(CC(=O)OCC)CC1]

The title compound was prepared by the method of example 7 steps (vi)-(vii) using the product from example 1 (230 mg) and ethyl 2-(piperidin-4-yl)acetate (75 mg). The crude product was purified by RPHPLC and the resulting residue was triturated with ethyl acetate to give the title compound as a white solid (25 mg).

¹H NMR DMSO-d6: δ 8.03-7.92 (m, 1H), 7.64-7.58 (m, 1H), 7.42 (s, 1H), 7.27-7.20 (m, 1H), 7.18-7.14 (m, 3H), 7.09-7.05 (m, 1H), 6.44-6.40 (m, 2H), 4.69-4.64 (m, 1H), 4.56-4.50 (m, 1H), 4.46-4.38 (m, 2H), 4.03 (q, 2H), 3.65-3.62 (m, 2H), 3.61-3.59 (m, 3H), 3.50-3.38 (m, 2H), 3.14 (s, 1H), 2.97 (s, 1H), 2.88-2.82 (m, 2H), 2.80-2.75 (m, 2H), 2.16-2.06 (m, 3H), 2.04-1.91 (m, 3H), 1.89-1.72 (m, 3H), 1.60-1.47 (m, 3H), 1.46-1.38 (m, 2H), 1.20-1.12 (m, 4H), 1.12-1.07 (m, 2H), 0.94 (td, 3H).

MS: Multimode+: 671

Example 28

Methyl 1-(2-((3-(4-amino-2-butyl-1H-imidazo[4,5-c]quinolin-1-yl)propyl)(4-(2-methoxy-2-oxoethyl)benzyl)amino)-2-oxoethyl)piperidine-4-carboxylate

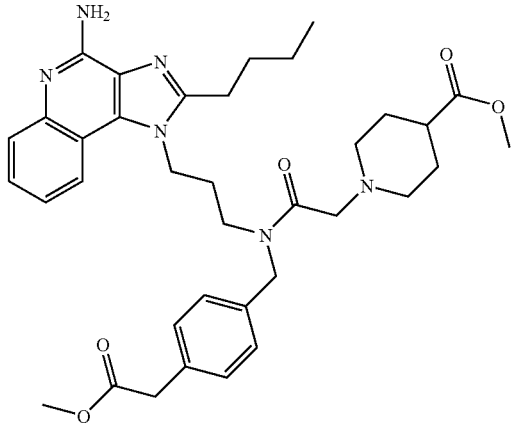 [SMILES: CCCCc1nc2c(N)nc3ccccc3c2n1CCCN(Cc1ccc(CC(=O)OC)cc1)C(=O)CN1CCC(C(=O)OC)CC1]

The title compound was prepared by the method of example 7 steps (vi)-(vii) using the product from example 1 (230 mg) and methyl piperidine-4-carboxylate (61 mg). The crude product was purified by RPHPLC and the resulting residue was triturated with diethyl ether to give the title compound as a white solid (16 mg).

¹H NMR DMSO-d6: δ 8.02-7.92 (m, 1H), 7.64-7.58 (m, 1H), 7.45-7.39 (m, 1H), 7.26-7.20 (m, 2H), 7.18-7.14 (m, 2H), 7.07-7.05 (m, 1H), 6.44-6.40 (m, 2H), 4.69-4.66 (m, 1H), 4.56-4.51 (m, 1H), 4.46-4.39 (m, 2H), 3.64-3.62 (m, 2H), 3.60-3.58 (m, 3H), 3.48-3.37 (m, 2H), 3.29-3.28 (m, 3H), 3.17-3.10 (m, 1H), 3.00-2.93 (m, 1H), 2.89-2.82 (m, 2H), 2.80-2.74 (m, 2H), 2.63-2.58 (m, 2H), 2.29-2.18 (m, 1H), 2.14-1.89 (m, 4H), 1.82-1.69 (m, 4H), 1.54-1.37 (m, 4H), 0.94 (td, 3H).

MS: Multimode+: 643

Example 29

Methyl 2-(4-((N-(3-(4-amino-2-(2-methoxyethyl)-1H-imidazo[4,5-c]quinolin-1-yl)propyl)-2-(piperidin-1-yl)acetamido)methyl)phenyl)acetate

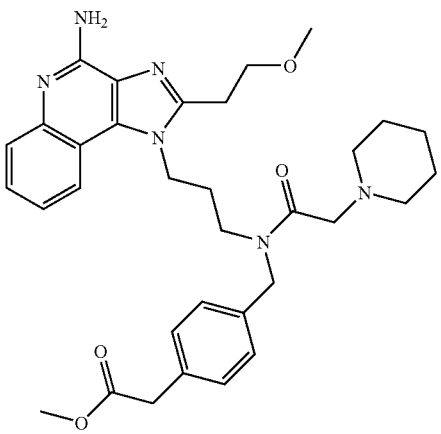

i) tert-Butyl 3-(2-(2-methoxyethyl)-1H-imidazo[4,5-c]quinolin-1-yl)propylcarbamate To the product of example 1 step (iii) (1.9 g) in NMP (25 mL), 3-methoxypropanoic acid (0.678 mL, 7.21 mmol) was added followed by HATU (2.74 g) and TEA (0.837 mL) under nitrogen. The resulting solution was stirred at 60° C. for 15 h. The reaction mixture was diluted with diethyl ether (300 mL) and EtOAc (300 mL), and washed with water (300 mL), sat. NaHCO₃ (200 mL), and saturated brine (200 mL). The organic was dried, filtered and evaporated to afford the subtitle product (3.5 g).
MS APCI+ve 385 ii) 1-(3-(tert-Butoxycarbonylamino)propyl)-2-(2-methoxyethyl)-1H-imidazo[4,5-c]quinoline 5-oxide The subtitle compound was prepared by the method of example 1 step (v) using the product from step (i).
MS APCI+ve: 401 iii) tert-Butyl 3-(4-amino-2-(2-methoxyethyl)-1H-imidazo[4,5-c]quinolin-1-yl)propylcarbamate The subtitle compound was prepared by the method of example 1 step (vi) using the product from step (ii).
MS APCI+ve: 400 iv) 1-(3-Aminopropyl)-2-(2-methoxyethyl)-1H-imidazo[4,5-c]quinolin-4-amine

The subtitle compound was prepared by the method of example 1 step (vii) using the product of step (iii).
MS APCI+ve: 300 v) Methyl 2-(4-((3-(4-amino-2-(2-methoxyethyl)-1H-imidazo[4,5-c]quinolin-1-yl)propylamino)methyl)phenyl)acetate To the product from step (iv) (1.25 g) in THF (100 mL), methyl 2-(4-formylphenyl)acetate (0.818 g) was added followed by sodium triacetoxyborohydride (0.885 g) and acetic acid (3 drops) and stirred at rt for 16 h. The reaction was quenched with water, extracted with DCM washed with sat. NaHCO₃ (200 mL), dried and solvent removed. The resulting residue was dissolved in methanol and purified on SCX to give the subtitle compound (0.73 g).
MS APCI+ve 462 vi) Methyl 2-(4-((N-(3-(4-amino-2-(2-methoxyethyl)-1H-imidazo[4,5-c]quinolin-1-yl)propyl)-2-(piperidin-1-yl)acetamido)methyl)phenyl)acetate To the product from step (v) (180 mg) in MeCN (5 mL), 2-chloroacetyl chloride (44.0 mg) was added at 0° C. and stirred for 7 h. Piperidine (332 mg) was added and stirred at rt for 15 h. The solvent was removed and the crude product was purified by RPHPLC. The resulting residue was triturated with diethyl ether to afford the title compound as a white solid (22 mg).
$^1$H NMR DMSO-d6: δ 8.03-7.93 (m, 1H), 7.64-7.59 (m, 1H), 7.45-7.40 (m, 1H), 7.28-7.20 (m, 1H), 7.19-7.15 (m, 3H), 7.11-7.07 (m, 1H), 6.47-6.43 (m, 2H), 4.70 (s, 1H), 4.61-4.55 (m, 1H), 4.45 (d, 2H), 3.80 (q, 2H), 3.63 (d, 2H), 3.60 (d, 3H), 3.52-3.46 (m, 1H), 3.44-3.37 (m, 1H), 3.16-3.08 (m, 3H), 2.97 (s, 1H), 2.39-2.31 (m, 3H), 2.23-2.17 (m, 2H), 2.15-2.08 (m, 1H), 2.00-1.92 (m, 1H), 1.46-1.39 (m, 3H), 1.36-1.23 (m, 7H).
MS: Multimode+: 587

Example 30

Methyl 2-(4-((N-(3-(4-amino-2-(2-methoxyethyl)-1H-imidazo[4,5-c]quinolin-1-yl)propyl)-2-(dimethylamino)acetamido)methyl)phenyl)acetate

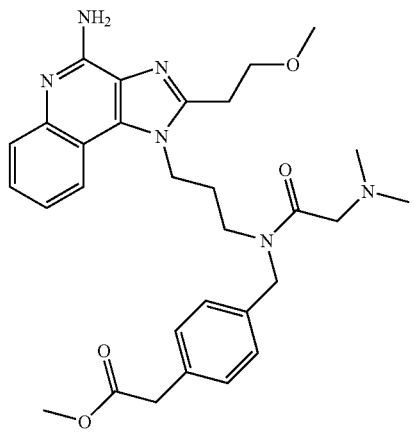 [SMILES: COCCc1nc2c(N)nc3ccccc3c2n1CCCN(Cc1ccc(CC(=O)OC)cc1)C(=O)CN(C)C]

The title compound was prepared by the method of example 29 step (vi) with the product of example 29 step (v) (180 mg) and a 2M THF solution of dimethylamine (0.2 ml). The title compound was obtained as a white solid (15 mg).
$^1$H NMR DMSO-d6: δ 8.04-7.94 (m, 1H), 7.65-7.59 (m, 1H), 7.46-7.40 (m, 1H), 7.27-7.20 (m, 2H), 7.19-7.09 (m, 3H), 6.48-6.42 (m, 2H), 4.70-4.67 (m, 1H), 4.58-4.52 (m, 1H), 4.48-4.42 (m, 2H), 3.84-3.77 (m, 2H), 3.65-3.62 (m, 2H), 3.61 (s, 3H), 3.49-3.38 (m, 2H), 3.28 (s, 3H), 3.17-3.09 (m, 3H), 3.01-2.98 (m, 1H), 2.21 (s, 3H), 2.15-2.07 (m, 2H), 2.02 (s, 3H), 1.98-1.94 (m, 2H).
MS:Multimode+: 547

Example 31

Methyl 2-(3-((N-(3-(4-amino-2-(2-methoxyethyl)-1H-imidazo[4,5-c]quinolin-1-yl)propyl)-2-(piperidin-1-yl)acetamido)methyl)phenyl)acetate saccharin salt

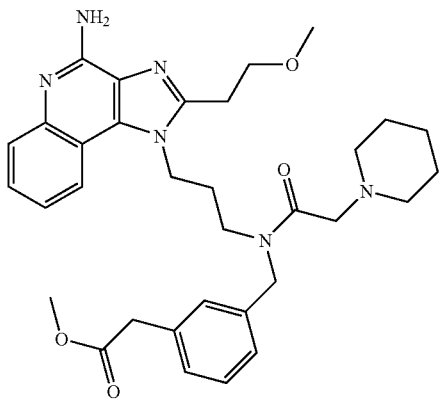 [SMILES: COCCc1nc2c(N)nc3ccccc3c2n1CCCN(Cc1cccc(CC(=O)OC)c1)C(=O)CN1CCCCC1]

i) Methyl 2-(3-((3-(4-amino-2-(2-methoxyethyl)-1H-imidazo[4,5-c]quinolin-1-yl)propylamino)methyl)phenyl)acetate The subtitle compound was prepared by the method of example 29 step (v) using methyl 2-(4-formylphenyl)acetate. The subtitle compound was obtained as a white solid.
MS APCI+ve 462 ii) Methyl 2-(3-((N-(3-(4-amino-2-(2-methoxyethyl)-1H-imidazo[4,5-c]quinolin-1-yl)propyl)-2-(piperidin-1-yl)acetamido)methyl)phenyl)acetate saccharin salt The title compound was prepared by the method of example 29 step (vi) using the product from step (i) (95 mg) and piperidine (18 mg). The crude product was purified by RPHPLC to give the free base as a gum 44 mg, which was dissolved in 1 ml of MeOH. A solution of saccharin (13.9 mg) in 1 ml of MeOH was added and evaporated to dryness, EtOAc(2 ml) was added and the suspension stirred at rt for 2 days. The solid was collected by filtration and dried to afford the title compound as a white solid (22 mg).
$^1$H NMR DMSO-d6: δ 8.17-8.13 (m, 1H), 7.85-7.83 (m, 1H), 7.70-7.06 (m, 10H), 4.64-4.55 (m, 6H), 4.31-4.10 (brm, 2H), 3.86-3.80 (m, 2H), 3.64 (s, 2H), 3.58 (s, 3H), 3.50-3.46 (m, 2H), 3.32-3.17 (m, 9H), 2.07-1.71 (m, 6H).
MS: Multimode+: 587

Example 32

Methyl 2-(4-((N-(3-(4-amino-2-(2-methoxyethyl)-1H-imidazo[4,5-c]quinolin-1-yl)propyl)-2-((2-methoxyethyl)(methyl)amino)acetamido)methyl)phenyl)acetate

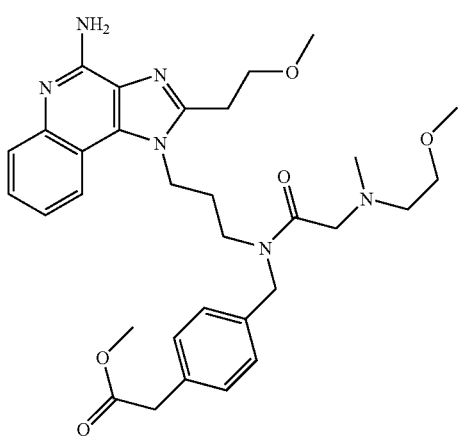 [SMILES: COCCc1nc2c(N)nc3ccccc3c2n1CCCN(Cc1ccc(CC(=O)OC)cc1)C(=O)CN(C)CCOC]

The title compound was prepared by the method of example 29 step (vi) using 2-methoxy-N-methylethanamine (455 mg) and the product of example 29 step (v) (549 mg). The title compound was obtained as a white solid (52 mg).
$^1$H NMR DMSO-d6: δ 8.03-7.96 (m, 1H), 7.64-7.61 (m, 1H), 7.44 (m, 1H), 7.28-7.10 (m, 5H), 6.46 (brs, 2H), 4.72-4.67 (m, 4H), 3.80 (q, 2H), 3.63 (m, 2H), 3.51 (s, 3H), 3.42-3.11 (m, 13H), 2.58-2.50 (m, 2H), 2.25-1.98 (m, 4H), 1.11 (t, 2H).
MS: Multimode+: 591

Example 33

Methyl 2-(4-((N-(3-(4-amino-2-(2-methoxyethyl)-1H-imidazo[4,5-c]quinolin-1-yl)propyl)-3-(piperidin-1-yl)propanamido)methyl)phenyl)acetate

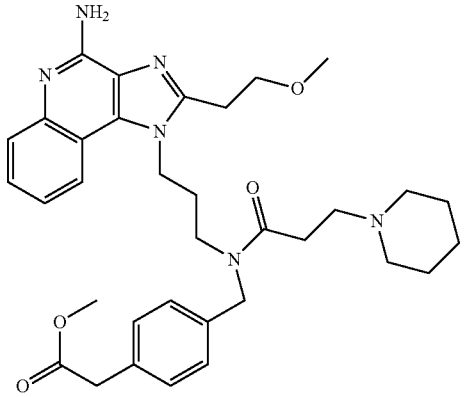 [SMILES: COCCc1nc2c(N)nc3ccccc3c2n1CCCN(Cc1ccc(CC(=O)OC)cc1)C(=O)CCN1CCCCC1]

To the product from step (v) of example 29 (480 mg, 1.04 mmol) in DMF (5 mL), 3-(piperidin-1-yl)propanoic acid (196 mg, 1.25 mmol) and HATU (475 mg, 1.25 mmol) were added at rt and stirred for 2 hours. After adding 1 mL of methanol, the crude product was purified by RPHPLC and the resulting residue was triturated with diethyl ether: EtOAc (5:1). The suspension was filtered to afford the title compound as a white solid (72 mg).
$^1$H NMR DMSO-d6: δ 8.03-7.96 (m, 1H), 7.63-7.60 (m, 1H), 7.45-7.40 (m, 1H), 7.28-7.10 (m, 5H), 6.46 (brs, 2H), 4.63-4.47 (m, 4H), 3.80 (t, 2H), 3.65-3.59 (m, 5H), 3.48 (m, 2H), 3.29-3.27 (m, 7H), 3.15 (q, 2H), 2.27-2.00 (m, 6H), 1.39-1.31 (m, 6H).
MS: Multimode+: 601

Example 34

Methyl 2-(4-(((3-(4-amino-2-(2-methoxyethyl)-1H-imidazo[4,5-c]quinolin-1-yl)propyl)(3-morpholinopropyl)amino)methyl)phenyl)acetate

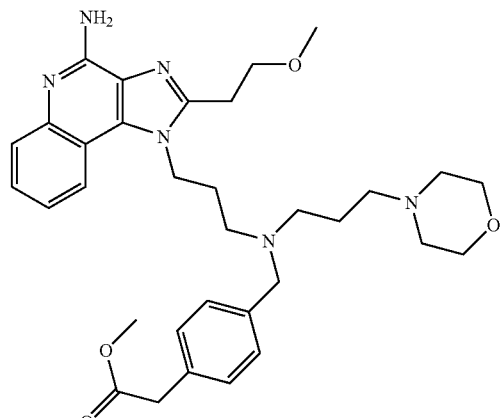

The product from step (v) of example 29 (360 mg, 0.78 mmol) was dissolved in MeCN (10 mL) and 4-(3-chloropropyl)morpholine hydrochloride (187 mg, 0.94 mmol) added at rt. Anhydrous K₂CO₃ (323 mg, 2.34 mmol) and sodium iodide (117 mg, 0.78 mmol) were added. The mixture was refluxed for 15 h. After cooling to room temperature, the crude product was purified by RPHPLC and the resulting residue was triturated with diethyl ether:EtOAc (5:1) at 0° C. The suspension was filtered to afford the title compound as a pale yellow solid (31 mg).

¹H NMR DMSO-d6: δ 8.03-8.00 (m, 1H), 7.61-7.58 (m, 1H), 7.42-7.37 (m, 1H), 7.29-7.26 (m, 2H), 7.19-7.14 (m, 2H), 7.14-7.09 (m, 1H), 6.45 (brs, 2H), 4.52 (m, 2H), 3.79 (t, 2H), 3.66-3.56 (m, 5H), 3.45 (m, 4H), 3.32-3.27 (m, 5H), 3.16 (t, 2H), 2.58-2.36 (m, 6H), 2.27-2.18 (m, 4H), 1.99-1.59 (m, 4H).

MS: Multimode+: 589.

Example 35

(S)-Methyl 2-(4-((N-(3-(4-amino-2-(2-methoxyethyl)-1H-imidazo[4,5-c]quinolin-1-yl)propyl)-2-(2-(methoxymethyl)pyrrolidin-1-yl)acetamido)methyl)phenyl)acetate disaccharin salt

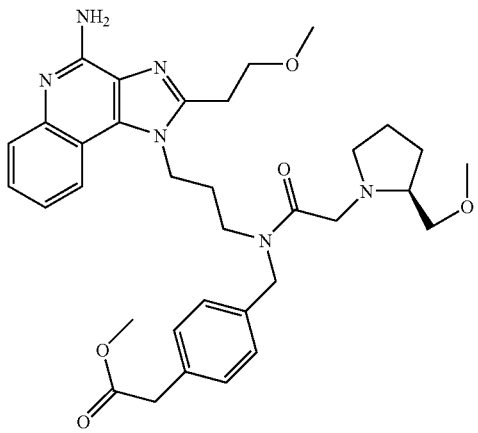 [SMILES: COCCc1nc2c(N)nc3ccccc3c2n1CCCN(Cc1ccc(CC(=O)OC)cc1)C(=O)CN1CCC[C@H]1COC]

The title compound was prepared by the method of example 29 step (vi) using (S)-2-(methoxymethyl)pyrrolidine (235 mg) and the product from example 29 step (v) (549 mg) to give the free base as a gum 97 mg. This was dissolved in MeOH (1 ml) and a solution of saccharin (59 mg) in MeOH (1 ml) was added and evaporated to dryness, diethyl ether (2 ml) was added and stirred at rt for 15 h. The solid was collected by filtration and to afford the title compound as a white solid 22 mg.

¹H NMR DMSO-d6: δ 8.17-8.22 (m, 1H), 7.88-7.85 (m, 1H), 7.74-7.56 (m, 10H), 7.26-7.13 (m, 4H), 4.64-4.55 (m, 6H), 4.31-4.10 (brm, 2H), 3.86-3.80 (m, 4H), 3.61-3.14 (m, 18H), 2.32-1.71 (m, 6H).

MS: Multimode+: 617

Example 36

(R)-Methyl 2-(4-((N-(3-(4-amino-2-(2-methoxyethyl)-1H-imidazo[4,5-c]quinolin-1-yl)propyl)-2-(2-(methoxymethyl)pyrrolidin-1-yl)acetamido)methyl)phenyl)acetate disaccharin salt

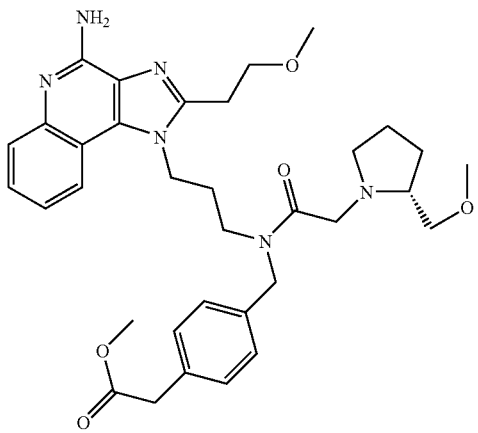 [SMILES: COCCc1nc2c(N)nc3ccccc3c2n1CCCN(Cc1ccc(CC(=O)OC)cc1)C(=O)CN1CCC[C@@H]1COC]

The title compound was prepared by the method of example 29 step (vi) using (S)-2-(methoxymethyl)pyrrolidine (117 mg) and the product from example 29 step (v) (549 mg) to give the free base as a gum. The dissaccharin salt was formed as in example 35 to give the title compound as a white solid 68 mg.

¹H NMR DMSO-d6: δ 8.17-8.22 (m, 1H), 7.88-7.85 (m, 1H), 7.74-7.56 (m, 10H), 7.26-7.13 (m, 4H), 4.64-4.55 (m, 6H), 3.86-3.80 (m, 4H), 3.61-3.14 (m, 18H), 2.42-1.71 (m, 6H).

MS: Multimode+: 617

Example 37

Methyl 2-(4-((N-(3-(4-amino-2-(2-methoxyethyl)-1H-imidazo[4,5-c]quinolin-1-yl)propyl)-2-(pyrrolidin-1-yl)acetamido)methyl)phenyl)acetate disaccharin salt

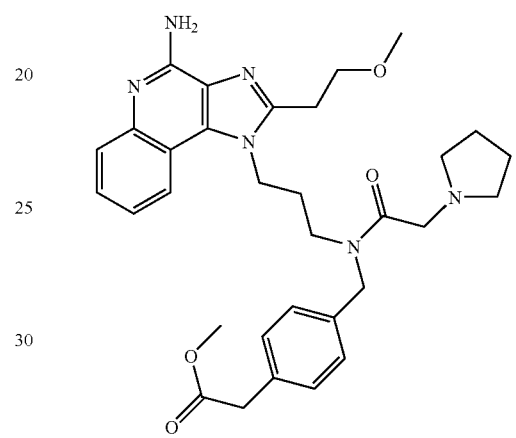

The title compound was prepared by the method of example 29 step (vi) using pyrrolidine (73 mg) and the product of example 29 step (v) (55 mg) to afford the free base as a gum.

The dissaccharin salt was formed as in example 35 to give the title compound as a white solid 29 mg.

¹H NMR DMSO-d6: δ 8.18-8.22 (m, 1H), 7.88-7.85 (m, 1H), 7.75-7.60 (m, 10H), 7.23-7.13 (m, 4H), 4.64-4.40 (m, 6H), 3.82 (m, 4H), 3.61-3.14 (m, 14H), 2.44-1.82 (m, 6H).

MS: Multimode+: 573

Example 38

Methyl 2-(4-((N-(3-(4-amino-2-(2-methoxyethyl)-1H-imidazo[4,5-c]quinolin-1-yl)propyl)-2-((2-hydroxyethyl)(methyl)amino)acetamido)methyl)phenyl)acetate disaccharin salt

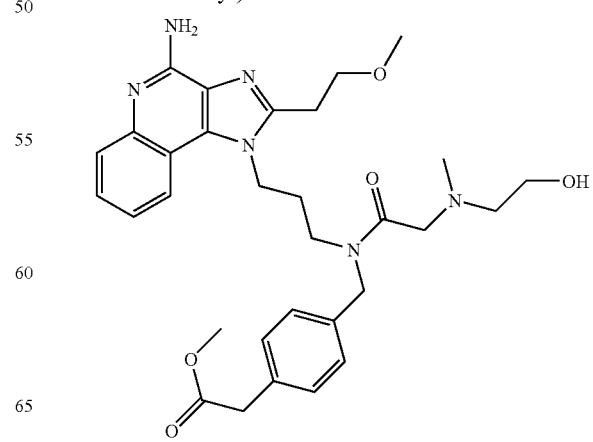

The title compound was prepared by the method of example 29 step (vi) using the product of example 29 step (v) (549 mg) and 2-(methylamino)ethanol (81 mg) to give the free base as a gum. The dissacchrin salt was formed as in example 35 to give the title compound as a white solid 27 mg.

$^1$H NMR DMSO-d6: δ 8.17-8.22 (m, 1H), 7.88-7.85 (m, 1H), 7.90-7.56 (m, 10H), 7.26-7.13 (m, 4H), 4.64-4.55 (m, 6H), 3.86-3.80 (m, 4H), 3.61-3.14 (m, 13H), 2.32-1.71 (m, 6H).

MS: Multimode+: 573

Example 39

Methyl 2-(3-((N-(3-(4-amino-2-butyl-1H-imidazo[4,5-c]quinolin-1-yl)propyl)-2-((2-methoxyethyl)(methyl)amino)acetamido)methyl)phenyl)acetate

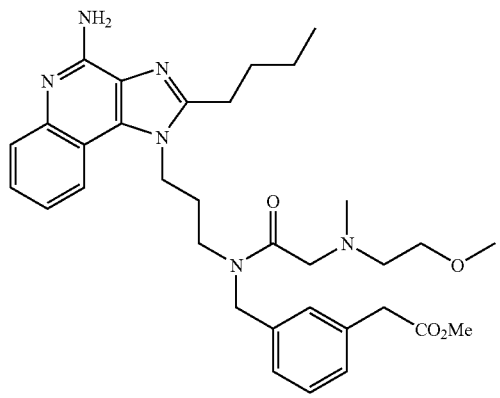 [SMILES: CCCCc1nc2c(N)nc3ccccc3c2n1CCCN(Cc1cccc(CC(=O)OC)c1)C(=O)CN(C)CCOC]

(i) Methyl 2-(3-4N-(3-(4-amino-2-butyl-1H-imidazo[4,5-c]quinolin-1-yl)propyl)2-chloroacetamido)methyl)phenyl)acetate Chloroacetyl chloride (0.434 mL, 5.44 mmol) was added to the product of example 2 (2.50 g) in CHCl$_3$ (75 mL) at 0° C. The resulting solution was stirred at 0° C. for 1 h, then 0.2 N HCl aq. (100 mL) was added and extracted with CHCl$_3$ (100 mL). The organic layer was dried and concentrated in vacuo.

$^1$H NMR (CDCl$_3$) δ 8.00 (1H, d), 7.96 (1H, d), 7.64 (1H, dd), 7.55 (1H, dd), 7.33 (1H,), 7.23 (1H, d), 7.12 (1H, s), 7.08 (1H, d), 4.70 (2H, s), 4.51 (2H, dd), 4.16 (2H, s), 3.70 (3H, s), 3.66-3.62 (2H, m), 3.62 (2H, s), 2.88 (2H, dd), 2.18-2.10 (2H, m), 1.93-1.85 (2H, m), 1.57-1.48 (2H, m), 1.03 (3H, t).

(ii) Methyl 2-(3-4N-(3-(4-amino-2-butyl-1H-imidazo[4,5-c]quinolin-1-yl)propyl)-2-((2-methoxyethyl)(methyl)amino)acetamido)methyl)phenyl)acetate Acetonitrile (75 ml) was added to the residue, then excess N 2-methoxyethylmetylamine was added at 0° C. The resulting solution was stirred at rt for 4 h. The solvent was evaporated. To the residue, 0.2N HCl aq. (100 mL) was added and extracted with CHCl$_3$/MeOH=20/1 (100 mL). The water layer was neutralized with NH$_3$ aq. and then extracted with EtOAc/hexane=2/1 (100 ml). The combined organic layer was washed with brine, dried and concentrated in vacuo to give the title compound 266 mg as a gum.

$^1$H NMR (DMSO-d$_6$) δ 8.00 (0.5H, d), 8.00 (0.5H, d), 7.66 (1H, dd), 7.45-7.39 (1H, m), 7.27-7.20 (2H, m), 7.16-7.00 (3H, m), 6.46 (2H, brs), 4.72 (1H, s), 4.52-4.38 (3H, m), 3.64 (1H, s), 3.60 (1H, s), 3.57 (1.5H, s), 3.56 (1.5H, s), 3.51 (1H, t), 3.42 (1H, t), 3.33-3.28 (2H, m), 3.23 (1H, s), 3.19 (1H, s), 3.13 (1.5H, s), 3.09 (1.5H, s), 2.90-2.81 (2H, m), 2.55 (1H, t), 2.47 (1H, t), 2.22 (1.5H, s), 2.12 (1.5H, s), 2.12-2.05 (1H, m), 2.01-1.92 (1H, m), 1.82-1.71 (2H, m), 1.46-1.38 (2H, m), 0.94 (3H, t).

MS:ESI 589 (M+1)

Example 40

Methyl 2-(3-((N-(3-(4-amino-2-butyl-1H-imidazo[4,5-c]quinolin-1-yl)propyl)-2-(butyl(methyl)amino)acetamido)methyl)phenyl)acetate

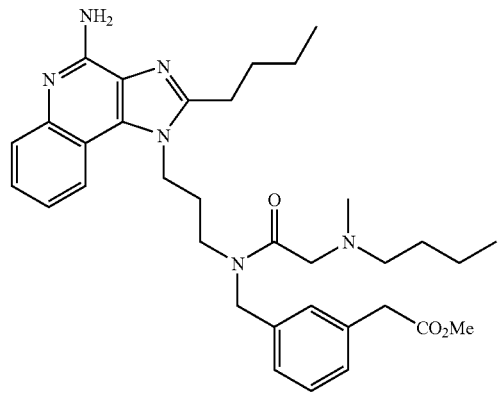 [SMILES: CCCCc1nc2c(N)nc3ccccc3c2n1CCCN(Cc1cccc(CC(=O)OC)c1)C(=O)CN(C)CCCC]

The title compound was prepared by the method of example 39 using 312 mg of the product from step (i) and N-butyl-N-methylamine to give the title compound 276 mg as a gum.

$^1$H NMR (DMSO-d$_6$) δ 8.00 (0.5H, d), 7.96 (0.5H, d), 7.60 (1H, dd), 7.42 (1H, dd), 7.27-7.22 (2H, m), 7.15-7.02 (3H, m), 6.45 (2H, brs), 4.71 (1H, s), 4.50 (1H, t), 4.47 (1H, s), 4.42 (1H, t), 3.64 (1H, s), 3.60 (1H, s), 3.58 (1.5H, s), 3.57 (1.5H, s), 3.51 (1H, t), 3.42 (1H, t), 3.15 (1H, s), 3.06 (1H, s), 2.85 (2H, t), 2.32 (1H, t), 2.24-2.16 (1H, m), 2.17 (1.5H, s), 2.13-2.05 (1H, m), 2.01 (1.5H, s), 2.00-1.91 (1H, m), 1.82-1.71 (2H, m), 1.47-1.38 (2H, m), 1.31-1.10 (4H, m), 0.94 (3H, t), 0.78 (3H, m).

MS:ESI 587 (M+1)

Example 41

Methyl 3-4N-(3-(4-amino-2-butyl-1H-imidazo[4,5-c]quinolin-1-yl)propyl)-2-(dipropylamino)acetamido)methyl)phenyl)acetate

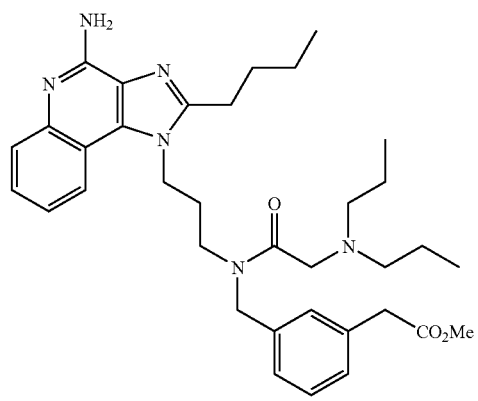 [SMILES: CCCCc1nc2c(N)nc3ccccc3c2n1CCCN(Cc1cccc(CC(=O)OC)c1)C(=O)CN(CCC)CCC]

The title compound was prepared by the method of example 39 using 308 mg of the product from step (i) and dipropylamine to give the title compound 250 mg as gum.

¹H NMR (DMSO-d₆) δ 8.00-7.94 (1H, m), 7.60 (1H, dd), 7.45-7.40 (1H, m), 7.27-7.20 (2H, m), 7.18-7.02 (3H, m), 6.46 (2H, brs), 4.73 (1H, m), 4.49-4.38 (3H, m), 3.64 (1H, s), 3.59 (1H, s), 3.58 (1.5H, s), 3.57 (1.5H, s), 3.55-3.51 (1H, m), 3.42 (1H, t), 3.22 (1H, s), 3.20 (1H, s), 2.85 (2H, t), 2.38 (2H, t), 2.27 (2H, t), 2.20-2.10 (1H, m), 2.03-1.92 (1H, m), 1.82-1.71 (2H, m), 1.45-1.38 (2H, m), 1.31-1.22 (4H, m), 0.94 (3H, t), 0.73 (6H, m)
MS:ESI 601 (M+1)

Example 42

Methyl 2-(3-((N-(3-(4-amino-2-butyl-1H-imidazo[4,5-c]quinolin-1-yl)propyl)-2-(bis(2-hydroxyethyl)amino)acetamido)methyl)phenyl)acetate

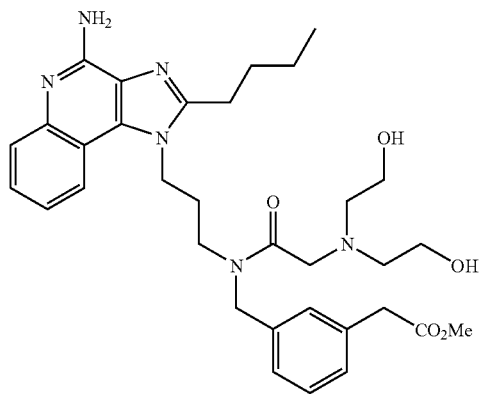 [SMILES: CCCCc1nc2c(N)nc3ccccc3c2n1CCCN(Cc1cccc(CC(=O)OC)c1)C(=O)CN(CCO)CCO]

The title compound was prepared by the method of example 39 using 240 mg of the product from step (i) and diethanolamine to give the title compound 130 mg as a gum.
¹H NMR (CDCl₃) δ 7.80 (2H, m), 7.47-7.51 (1H, m), 6.93-7.31 (5H, m), 5.79 (2H, brs), 4.40-4.53 (3H, m), 3.68 (3H, s), 3.53-3.58 (7H, m), 3.40 (1H, m), 2.82-2.85 (5H, m), 2.57-2.59 (1H, m), 2.08-2.13 (4H, m), 1.79-1.85 (3H, m), 1.45-1.50 (2H, m), 1.25 (2H, m), 0.98 (3H, t).
MS:ESI 605 (M+1)

Example 43

Methyl 2-(3-((N-(3-(4-amino-2-butyl-1H-imidazo[4,5-c]quinolin-1-yl)propyl)-2-(methyl(tetrahydro-2H-pyran-4-yl)amino)acetamido)methyl)phenyl)acetate

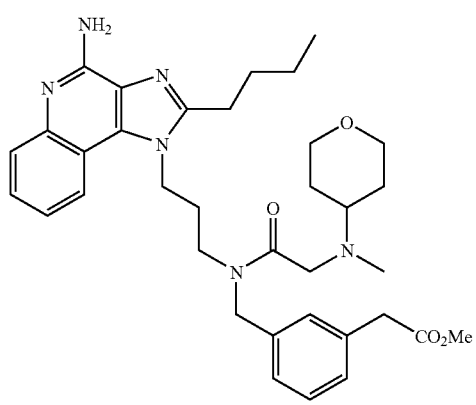 [SMILES: CCCCc1nc2c(N)nc3ccccc3c2n1CCCN(Cc1cccc(CC(=O)OC)c1)C(=O)CN(C)C1CCOCC1]

The title compound was prepared by the method of example 39 using 260 mg of the product from step (i) and N-methyl-N-tetrahydro-2H-pyran-4-ylamine to give the title compound 180 mg as a gum.

¹H NMR (CDCl₃) δ 7.85 (2H, t,), 7.52 (1H, m), 6.83-7.26 (5H, m), 5.65 (2H, brs), 4.71 (2H, s), 4.38-4.57 (2H, m), 3.96-4.00 (2H, m), 3.68 (3H, s), 3.50-3.58 (4H, m), 3.35 (3H, s), 2.83-2.87 (2H, m), 2.60 (1H, m), 2.07 (2H, m), 1.80-1.87 (6H, m), 1.67 (2H, m), 1.46-1.57 (4H, m), 1.25 (2H, m), 0.99 (3H, t)
MS:ESI 615 (M+1)

Example 44

Methyl 2-(3-((N-(3-(4-amino-2-butyl-1H-imidazo[4,5-c]quinolin-1-yl)propyl)-2-(azetidin-1-yl)acetamido)methyl)phenyl)acetate

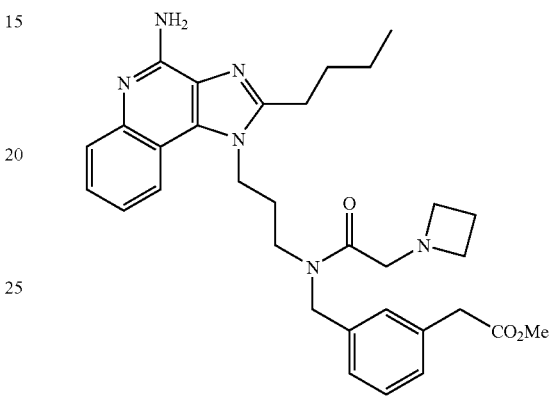

The title compound was prepared by the method of example 39 using 267 mg of the product from step (i) and azetidine to give the title compound 107 mg as a solid.
¹H NMR (DMSO-d₆) δ 8.03 (1/2H, d), 7.96 (½H, d, J), 7.61-7.56 (1H, m), 7.43 (1H, dd, 7.2, 7.9), 7.31-7.21 (2H, m), 7.17-7.01 (3H, m), 6.47(1H, brd), 4.63 (1H, s), 4.52 (1H, brt), 4.44 (1H, s), 4.45-4.38 (1H, m), 3.66 (1H, s), 3.61 (1H, s), 3.58 (3H, s), 3.45-3.35 (2H, m), 3.24 (1H, s), 3.17 (2H, t), 3.08 (1H, s), 3.02 (2H, t), 2.89-2.83 (2H, m), 2.11-2.02 (1H, m), 1.99-1.91 (2H, m), 1.86-1.73 (3H, m), 1.43 (2H, q), 0.95 (3H, t).
MS:ESI 557 (M+1)

Example 45

Methyl 2-(3-((N-(3-(4-amino-2-butyl-1H-imidazo[4,5-c]quinolin-1-yl)propyl)-2-(3-hydroxyazetidin-1-yl)acetamido)methyl)phenyl)acetate

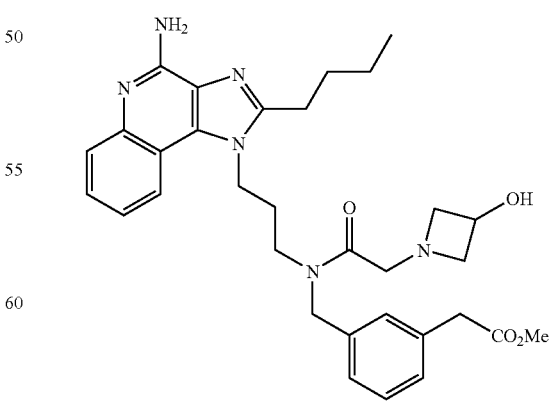

The title compound was prepared by the method of example 39 using 202 mg of the product from step (i) and 3-azetidinol to give the title compound 193 mg as a gum.

¹H NMR (CDCl₃) δ 7.87-7.83 (2H, m), 7.54-7.50 (1H, m), 7.36-7.32 (1H, m), 7.26-7.23 (1H, m), 7.17-7.13 (1H, m), 7.05-7.03 (1H, m), 7.00-6.97 (1H, m), 5.61-5.57 (2H, m), 4.54-4.41 (4H, m), 3.82-3.78 (2H, m), 3.68 (3H, s), 3.57-3.50 (4H, m), 3.41 (2H, s), 3.20-3.16 (0.5H, m), 3.09-3.06 (1.5H, m), 2.86-2.83 (2H, m), 2.20-2.15 (0.5H, m), 2.11-2.04 (1.5H, m), 1.85-1.74 (4H, m), 1.51-1.45 (2H, m), 0.99 (3H, t,).
MS:ESI 573 (M+1)

Example 46

Methyl 2-(3-((N-(3-(4-amino-2-butyl-1H-imidazo[4,5-c]quinolin-1-yl)propyl)-2-(pyrrolidin-1-yl)acetamido)methyl)phenyl)acetate

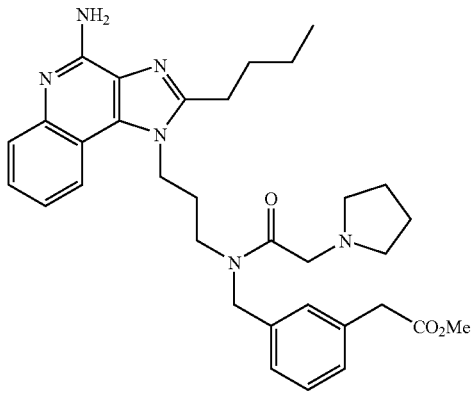 [SMILES: CCCCc1nc2c(N)nc3ccccc3c2n1CCCN(Cc1cccc(CC(=O)OC)c1)C(=O)CN1CCCC1]

The title compound was prepared by the method of example 39 using 300 mg of the product from step (i) and pyrrolidine to give the title compound 289 mg as a gum.
¹H NMR (DMSO-d₆) δ 8.01 (0.5H, d), 7.95 (0.5H, d), 7.62-7.59 (1H, m), 7.42 (1H, dd), 7.29-7.20 (2H, m), 7.15-7.05 (3H, m), 6.45 (2H, d), 4.69 (1H, s), 4.52 (1H, t), 4.48 (1H, s), 4.41 (1H, t), 3.63 (1H, s), 3.61 (1H, s), 3.57 (1.5H, s), 3.56 (1.5H, s), 3.51-3.46 (1H, m), 3.42 (1H, t), 3.28 (1H, s), 3.12 (1H, s), 2.84 (2H, t), 2.51-2.45 (2H, m), 2.34-2.28 (2H, m), 2.12-2.03 (1H, m), 2.02-1.91 (1H, m), 1.81-1.72 (2H, m), 1.66-1.60 (2H, m), 1.54-1.48 (2H, m), 0.94 (1.5H), 0.93 (1.5H, t).
MS:ESI 571 (M+1)

Example 47

Methyl 2-(3-((N-(3-(4-amino-2-butyl-1H-imidazo[4,5-c]quinolin-1-yl)propyl)-2-(3-hydroxypyrrolidin-1-yl)acetamido)methyl)phenyl)acetate

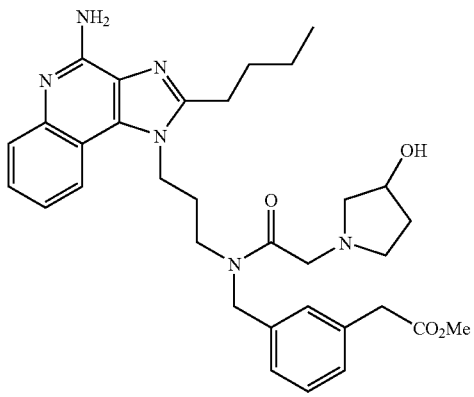 [SMILES: CCCCc1nc2c(N)nc3ccccc3c2n1CCCN(Cc1cccc(CC(=O)OC)c1)C(=O)CN1CCC(O)C1]

The title compound was prepared by the method of example 39 using 300 mg of the product from step (i) and DL-3-pyrroldinol to give the title compound 300 mg as a solid.

¹H NMR (DMSO-d₆) δ 7.99 (0.5H, d), 7.94 (0.5H, d), 7.60 (1H, dd), 7.43-7.39 (1H, m), 7.28-7.20 (2H, m), 7.14-7.02 (3H, m), 6.45 (2H, brs), 4.68-4.66 (2H, m), 4.65-4.39 (3H, m), 4.15-4.00 (1H, m), 3.63 (1H, s), 3.59 (1H, s), 3.57 (1.5H, s), 3.55 (1.5H, s), 3.52-3.32 (2H, m), 3.26 (1H, s), 3.22-3.11 (1H, m), 2.85-2.74 (2.5H, m), 2.70-2.62 (0.5H, m), 2.58-2.49 (0.5H, m), 2.37-2.24 (1.5H, m), 2.10-2.00 (1H, m), 1.98-1.72 (4H, m), 1.54-1.37 (3H, m), 0.93 (3H, t).
MS:ESI 587 (M+1)

Example 48

(R)-Methyl 2-(3-((N-(3-(4-amino-2-butyl-1H-imidazo[4,5-c]quinolin-1-yl)propyl)-2-(3-hydroxypyrrolidin-1-yl)acetamido)methyl)phenyl)acetate

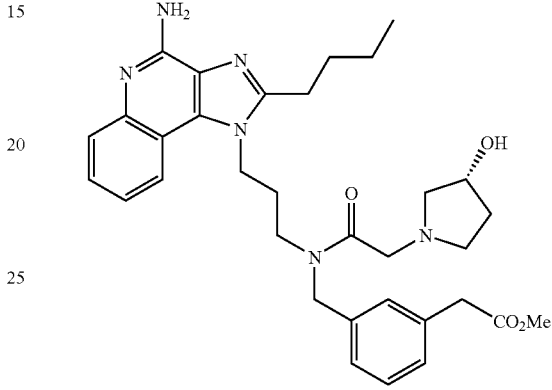

The title compound was prepared by the method of example 39 using 300 mg of the product from step (i) and (R)-3-pyrrolidinol to give the title compound 169 mg as a solid.
¹H NMR (DMSO-d₆) δ 7.99 (0.5H, d), 7.94 (0.5H, d), 7.60 (1H, dd), 7.43-7.39 (1H, m), 7.28-7.20 (2H, m), 7.14-7.02 (3H, m), 6.45 (2H, brs), 4.68-4.66 (2H, m), 4.65-4.39 (3H, m), 4.15-4.00 (1H, m), 3.63 (1H, s), 3.59 (1H, s), 3.57 (1.5H, s), 3.55 (1.5H, s), 3.52-3.32 (2H, m), 3.26 (1H, s), 3.22-3.11 (1H, m), 2.85-2.74 (2.5H, m), 2.70-2.62 (0.5H, m), 2.58-2.49 (0.5H, m), 2.37-2.24 (1.5H, m), 2.10-2.00 (1H, m), 1.98-1.72 (4H, m), 1.54-1.37 (3H, m), 0.93 (3H, t).
MS:ESI 587 (M+1)

Example 49

Methyl 2-(3-((N-(3-(4-amino-2-butyl-1H-imidazo[4,5-c]quinolin-1-yl)propyl)-2-(piperidin-1-yl)acetamido)methyl)phenyl)acetate

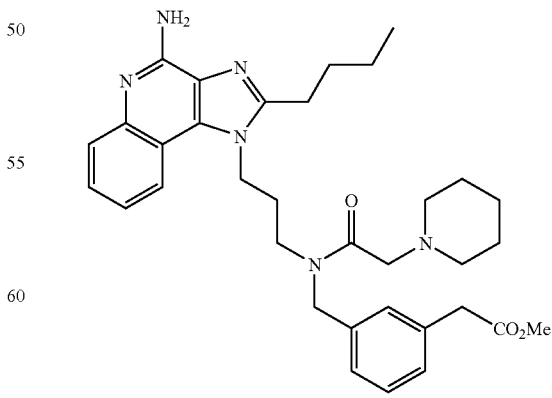

The title compound was prepared by the method of example 39 using 300 mg of the product from step (i) and piperidine to give the title compound 300 mg as a gum.

¹H NMR (DMSO-d₆) δ 8.01 (0.5H, d), 7.95 (0.5H, d), 7.63-7.59 (1H, m), 7.42 (1H, dd), 7.29-7.20 (2H, m), 7.15-7.09 (2H, m), 7.04-7.01 (1H, m), 6.46 (2H, brs), 4.69 (1H, s), 4.53 (1H, t), 4.48 (1H, s), 4.40 (1H, t), 3.63 (1H, s), 3.60 (1H, s), 3.58 (1.5H, s), 3.56 (1.5H, s), 3.50 (1H, t), 3.40 (1H), 3.10 (1H, s), 2.93 (1H, s), 2.87-2.81 (2H, m), 2.38-2.32 (2H, m), 2.21-2.14 (2H, m), 2.14-2.06 (1H, m), 1.99-1.90 (1H, m), 1.82-1.71 (2H, m), 1.47-1.31 (8H, m), 0.94 (1.5H, t), 0.93 (1.5H).
MS:ESI 585 (M+1)

Example 50

Methyl 2-(3-((N-(3-(4-amino-2-butyl-1H-imidazo[4,5-c]quinolin-1-yl)propyl)-2-(4-hydroxypiperidin-1-yl)acetamido)methyl)phenyl)acetate

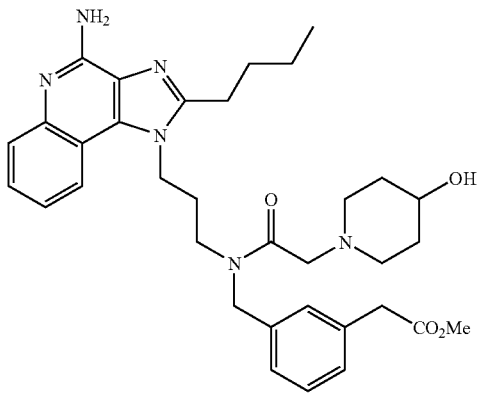 [SMILES: CCCCc1nc2c(N)nc3ccccc3c2n1CCCN(Cc1cccc(CC(=O)OC)c1)C(=O)CN1CCC(O)CC1]

The title compound was prepared by the method of example 39 using 600 mg of the product from step (i) and 4-hydroxypiperidine to give the title compound 660 mg as a solid.
¹H NMR (DMSO-d₆) δ 8.01 (0.5H, d), 7.93 (0.5H, d), 7.60 (1H, dd), 7.43-7.38 (1H, m), 7.26-7.19 (2H, m), 7.13-7.10 (2H, m), 7.00 (1H, brs), 6.45 (2H, brs), 4.68 (1H, s), 4.54-4.50 (2H, m), 4.46 (1H, s), 4.41-4.37 (1H, m), 3.63 (1H, s), 3.59 (1H, s), 3.56 (1.5H, s), 3.55 (1.5H, s), 3.52-3.43 (1H, m), 3.41-3.28 (1H, m), 3.11 (1H, s), 2.95 (1H, s), 2.85-2.80 (2H, m), 2.68-2.58 (1H, m), 2.51-2.47 (1H, m), 2.16-2.12 (2H, m), 2.00-1.88 (2H, m), 1.79-1.68 (2H, m), 1.65-1.53 (2H, m), 1.48-1.33 (2H, m), 1.32-1.23 (2H, m), 0.95-0.90 (3H, m).
MS:ESI 601 (M+1)

Example 51

Methyl 2-(3-((N-(3-(4-amino-2-butyl-1H-imidazo[4,5-c]quinolin-1-yl)propyl)-2-(4-methoxypiperidin-1-yl)acetamido)methyl)phenyl)acetate

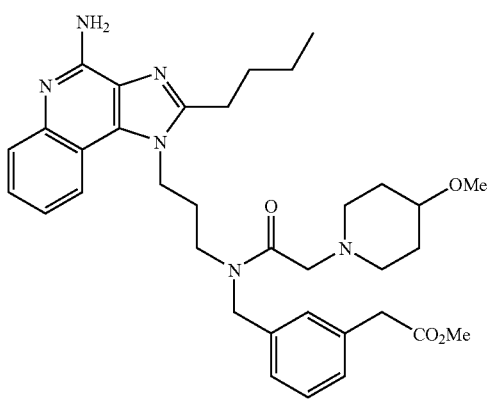 [SMILES: CCCCc1nc2c(N)nc3ccccc3c2n1CCCN(Cc1cccc(CC(=O)OC)c1)C(=O)CN1CCC(OC)CC1]

The title compound was prepared by the method of example 39 using 300 mg of the product from step (i) and 4-methoxypiperidine to give the title compound 230 mg as a gum.
¹H NMR (DMSO-d6) δ 8.00 (0.5H, d), 7.93 (0.5H, d), 7.61-7.58 (1H, m), 7.43-7.37 (1H, m), 7.26-7.19 (2H, m), 7.13-7.09 (2H, m), 7.00 (1H, brs), 6.45 (2H, brd), 4.67 (1H, s), 4.54-4.50 (1H, m), 4.46 (1H, s), 4.41-4.37 (1H, m), 3.62 (1H, s), 3.59 (1H, s), 3.57 (1.5H, s), 3.55 (1.5H, s), 3.52-3.36 (2H, m), 3.17 (1.5H, s), 3.16 (1.5H, s), 3.13 (1H, s), 3.12-3.00 (1H, m), 2.94 (1H, s), 2.86-2.81 (2H, m), 2.68-2.63 (1H, m), 2.53-2.49 (1H, m), 2.18-2.00 (2H, m), 1.98-1.88 (2H, m), 1.80-1.63 (4H, m), 1.44-1.25 (4H, m), 0.95-0.90 (3H, m).
MS:ESI 615 (M+1)

Example 52

Methyl 2-(3-((N-(3-(4-amino-2-butyl-1H-imidazo[4,5-c]quinolin-1-yl)propyl)-2-(4-(dimethylcarbamoyl)piperidin-1-yl)acetamido)methyl)phenyl)acetate

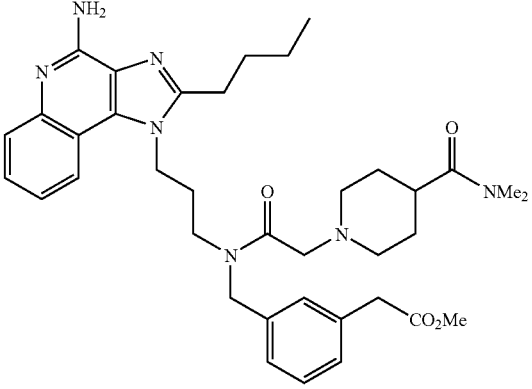 [SMILES: CCCCc1nc2c(N)nc3ccccc3c2n1CCCN(Cc1cccc(CC(=O)OC)c1)C(=O)CN1CCC(C(=O)N(C)C)CC1]

The title compound was prepared by the method of example 39 using 300 mg of the product from step (i) and N,N-dimethylpiperidine-4-carboxamide to give the title compound 265 mg as a gum.
¹H NMR (DMSO-d₆) δ 8.00 (0.5H, d), 7.93 (0.5H, d), 7.61-7.58 (1H, m), 7.43-7.38 (1H, m), 7.27-7.19 (2H, m), 7.16-7.09 (2H, m), 7.00-6.99 (1H, m), 6.45 (2H, brs), 4.67 (1H, s), 4.54-4.50 (1H, m), 4.46 (1H, s), 4.41-4.37 (1H, m), 3.64 (1H, s), 3.58 (1H, s), 3.57 (1.5H, s), 3.55 (1.5H, s), 3.50-3.47 (1H, m), 3.41-3.37 (1H, m), 3.33 (1H, s), 3.14 (1H, s), 2.98 (1.5H, s), 2.95 (1.5H, s), 2.93 (1H, s), 2.86-2.74 (6H, m), 2.68-2.64 (1H, m), 2.07-1.84 (4H, m), 1.78-1.70 (2H, m), 1.55-1.37 (6H, m), 0.95-0.90 (3H, m
MS:ESI 656 (M+1)

Example 53

Methyl 2-(3-((N-(3-(4-amino-2-butyl-1H-imidazo[4,5-c]quinolin-1-yl)propyl)-2-morpholinoacetamido)methyl)phenyl)acetate

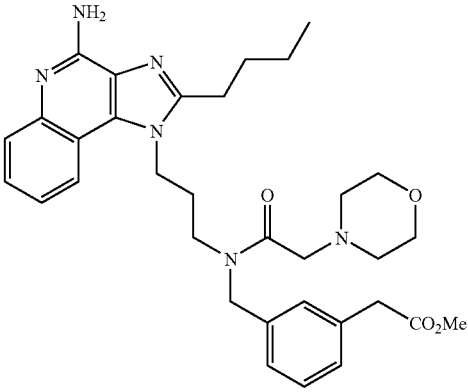

The title compound was prepared by the method of example 39 using 300 mg of the product from step (i) and morpholine to give the title compound 294 mg as a solid.

¹H NMR (DMSO-d₆) δ 8.03 (0.5H, d), 7.95 (0.5H, d), 7.63-7.59 (1H, m), 7.42 (1H, dd), 7.30-7.20 (2H, m), 7.15-7.08 (2H, m), 7.04-7.01 (1H, m), 6.46 (2H, d), 4.68 (1H, s), 4.55 (1H, t), 4.47 (1H, s), 4.41 (1H, t), 3.64 (1H, s), 3.60 (1H, s), 3.58 (1.5H, s), 3.57 (1.5H, s), 3.51-3.39 (6H, m), 3.17 (1H, s), 2.98 (1H, s), 2.88-2.82 (2H, m), 2.41-2.37 (2H, m), 2.25-2.20 (2H, m), 2.15-2.06 (1H, m), 2.00-1.91 (1H, m), 1.82-1.72 (2H, m), 1.47-1.37 (2H, m), 0.94 (1.5H, t), 0.93 (1.5H, t)

MS:ESI 587 (M+1)

Example 54

Methyl 2-(3-((N-(3-(4-amino-2-butyl-1H-imidazo[4,5-c]quinolin-1-yl)propyl)-2-((2S,6R)-2,6-dimethylmorpholino)acetamido)methyl)phenyl)acetate

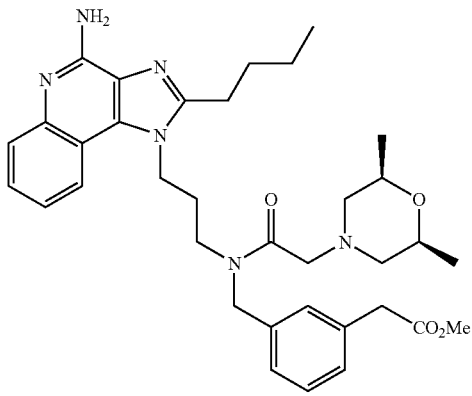 [SMILES: CCCCc1nc2c(N)nc3ccccc3c2n1CCCN(Cc1cccc(CC(=O)OC)c1)C(=O)CN1C[C@@H](C)O[C@@H](C)C1]

The title compound was prepared by the method of example 39 using 206 mg of the product from step (i) and cis-2,6-dimethylmorpholine to give the title compound 232 mg as a solid.

¹H NMR (CDCl₃) δ 7.86-7.84 (2H, m), 7.55-7.51 (1H, m), 7.35-7.31 (1H, m), 7.25-7.21 (1H, m), 7.14-7.12 (1H, m), 7.03-6.99 (2H, m), 5.73 (1.5H, brs), 5.56 (0.5H, brs), 4.63 (1.5H, s), 4.57 (0.5H, s), 4.42 (2H, t), 3.68-3.64 (5H, m), 3.58-3.49 (4H, m), 3.22 (1.5H, s), 2.92 (0.5H, s), 2.86-2.75 (4H, m), 2.24-2.05 (2H, m), 1.89-1.81 (4H, m), 1.51-1.45 (2H, m), 1.12-1.10 (6H, m), 0.99 (3H, t).

MS:ESI 615 (M+1)

Example 55

Methyl 2-(3-((N-(3-(4-amino-2-butyl-1H-imidazo[4,5-c]quinolin-1-yl)propyl)-2-(4-methylpiperazin-1-yl)acetamido)methyl)phenyl)acetate

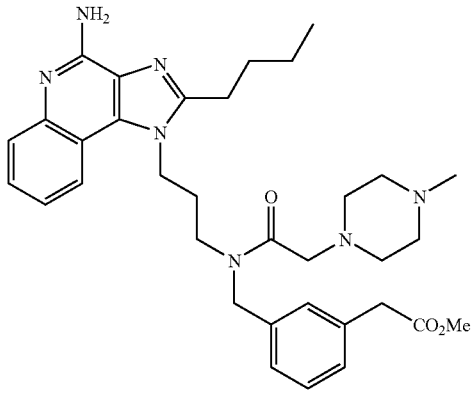 [SMILES: CCCCc1nc2c(N)nc3ccccc3c2n1CCCN(Cc1cccc(CC(=O)OC)c1)C(=O)CN1CCN(C)CC1]

The title compound was prepared by the method of example 39 using 300 mg of the product from step (i) and 1-methylpiperazine to give the title compound 320 mg as a gum. ¹H NMR (CDCl₃) δ 7.85 (1H, m), 7.53 (1H, m), 7.36 (1H, m), 7.23 (2H, m), 7.13 (1H, m), 7.04-7.00 (2H, m), 5.61 (2H, brs), 4.66 (2H, s), 4.44 (2H, t, J=7.6 Hz), 3.67 (3H, s), 3.56 (2H, s), 3.51 (2H, t), 3.25 (2H, s), 2.84 (2H, t), 2.67-2.25 (6H, m), 2.21 (3H, s), 2.20-2.03 (4H, m), 1.87-1.79 (2H, m), 1.52-1.44 (2H, m), 1.00 (3H, t).

MS:ESI 600 (M+1)

Example 56

Methyl 2-(3-((N-(3-(4-amino-2-butyl-1H-imidazo[4,5-c]quinolin-1-yl)propyl)-2-(4-(2-hydroxyethyl)piperazin-1-yl)acetamido)methyl)phenyl)acetate

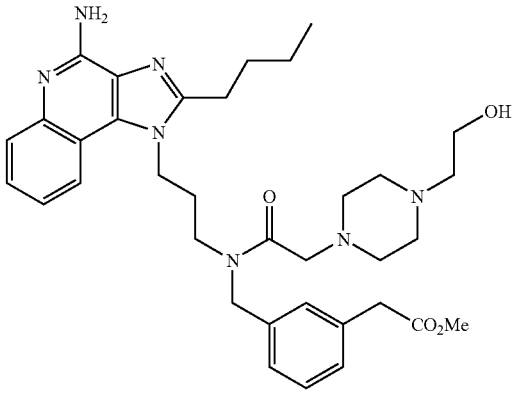 [SMILES: CCCCc1nc2c(N)nc3ccccc3c2n1CCCN(Cc1cccc(CC(=O)OC)c1)C(=O)CN1CCN(CCO)CC1]

The title compound was prepared by the method of example 39 using 300 mg of the product from step (i) and 1-piperazineethanol to give the title compound 337 mg as a solid.

¹H NMR (CDCl₃) δ 7.86 (1H, m), 7.54 (1H, m), 7.37 (1H, m), 7.24 (2H, m), 7.13 (1H, m), 7.08-6.99 (2H, m), 5.81 (2H, brs), 4.66 (2H, s), 4.45 (2H, t), 3.67 (3H, s), 3.58 (2H, s), 3.52 (2H, t), 3.48 (1H, brs), 3.26 (2H, s), 2.85 (2H, t), 2.67-2.03 (14H, m), 1.88-1.81 (2H, m), 1.52-1.45 (2H, m), 1.00 (3H, t).

MS:ESI 630 (M+1)

Example 57

Methyl 2-(3-((N-(3-(4-amino-2-butyl-1H-imidazo[4,5-c]quinolin-1-yl)propyl)-2-(4-(2-methoxyethyl)piperazin-1-yl)acetamido)methyl)phenyl)acetate

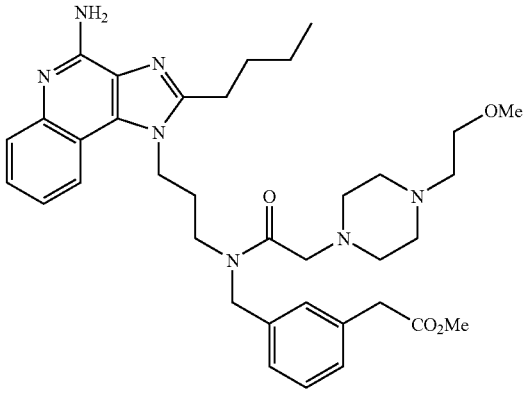 [SMILES: CCCCc1nc2c(N)nc3ccccc3c2n1CCCN(Cc1cccc(CC(=O)OC)c1)C(=O)CN1CCN(CCOC)CC1]

The title compound was prepared by the method of example 39 using 300 mg of the product from step (i) and 1-(2-methoxyethyl)piperazine to give the title compound 354 mg as a gum.

¹H NMR (CDCl₃) δ 7.87 (1H, m), 7.54 (1H, m), 7.38 (1H, m), 7.24 (2H, m), 7.14 (1H, m), 7.06-6.99 (2H, m), 5.93 (2H, brs), 4.67 (2H, s), 4.43 (2H, t), 3.67 (3H, s), 3.57 (2H, s), 3.56-3.46 (4H, m), 3.32 (3H, s), 3.25 (2H, s), 2.84 (2H, t), 2.59-2.20 (10H, m), 2.12-2.05 (2H, m), 1.87-1.80 (2H, m), 1.52-1.45 (2H, m), 1.00 (3H, t).
MS:ESI 644 (M+1)

Example 58

Methyl 2-(3-((2-(4-acetylpiperazin-1-yl)-N-(3-(4-amino-2-butyl-1H-imidazo[4,5-c]quinolin-1-yl)propyl)acetamido)methyl)phenyl)acetate

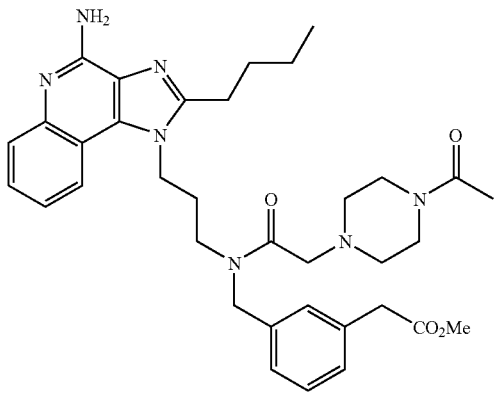 [SMILES: CCCCc1nc2c(N)nc3ccccc3c2n1CCCN(Cc1cccc(CC(=O)OC)c1)C(=O)CN1CCN(C(C)=O)CC1]

The title compound was prepared by the method of example 39 using 300 mg of the product from step (i) and 1-acetylpiperazine to give the title compound 333 mg as a solid.
¹H NMR (CDCl₃) δ 7.85 (1H, m), 7.54 (1H, m), 7.33 (1H, m), 7.24 (2H, m), 7.14 (1H, m), 7.04-6.97 (2H, m), 5.72 (2H, brs), 4.67 (2H, s), 4.43 (2H, t,), 3.67 (3H, s), 3.63-3.27 (6H, m), 3.56 (2H, s), 3.28 (2H, s), 2.85 (2H, t), 2.56-2.07 (6H, m), 2.06 (3H, s), 1.86-1.81 (2H, m), 1.52-1.45 (2H, m), 1.00 (3H, t).
MS:ESI 628 (M+1)

Example 59

Methyl 2-(3-((N-(3-(4-amino-2-butyl-1H-imidazo[4,5-c]quinolin-1-yl)propyl)-2-(4-(methylsulfonyl)piperazin-1-yl)acetamido)methyl)phenyl)acetate

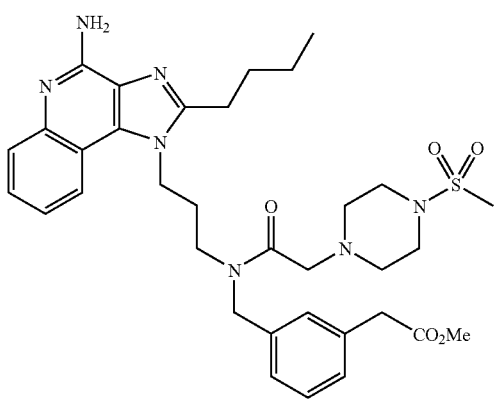 [SMILES: CCCCc1nc2c(N)nc3ccccc3c2n1CCCN(Cc1cccc(CC(=O)OC)c1)C(=O)CN1CCN(S(C)(=O)=O)CC1]

The title compound was prepared by the method of example 39 using 297 mg of the product from step (i) and 1-methanesulfonyl-piperazine to give the title compound 286 mg as a solid.

¹H NMR (DMSO-d₆) δ 8.03 (0.5H, d), 7.96 (0.5H, d), 7.61 (1H, d), 7.43 (1H, dd), 7.30-7.21 (2H, m), 7.15-7.06 (2H, m), 7.04-7.02 (1H, m), 6.51 (1H, brs), 6.48 (1H, brs), 4.66 (1H, s), 4.55 (1H, t), 4.47 (1H, s), 4.43 (1H, t), 3.66 (1H, s), 3.61 (1H, s), 3.58 (1.5H, s), 3.57 (1.5H, s), 3.50-3.42 (2H, m), 3.31 (2H, s), 3.25 (1H, s), 3.04 (1H, s), 2.98-2.90 (4H, m), 2.89-2.82 (2H, m), 2.78 (1.5H, s), 2.77 (1.5H, s), 2.36-2.30 (2H, m), 2.12-2.05 (1H, m), 2.02-1.94 (1H, m), 1.82-1.73 (2H, m), 1.46-1.38 (2H, m), 0.96-0.91 (3H, m).
MS:ESI 664 (M+1)

Example 60

Methyl 2-(3-((N-(3-(4-amino-2-butyl-1H-imidazo[4,5-c]quinolin-1-yl)propyl)-2-(azepan-1-yl)acetamido)methyl)phenyl)acetate

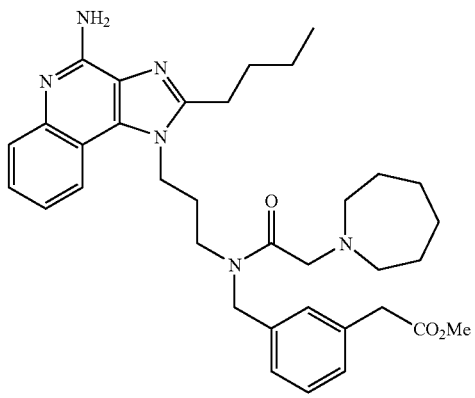 [SMILES: CCCCc1nc2c(N)nc3ccccc3c2n1CCCN(Cc1cccc(CC(=O)OC)c1)C(=O)CN1CCCCCC1]

The title compound was prepared by the method of example 39 using 201 mg of the product from step (i) and homopiperidine to give the title compound 221 mg as a gum.
¹H NMR (CDCl₃) δ 7.87 (0.5H, d), 7.84 (1.5H, d), 7.54-7.50 (1H, m), 7.32-7.30 (1H, m), 7.22 (1H, d), 7.14-7.12 (1H, m), 7.03-7.01 (2H, m), 5.59 (1.5H, brs), 5.50 (0.5H, brs), 4.73 (1.5H, s), 4.57 (0.5H, s), 4.43 (2H, t), 3.67 (3H, s), 3.57 (2H, s), 3.52 (2H, t), 3.38 (1.5H, s), 3.23 (0.5H, s), 2.87-2.78 (2H, m), 2.71 (3H, t), 2.57 (1H, t), 2.25-2.04 (2H, m), 1.85-1.81 (2H, m), 1.68-1.53 (8H, m), 1.51-1.45 (2H, m), 0.99 (3H, t).
MS:ESI 599 (M+1)

Example 61

Methyl 2-(3-((N-(3-(4-amino-2-butyl-1H-imidazo[4,5-c]quinolin-1-yl)propyl)-2-(1,4-oxazepan-4-yl)acetamido)methyl)phenyl)acetate

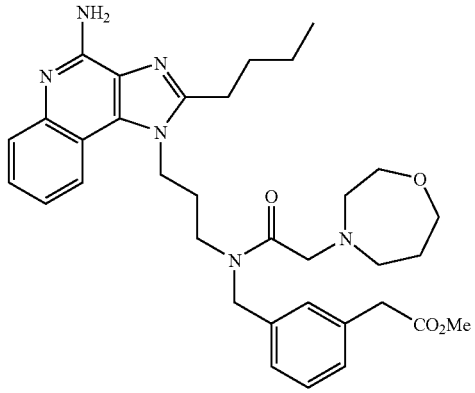 [SMILES: CCCCc1nc2c(N)nc3ccccc3c2n1CCCN(Cc1cccc(CC(=O)OC)c1)C(=O)CN1CCCOCC1]

The title compound was prepared by the method of example 39 using 257 mg of the product from step (i) and homomorphine to give the title compound 276 mg as a solid.

¹H NMR (CDCl₃) δ 8.02 (1/2H, d), 7.96 (1/2H, d), 7.63-7.60 (1H, m), 7.45-7.40 (1H, m), 7.30-7.21 (2H, m), 7.16-7.01 (3H, m), 6.46 (2H, brs), 4.68 (1H, s), 4.57-4.51 (1H, m), 4.48 (1H, s), 4.44-4.39 (1H, m), 3.68-3.29 (7H, m), 3.58 (3/2H, s), 3.57 (3/2H, s), 3.16 (1H, s), 2.89-2.81 (2H, m), 2.78-2.65 (5H, m), 2.17-2.08 (1H, m), 2.01-1.92 (1H, m), 1.81-1.61 (5H, m), 1.48-1.37 (2H, m), 0.94 (3/2H, t), 0.94 (3/2H, t).

MS:ESI 601 (M+1)

Example 62

Methyl 2-(3-((N-(3-(4-amino-2-butyl-1H-imidazo[4,5-c]quinolin-1-yl)propyl)-2-(4-methyl-1,4-diazepan-1-yl)acetamido)methyl)phenyl)acetate

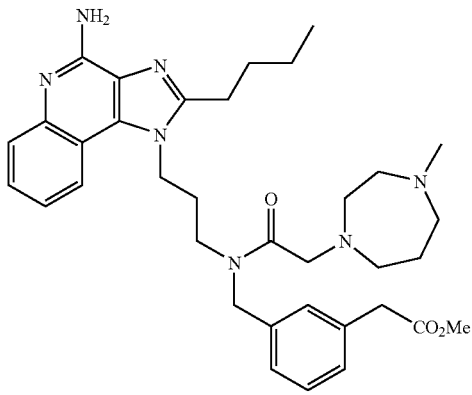 [SMILES: CCCCc1nc2c(N)nc3ccccc3c2n1CCCN(Cc1cccc(CC(=O)OC)c1)C(=O)CN1CCCN(C)CC1]

The title compound was prepared by the method of example 39 using 200 mg of the product from step (i) and N-methylhomopiperazine to give the title compound 200 mg as a gum.

¹H NMR (CDCl₃) δ 7.86-7.82 (2H, m), 7.53-7.49 (1H, m), 7.33-7.31 (1H, m), 7.25-7.21 (1H, m), 7.14-7.12 (1H, m), 7.02-6.99 (2H, m), 5.46 (2H, brs), 4.65 (1.5H, s), 4.56 (0.5H, s), 4.43 (2H, t), 3.67 (3H, s), 3.57-3.49 (4H, m), 3.41 (1.5H, s), 3.16 (0.5H, s), 2.87-2.80 (5H, m), 2.66-2.56 (5H, m), 2.35 (2.25H, s), 2.34 (0.75H, s), 2.22-2.04 (4H, m), 1.85-1.81 (4H, m), 0.99 (3H, t).

MS:ESI 614 (M+1)

Example 63

Methyl 2-(3-((2-(4-acetyl-1,4-diazepan-1-yl)-N-(3-(4-amino-2-butyl-1H-imidazo[4,5-c]quinolin-1-yl)propyl)acetamido)methyl)phenyl)acetate

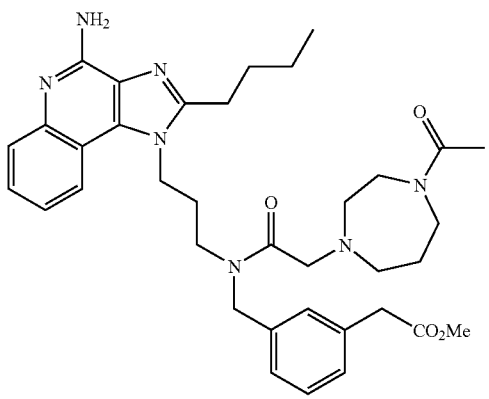 [SMILES: CCCCc1nc2c(N)nc3ccccc3c2n1CCCN(Cc1cccc(CC(=O)OC)c1)C(=O)CN1CCCN(C(C)=O)CC1]

The title compound was prepared by the method of example 39 using 270 mg of the product from step (i) and N-acetylhomopiperazine to give the title compound 290 mg as a solid.

¹H NMR (CDCl₃) δ 7.82-7.86 (2H, m), 7.52 (1H, m), 7.15-7.32 (4H, m), 6.81-7.00 (1H, m), 5.59 (2H, brs), 4.60 (2H, d), 4.43 (2H, t,), 3.40-3.69 (13H, m), 2.73-2.86 (5H, m), 1.81-2.07 (12H, m), 1.46-1.52 (2H, m), 1.25 (2H, m), 0.98-1.01 (3H, m).

MS:ESI 642 (M+1)

Example 64

Methyl 2-(3-((N-(3-(4-amino-2-butyl-1H-imidazo[4,5-c]quinolin-1-yl)propyl)-2-(4-(ethylcarbamoyl)-1,4-diazepan-1-yl)acetamido)methyl)phenyl)acetate

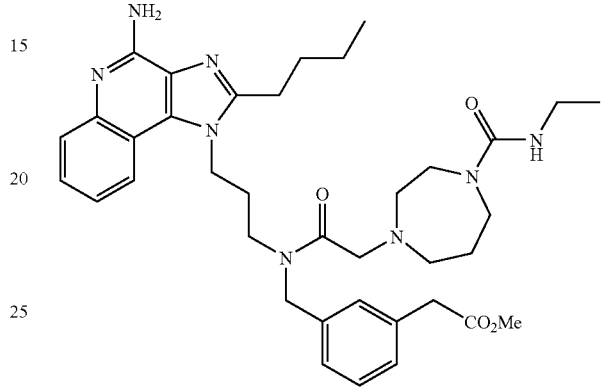

The title compound was prepared by the method of example 39 using 300 mg of the product from step (i) and N-ethyl-1,4-diazepane-1-carboxamide to give the title compound 146 mg as a solid.

¹H NMR (CDCl₃) δ 7.83-7.86 (2H, m), 7.52 (1H, t), 6.97-7.33 (5H, m), 5.59 (2H, brs), 4.55 (2H, s), 4.40-4.45 (2H, m), 3.68 (3H, d), 3.55-3.59 (5H, m), 3.38 (4H, m), 3.22-3.25 (2H, m), 2.73-2.78 (3H, m), 1.81-2.05 (9H, m), 1.47-1.49 (2H, m), 1.26-1.28 (2H, m), 1.10 (3H, t), 0.99 (3H, t).

MS:ESI 671 (M+1)

Example 65

Methyl 2-(3-((N-(3-(4-amino-2-butyl-1H-imidazo[4,5-c]quinolin-1-yl)propyl)-2-(4-(methylsulfonyl)-1,4-diazepan-1-yl)acetamido)methyl)phenyl)acetate

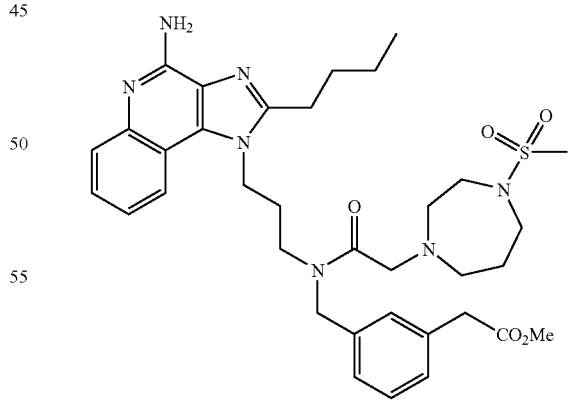

The title compound was prepared by the method of example 39 using 301 mg of the product from step (i) and 1-(methylsulfonyl)-1,4-diazepane to give the title compound 239 mg as a solid.

¹H NMR (DMSO-d₆) δ 8.02 (0.5H, d), 7.98 (0.5H, d), 7.61 (1H, d), 7.45-7.40 (1H, m), 7.29-7.20 (2H, m), 7.15-7.06 (2H, m), 7.04-7.01 (1H, m), 6.48 (1H, brs), 6.46 (1H, brs), 4.64

(1H, s), 4.53 (1H, t), 4.47 (1H, s), 4.44 (1H, t), 3.65 (1H, s), 3.61 (1H, s), 3.58 (1.5H, s), 3.57 (1.5H, s), 3.43-3.40 (3H, m), 3.30 (1H, s), 3.27-3.21 (3H, m), 3.17 (1H, t), 3.12-3.08 (1H, m), 2.88-2.84 (2H, m), 2.83 (1.5H, s), 2.82 (1.5H, s), 2.75-2.66 (2H, m), 2.60-2.51 (1H, m), 2.12-2.06 (1H, m), 2.00-1.94 (1H, m), 1.78-1.72 (2H, m), 1.70-1.65 (1H, m), 1.65-1.57 (1H, m), 1.46-1.38 (2H, m), 0.96-0.91 (3H, m).
MS:ESI 678 (M+1)

Example 66

Methyl 2-(4-((N-(3-(4-amino-2-butyl-1H-imidazo[4,5-c]quinolin-1-yl)propyl)-2-(4-(2-methoxyethyl)piperazin-1-yl)acetamido)methyl)phenyl)acetate

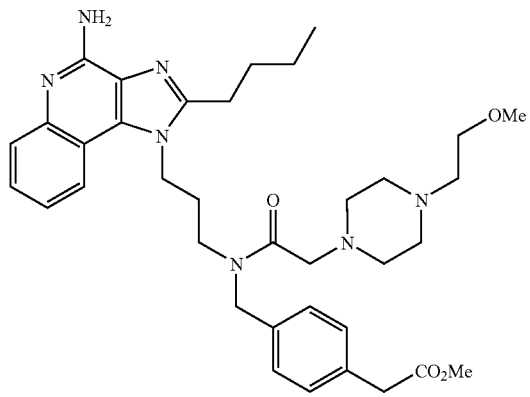 [SMILES: CCCCc1nc2c(N)nc3ccccc3c2n1CCCN(Cc1ccc(CC(=O)OC)cc1)C(=O)CN1CCN(CCOC)CC1]

The title compound was prepared by the method of example 39 using the product of example 1, step (i). Reaction of this product (204 mg) and 1-(2-methoxyethyl)piperazine gave the title compound (223 mg) as a gum.
$^1$H NMR (DMSO-d$_6$) δ 8.00 (0.5H, d, 7.93 (0.5H, d), 7.61-7.59 (1H, m), 7.41 (1H, t), 7.30-7.14 (4H, m), 7.06 (1H, d), 6.45 (2H, brs), 4.66 (1H, s), 4.53 (1H, t), 4.44 (1H, s), 4.40 (1H, t), 3.63 (1H, s), 3.62 (1H, s), 3.59 (3H, s), 3.48-3.37 (2H, m), 3.36-3.31 (4H, m), 3.19 (1.5H, s), 3.17 (1.5H, s), 3.13 (1H, s), 2.97 (1H, s), 2.87-2.81 (2H, m), 2.38-2.29 (4H, m), 2.27-2.19 (4H, m), 2.15-2.08 (1H, m), 1.98-1.90 (1H, m), 1.80-1.70 (2H, m), 1.46-1.37 (2H, m), 0.95-0.91 (3H, m)
MS:ESI 644 (M+1)

Example 67

Methyl 2-(4-((2-(4-acetyl-1,4-diazepan-1-yl)-N-(3-(4-amino-2-butyl-1H-imidazo[4,5-c]quinolin-1-yl)propyl)acetamido)methyl)phenyl)acetate

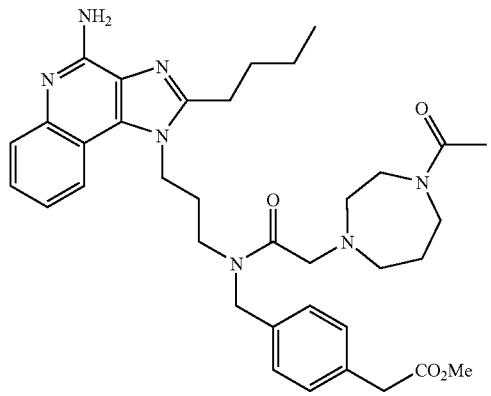 [SMILES: CCCCc1nc2c(N)nc3ccccc3c2n1CCCN(Cc1ccc(CC(=O)OC)cc1)C(=O)CN1CCCN(C(C)=O)CC1]

The title compound was prepared by the method of example 39 using the product of example 1, step (i). Reaction of this product (290 mg) and N-acetylhomopiperazine gave the title compound (220 mg) as a solid.
$^1$H NMR (CDCl$_3$) δ 7.83-7.86 (2H, m), 7.52 (1H, t), 7.18-7.33 (3H, m), 7.02-7.08 (2H, m), 5.69 (2H, brs), 4.59 (2H, d), 3.70 (3H, s), 3.40-3.64 (9H, m), 2.73-2.87 (5H, m), 2.05-2.09 (5H, m), 1.80-1.87 (11H, m), 1.46-1.52 (2H, m), 1.26 (2H, m), 0.99 (3H, t)
MS:ESI 642 (M+1)

Example 68

Methyl 2-(4-((N-(3-(4-amino-2-butyl-1H-imidazo[4,5-c]quinolin-1-yl)propyl)-2-(4-(methylsulfonyl)-1,4-diazepan-1-yl)acetamido)methyl)phenyl)acetate

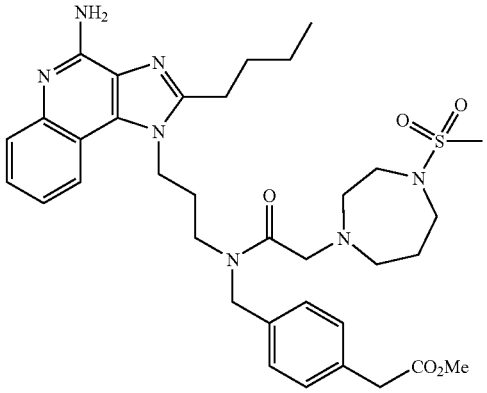 [SMILES: CCCCc1nc2c(N)nc3ccccc3c2n1CCCN(Cc1ccc(CC(=O)OC)cc1)C(=O)CN1CCCN(S(C)(=O)=O)CC1]

The title compound was prepared by the method of example 39 using the product of example 1, step (i). Reaction of this product (293 mg) and 1-(methylsulfonyl)-1,4-diazepane gave the title compound (291 mg) as a solid.
$^1$H NMR (DMSO-d$_6$) δ 8.02 (0.5H, d), 7.96 (0.5H, d), 7.61 (1H, d), 7.43 (1H, dd), 7.27-7.21 (2H, m), 7.17-7.13 (2H, m), 7.09-7.05 (1H, m), 6.51 (2H, brs), 4.63 (1H, s), 4.54 (1H, t), 4.44 (1H, s), 4.42 (1H, t), 3.64 (1H, s), 3.62 (1H, s), 3.60 (3H, s), 3.43-3.40 (3H, m), 3.32 (1H, s), 3.27-3.21 (3H, m), 3.17 (1H, t), 3.12-3.08 (1H, m), 2.90-2.83 (2H, m), 2.83 (3H, s), 2.75-2.66 (2H, m), 2.60-2.51 (1H, m), 2.12-2.05 (1H, m), 2.00-1.95 (1H, m), 1.78-1.72 (2H, m), 1.70-1.65 (1H, m), 1.65-1.57 (1H, m), 1.46-1.38 (2H, m), 0.94 (3H, t).
MS:ESI 678 (M+1)

Example 69

Methyl 2-(4-((2-((1-acetylpiperidin-4-yl)(methyl)amino)-N-(3-(4-amino-2-butyl-1H-imidazo[4,5-c]quinolin-1-yl)propyl)acetamido)methyl)phenyl)acetate

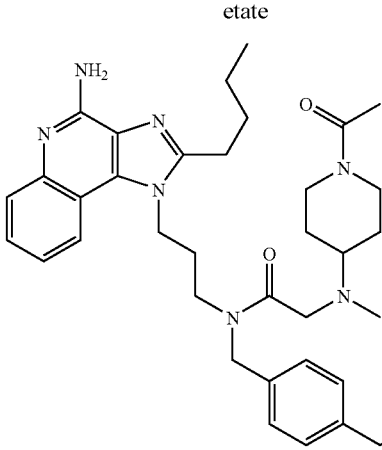

The title compound was prepared by the method of example 39 using the product of example 1, step (i). Reaction of this product (329 mg) and 1-acetyl-N-methylpiperidine-4-amine gave the title compound (63 mg) as a gum.

$^1$H NMR 6 (DMSO-d$_6$) 8.00 (0.5H, d), 7.94 (0.5H, d), 7.62-7.58 (1H, m), 7.43-7.38 (1H, m), 7.24-7.08 (5H, m), 6.49 (2H, brs), 4.66 (1H, s), 4.53-4.49 (1H, m), 4.46-4.30 (3H, m), 3.76-3.70 (1H, m), 3.63 (1H, s), 3.62 (1H, s), 3.58 (3H, s), 3.48-3.33 (2H, m),3.27 (1H, s), 3.14 (1H, s), 2.86-2.81 (3H, m), 2.65-2.30 (2H, m), 2.18 (1.5H, s), 2.17-2.08 (1H, m), 2.00 (1.5H, s), 1.99-1.91 (4H, m), 1.76-1.72 (2H, m), 1.68-1.54 (1H, m), 1.52-1.38 (3H, m), 1.30-1.02 (2H, m), 0.93 (3H, t).

MS:ESI 656 (M+1)

Example 70

Methyl 2-(4-((N-(3-(4-amino-2-(2-methoxyethyl)-1H-imidazo[4,5-c]quinolin-1-yl)propyl)-2-(4-methylpiperazin-1-yl)acetamido)methyl)phenyl)acetate

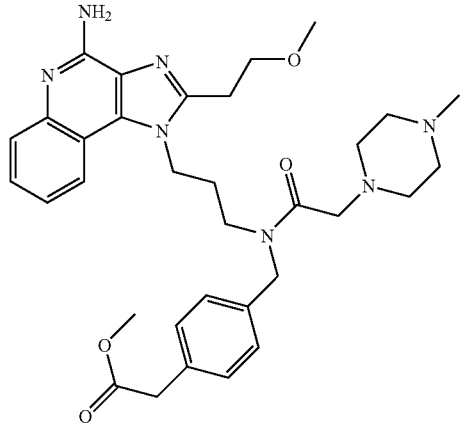 [SMILES: COCCc1nc2c(N)nc3ccccc3c2n1CCCN(Cc1ccc(CC(=O)OC)cc1)C(=O)CN1CCN(C)CC1]

The title compound was prepared by the method of example 29 step (vi) using N-methylpiperazine (193 mg) and the product of example 29 step (v) (207 mg). The title compound was obtained as a white solid. 51 mgs $^1$H NMR (DMSO-d6) δ 8.03-7.91 (m, 1H), 7.63-7.60 (m, 1H), 7.45-7.41 (m, 1H), 7.26-7.07 (m, 5H), 6.45 (brs, 2H), 4.68-4.46 (m, 4H), 3.83-3.78 (m, 2H), 3.64-3.63 (m, 2H), 3.60 (s, 3H), 3.51-3.39 (m, 2H), 3.31-3.27 (m, 5H), 3.15-3.01 (m, 4H), 2.42-1.92 (m, 11H).

MS: MULTIMODE+: 602

Example 71

Methyl 2-(4-((N-(3-(4-amino-2-(2-methoxyethyl)-1H-imidazo[4,5-c]quinolin-1-yl)propyl)-2-(4-(2-methoxyethyl)piperazin-1-yl)acetamido)methyl)phenyl)acetate

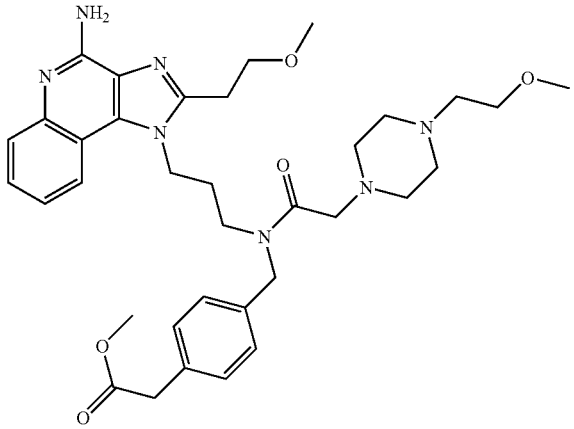 [SMILES: COCCc1nc2c(N)nc3ccccc3c2n1CCCN(Cc1ccc(CC(=O)OC)cc1)C(=O)CN1CCN(CCOC)CC1]

The title compound was prepared by the method of example 29 step (vi) using 1-(2-methoxyethyl)piperazine (241 mg) and the product of example 29 step (v) (180 mg). The title compound was obtained as a colourless solid. 14 mgs $^1$H NMR (DMSO-d6) δ 8.02-7.94 (m, 1H), 7.62 (d, 1H), 7.45-7.41 (m, 1H), 7.29-7.14 (m, 4H), 7.09 (d, 1H), 6.46 (s, 2H), 4.71-4.34 (m, 4H), 3.86-3.75 (m, 2H), 3.65-3.62 (m, 2H), 3.61-3.58 (m, 3H), 3.53-3.38 (m, 2H), 3.38-3.25 (m, 8H), 3.21-3.18 (m, 3H), 3.17-3.09 (m, 3H), 2.43-2.17 (m, 8H), 2.16-1.90 (m, 2H)

MS: MULTIMODE+: 646

Example 72

Methyl 2-(3-((N-(3-(4-amino-2-(2-methoxyethyl)-1H-imidazo[4,5-c]quinolin-1-yl)propyl)-2-(4-methylpiperazin-1-yl)acetamido)methyl)phenyl)acetate

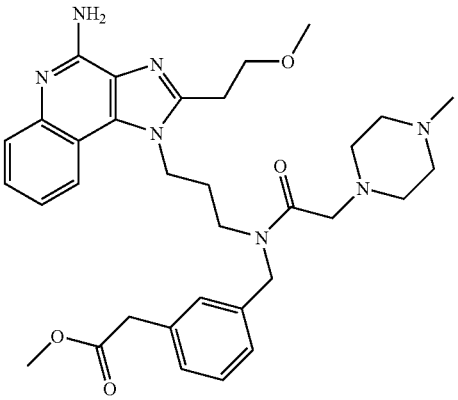 [SMILES: COCCc1nc2c(N)nc3ccccc3c2n1CCCN(Cc1cccc(CC(=O)OC)c1)C(=O)CN1CCN(C)CC1]

The title compound was prepared by the method of example 29 step (vi) using N-methylpiperazine (125 mg) and the product of example 31 step (i) (115 mg). The title compound was obtained as a gum. 26 mgs $^1$H NMR (DMSO-d6) δ 8.03-7.92 (m, 1H), 7.63-7.61 (m, 1H), 7.45-7.41 (m, 1H), 7.27-7.23 (m, 1H), 7.21-7.12 (m, 1H), 7.03 (m, 1H), 6.45 (brs, 2H), 4.68-4.48 (m, 4H), 3.83-3.77 (m, 2H), 3.64-3.60 (m, 2H), 3.59-3.57 (m, 3H), 3.56-3.39 (m, 2H), 3.31-3.27 (m, 5H), 3.16-3.00 (m, 4H), 2.42-1.94 (m, 11H).

MS: MULTIMODE+: 602

Example 73

Methyl 2-(3-((N-(3-(4-amino-2-(2-methoxyethyl)-1H-imidazo[4,5-c]quinolin-1-yl)propyl)-2-(4-(2-methoxyethyl)piperazin-1-yl)acetamido)methyl)phenyl)acetate

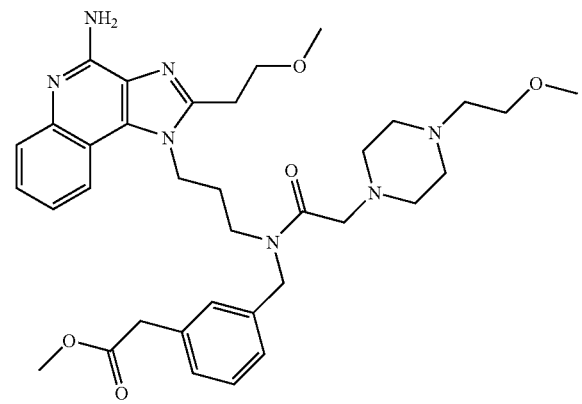 [SMILES: COCCc1nc2c(N)nc3ccccc3c2n1CCCN(Cc1cccc(CC(=O)OC)c1)C(=O)CN1CCN(CCOC)CC1]

The title compound was prepared by the method of example 29 step (vi) using 1-(2-methoxyethyl)piperazine (180 mg) and the product of example 31 step (i) (115 mg). The title compound was obtained as a gum. 34 mgs ¹H NMR (DMSO-d6) δ 8.02-7.92 (m, 1H), 7.62-7.60 (m, 1H), 7.45-7.41 (m, 1H), 7.27-7.21 (m, 1H), 7.15-7.11 (m, 1H), 7.03 (m, 1H), 6.45 (brs, 2H), 4.70-4.41 (m, 4H), 3.83-3.77 (m, 2H), 3.64-3.59 (m, 5H), 3.56-3.39 (m, 2H), 3.31-3.98 (m, 9H), 2.41-1.92 (m, 10H).
MS: MULTIMODE+: 646

Example 74

Methyl 2-(4-((N-(3-(4-amino-2-butyl-1H-imidazo[4,5-c]quinolin-1-yl)propyl)-2-(dimethylamino)acetamido)methyl)phenyl)acetate, Dimethane Sulfonic Acid Salt Methane sulfonic acid (0.048 mL, 0.73 mmol) was added to a solution of the product from example 3 (0.2 g) in MeCN (10 mL). The suspension was stirred for 3 hours and the solvent was evaporated. The resulting solid was suspended in MeCN (2 mL) and stirred for 7 days. The mixture was filtered using a centrifuge, dried at rt and a XRPD was run confirming that Polymorph A was formed.

Example 75

Methyl 2-(4-((N-(3-(4-amino-2-butyl-1H-imidazo[4,5-c]quinolin-1-yl)propyl)-2-(dimethylamino)acetamido)methyl)phenyl)acetat, Monosaccharin Salt Saccharin (53 mg) in MeOH (1 mL) was added to a solution of the product from example 3 (160 mg) in MeOH (1 mL) and stirred at rt for 1 hr and the solvent removed. The resulting residue was dissolved in THF (1 mL) and MeCN (1 mL) was added and stirred for 9 days. The solid was filtered off using a centrifuge, dried and a XRPD was run (see FIG. 1A). The same polymorph was also formed when slurried in water, MeCN and MeOH.
DSC: 167° C.±2° C.

Example 76

Figure 2B:
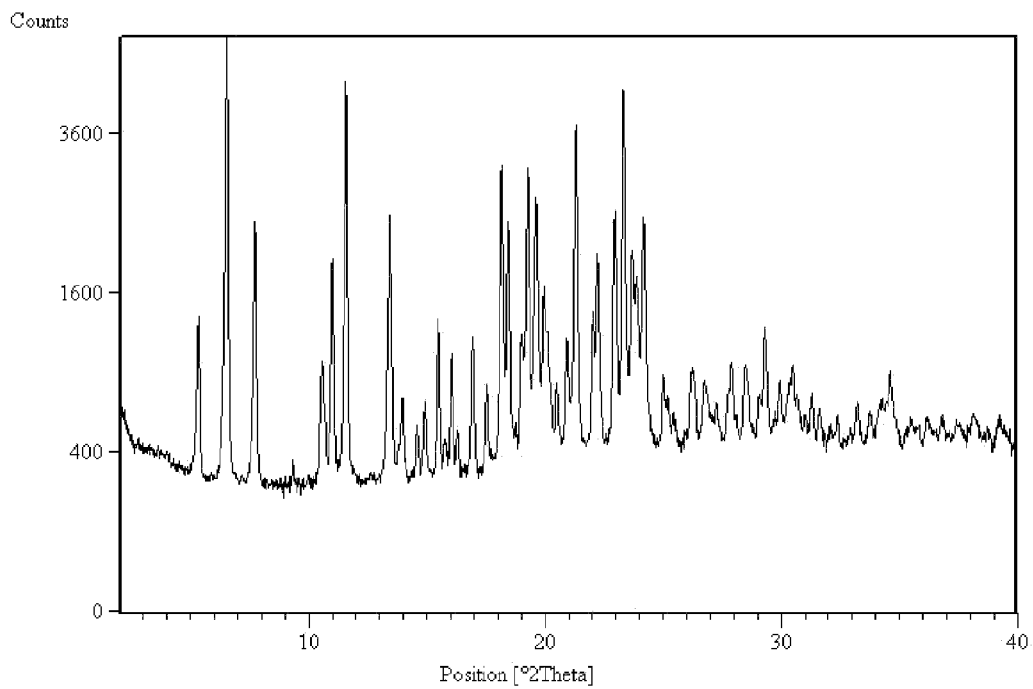

Methyl 2-(4-((N-(3-(4-amino-2-butyl-1H-imidazo[4,5-c]quinolin-1-yl)propyl)-2-(dimethylamino)acetamido)methyl)phenyl)acetate, Disaccharin Salt Saccharin (106 mg) in MeOH (1 mL) was added to a solution of the product of example 3 (160 mg) in methanol (1 mL). The resulting residue was dissolved in THF (2 mL) and stirred for 9 days. The solid was filtered off using a centrifuge, dried and a XRPD was run (see FIG. 2A). The same polymorph was also formed when slurried in dioxane, 1:1 EtOAc: ether, MeCN, 1:1 EtOAc:MeCN and 1:1 THF:MeCN.
DSC: 200° C.±2° C.

Example 77

Figure 3B:
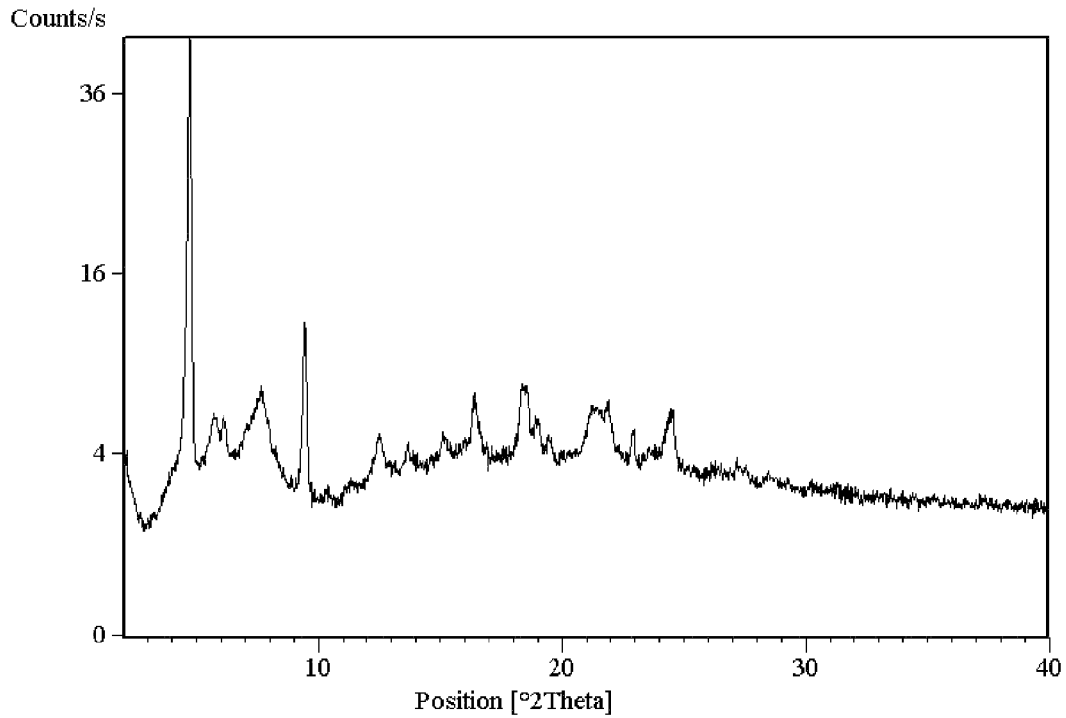
Figure 3D:
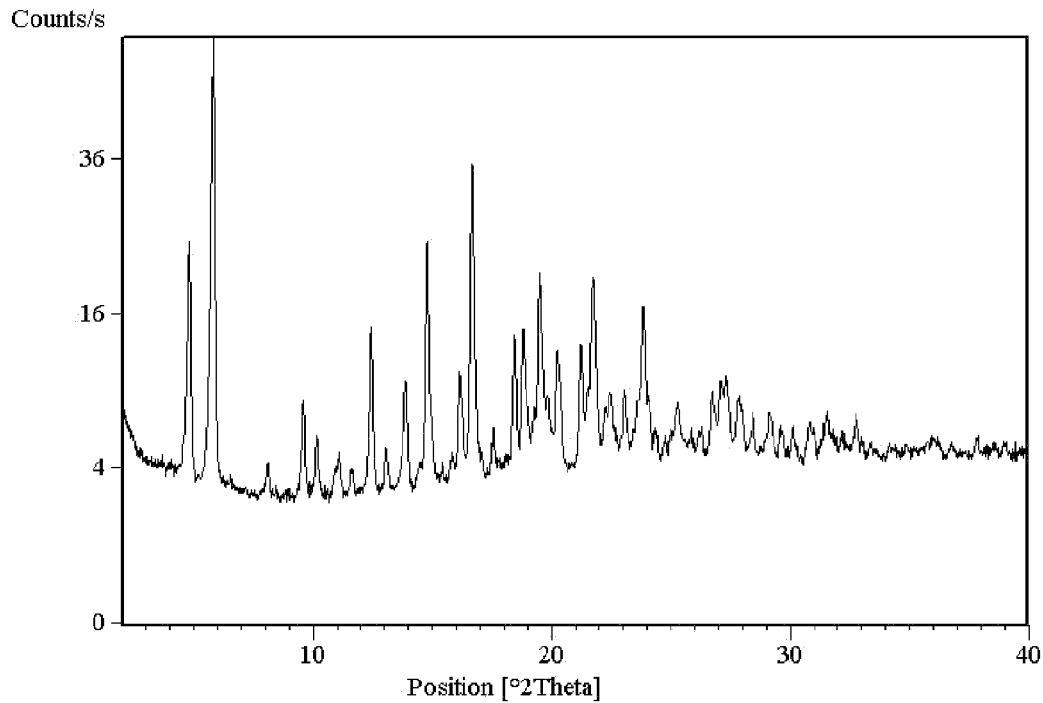

Methyl 2-(4-((N-(3-(4-amino-2-butyl-1H-imidazo[4,5-c]quinolin-1-yl)propyl)-2-(dimethylamino)acetamido)methyl)phenyl)acetate, di 1-hydroxy-2-naphthoic Acid Salt 1-hydroxy-2-naphthoic acid (138 mg,) in MeOH (5 mL) was added to the product from example 3 (200 mg) in MeOH (10 mL) and the solution was stirred for 2 h at rt. The solvents were evaporated, EtOAc (6 mL) was added and the mixture was stirred for 40 h at rt. The solid was filtered and dried and a XRPD was run (see FIG. 3A). The same polymorph (A) was also formed when slurried in MeOH and EtOH. A second polymorph (B) was formed with slurring in acetone, DCM, water and isohexane (see FIG. 3C). DSC (Polymorph A): Undergoes a phase transition at 120° C.±5° C. (onset). The resulting phase C melts at 153° C.±2° C. (onset).
DSC (Polymorph B): Melt onset 152° C.±2° C.

Example 78

Figure 4B:
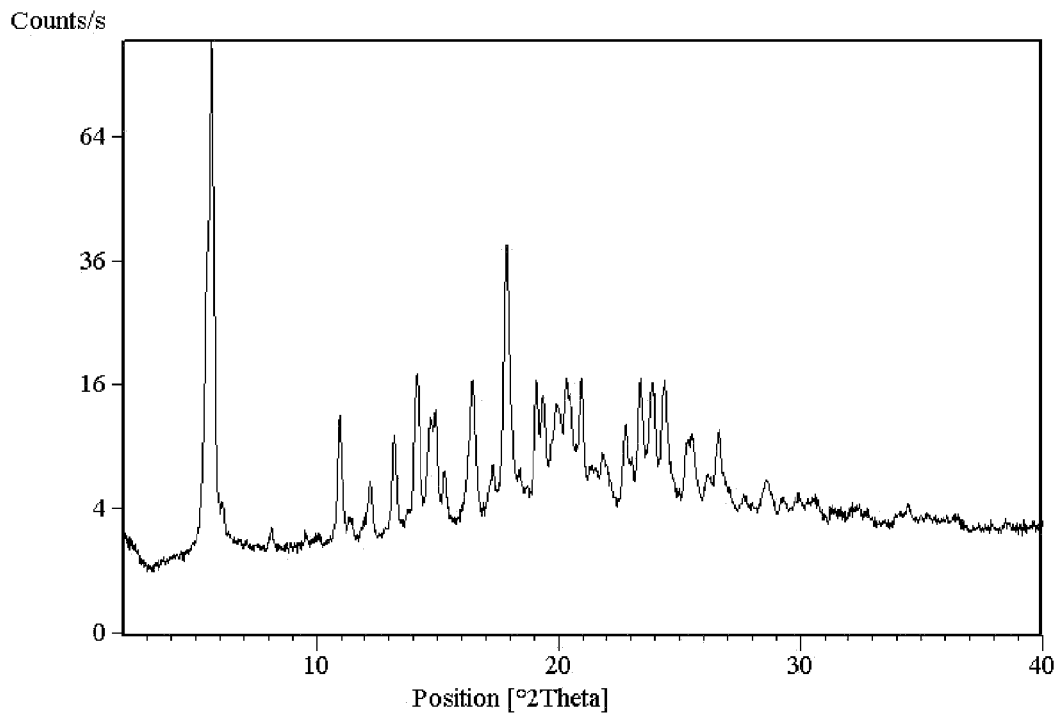

Methyl 2-(4-((N-(3-(4-amino-2-butyl-1H-imidazo[4,5-c]quinolin-1-yl)propyl)-2-(dimethylamino)acetamido)methyl)phenyl)acetate, Dibenzenesulfonic Acid Salt Benzenesulfonic acid (116 mg) in MeCN (5 mL) was added to the product from example 3 (200 mg) in MeCN (10 mL). The solvent was evaporated and EtOAc (12 mL) was added and the resulting solution was stirred for 5 days at room temperature. The solid was filtered dried and a XRPD was run (see FIG. 4A).

Example 79

Figure 5B:
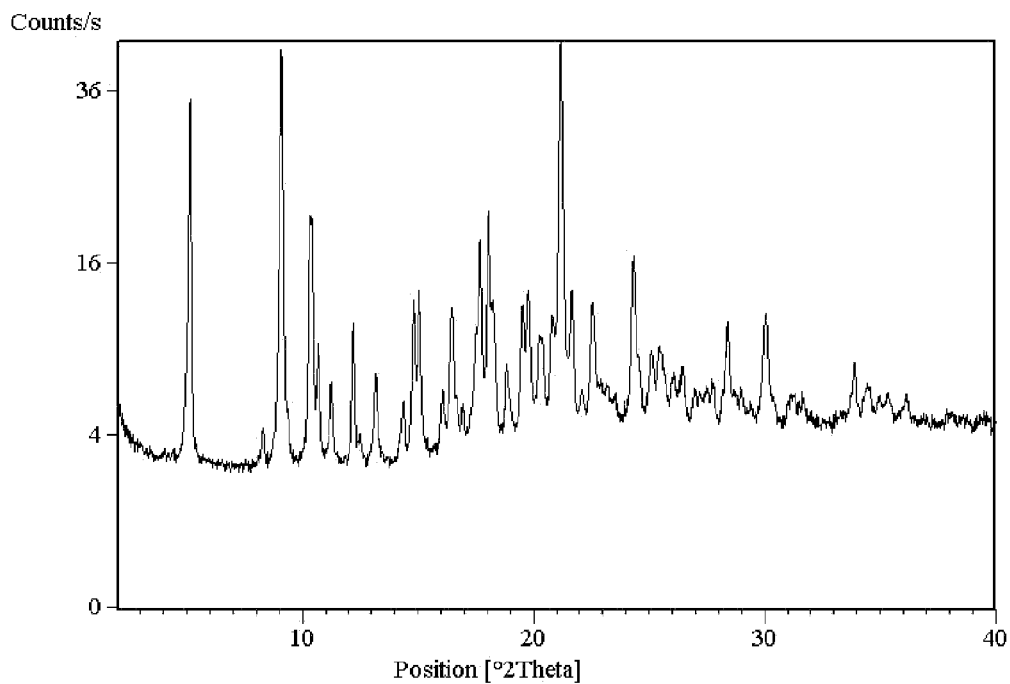

Methyl 2-(4-((N-(3-(4-amino-2-butyl-1H-imidazo[4,5-c]quinolin-1-yl)propyl)-2-(dimethylamino)acetamido)methyl)phenyl)acetate, Mandelic Acid Salt Mandelic acid (56 mg) was added to the product from example 3 (200 mg,) in MeCN (5 mL). The solvent was evaporated and the resulting gum was slurried in diethyl ether for 4 days. The solid was filtered, dried and a XRPD was run (see FIG. 5A).
DSC: Melt onset 104° C.±2° C.

Example 80

Figure 6B:
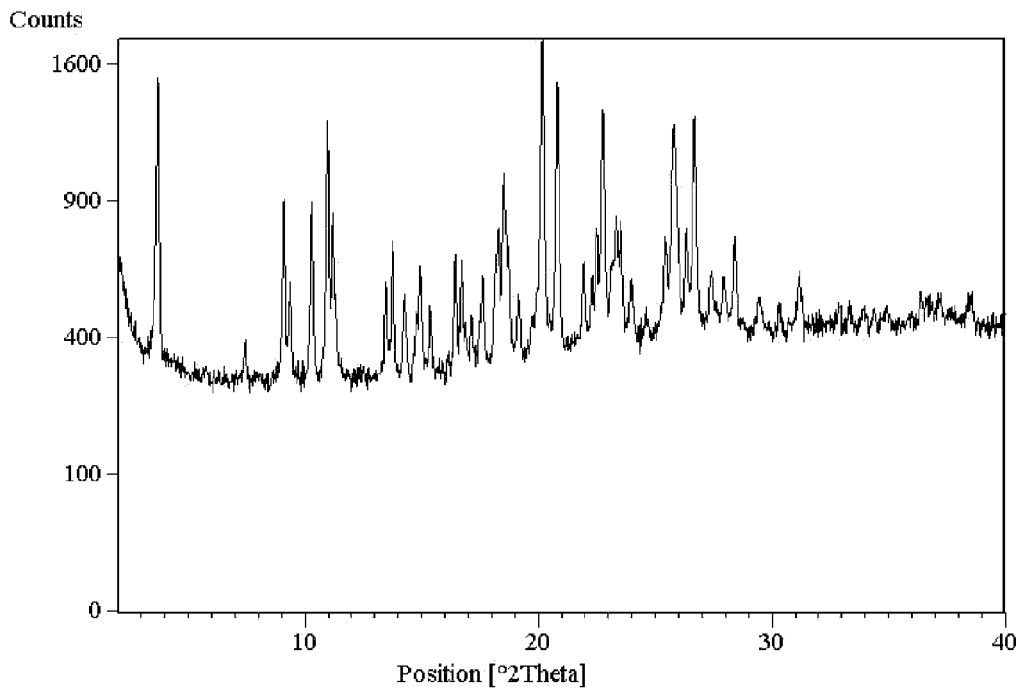

Methyl 2-(4-((N-(3-(4-amino-2-butyl-1H-imidazo[4,5-c]quinolin-1-yl)propyl)-2-(dimethylamino)acetamido)methyl)phenyl)acetate, Fumaric Acid Salt Fumaric acid (85 mg) dissolved in MeOH (10 mL) was added to the product of example 3 in MeOH (10 mL) and stirred for 20 mins. The solvent was removed and the resulting gum was stirred in a mixture of EtOAc (5 mL) and THF (5 mL) for 10 days, then filtered and a XRPD was run (see FIG. 6A).
DSC: Melt onset 175° C.±2° C.

Example 81

Figure 7B:
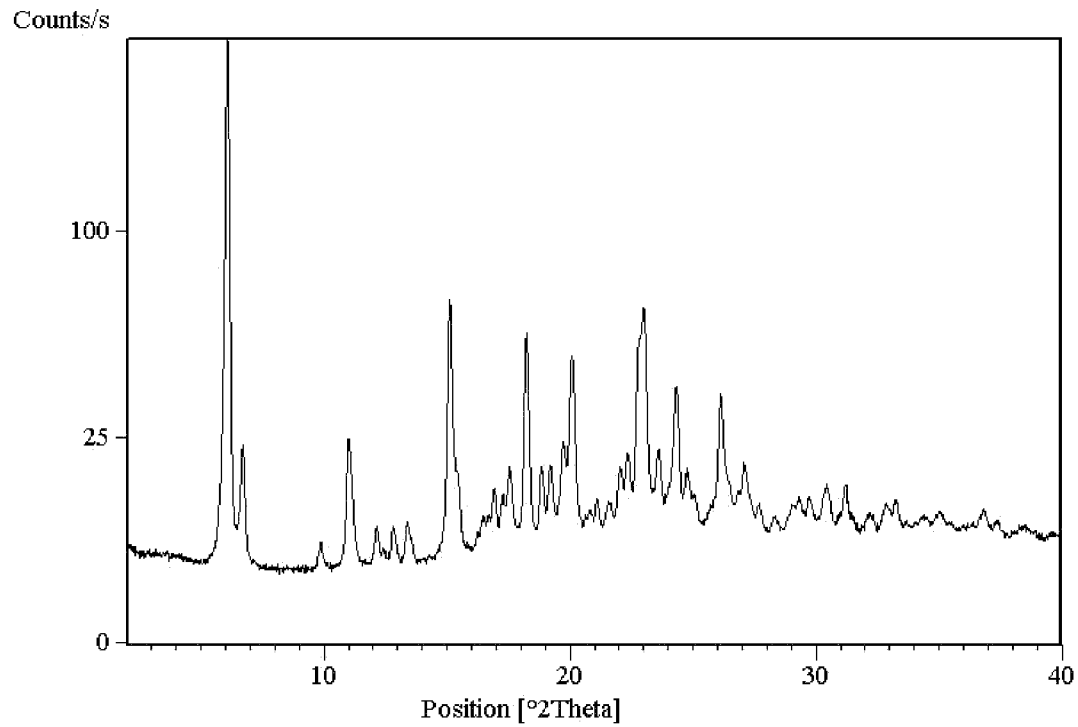
Figure 7D:
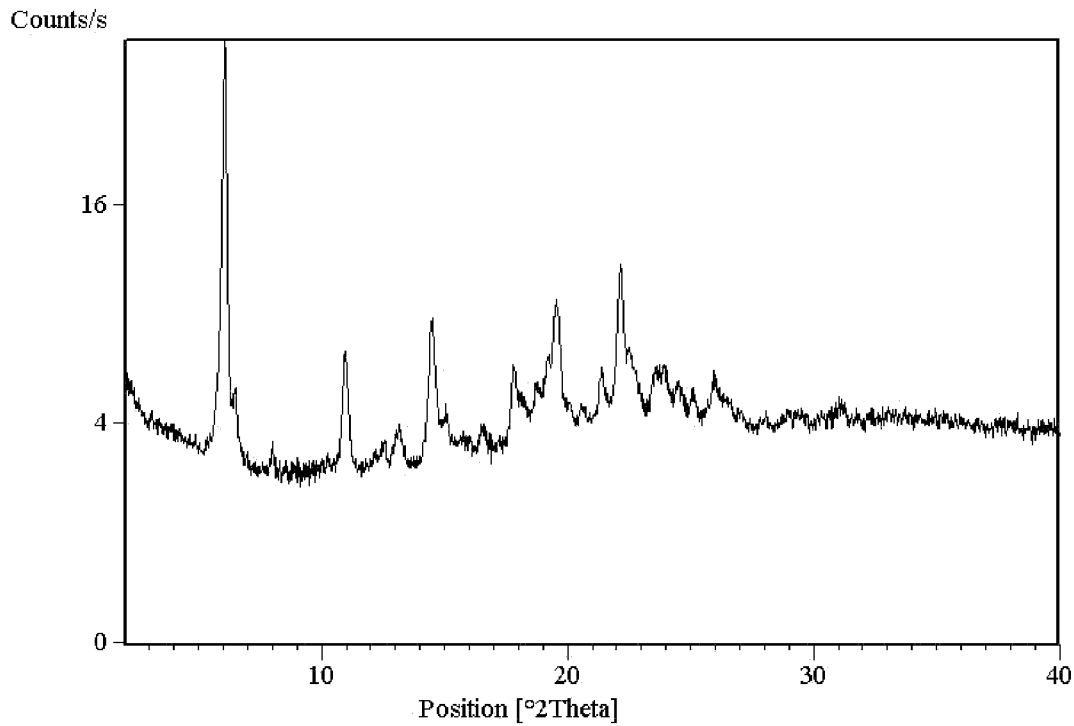

Methyl 2-(4-((N-(3-(4-amino-2-butyl-1H-imidazo[4,5-c]quinolin-1-yl)propyl)-2-(dimethylamino)acetamido)methyl)phenyl)acetate, Dimethane Sulfonic Acid Salt Methane sulfonic acid (0.024 mL) was added to the product from example 3 (0.2 g) in acetonitrile (10 mL). The mixture was stirred for 3 hours, the solid filtered, dried and a XRPD was run to give polymorph A (see FIG. 7A). Slurrying this solid in EtOAc (10 mL) for 2 days at rt gave polymorph B (see FIG. 7C).
DSC (Polymorph A): Melt onset 218° C.±2° C.
Biological Assay
Human TLR7 Assay The most common variant sequence of human TLR7 (represented by the EMBL sequence AF240467) was cloned into the mammalian cell expression vector pUNO and transfected into a HEK293 cell line already stably expressing the pNiFty2-SEAP reporter plasmid; integration of the reporter gene was maintained by selection with the antibiotic zeocin. Transfectants with stable TLR7 expression were selected using the antibiotic blasticidin. In this reporter cell-line, expression of secreted alkaline phosphatase (SEAP) is controlled by an NFkB/ELAM-1 composite promoter comprising five NFkB sites combined with the proximal ELAM-1 promoter. TLR signaling leads to the translocation of NFkB and activation of the promoter results in expression of the SEAP gene. TLR7-specific activation was assessed by determining the level of SEAP produced following overnight incubation of the cells at 37° C. with the standard compound in the presence of 0.1% (v/v) dimethylsulfoxide (DMSO). Concentration dependent induction of SEAP production by compounds was expressed as the concentration of compound which produced half of the maximal level of SEAP induction for that compound ($pEC_{50}$).

| Example no | $pEC_{50}$ | Example no. | $pEC_{50}$ |
|---|---|---|---|
| 1 | 6.5 | 2 | 6.4 |
| 3 | 7.1 | 4 | 7.4 |
| 5 | 6.5 | 6 | 6.6 |
| 7 | 6.4 | 8 | 6.5 |
| 9 | 6.2 | 10 | 6.3 |
| 11 | 6.6 | 12 | 6.6 |
| 13 | 6.8 | 14 | 6.6 |
| 15 | 6.4 | 16 | 6.9 |
| 17 | 6.8 | 18 | 7.2 |
| 19 | 6.6 | 20 | 6.6 |
| 21 | 6.2 | 22 | 6.2 |
| 23 | 6.6 | 24 | 7.1 |
| 25 | 6.7 | 26 | 6.5 |
| 27 | 7.4 | 28 | 6.7 |
| 29 | 7.0 | 30 | 6.7 |
| 31 | 6.8 | 32 | 6.8 |
| 33 | 6.8 | 34 | 6.5 |
| 35 | 6.7 | 36 | 6.7 |
| 37 | 6.4 | 38 | 5.8 |
| 39 | 6.8 | 40 | 6.9 |
| 41 | 7.1 | 42 | 5.8 |
| 43 | 6.9 | 44 | 6.6 |
| 45 | 5.8 | 46 | 7.2 |
| 47 | 6.4 | 48 | 6.4 |
| 49 | 7.1 | 50 | 6.3 |
| 51 | 6.7 | 52 | 6.2 |
| 53 | 6.1 | 54 | 6.0 |
| 55 | 7.1 | 56 | 6.3 |
| 57 | 7.3 | 58 | 5.9 |
| 59 | 6.1 | 60 | 7.1 |
| 61 | 6.4 | 62 | 6.6 |
| 63 | 6.3 | 64 | 5.9 |
| 65 | 6.2 | 66 | 6.8 |
| 67 | 6.3 | 68 | 6.3 |
| 69 | 6.4 | 70 | 6.4 |
| 71 | 6.7 | 72 | 6.3 |
| 73 | 6.3 | | |

Effect of the Compound of Example 3 on Antigen-induced Pulmonary Inflammation in a Rat Asthma Model Rats were sensitised and challenged to produce allergic airway inflammation in a similar manner to that described by Underwood et al (British Journal of Pharmacology 2002; 137: 263-275, 2002). Male Brown Norway rats were sensitized subcutaneously with ovalbumin (OVA) and aluminum hydroxide on day 0, and challenged with aerosolized OVA solution on day 14. The compound of Example 3 was administered twice intratracheally 24 hours before and 24 hours after the OVA-challenge and bronchoalveolar lavage fluid (BALF) was collected 48 hours after the OVA-challenge. Then eosinophiles and Th2 cytokines (IL-5 and IL-13) in the BALF were measured to evaluate efficacy of the compound of Example 3. The results obtained are shown in the following table.

| Eosinophiles and Th2 cytokines in BALF | | | | |
|---|---|---|---|---|
| Group (n = 8) | Dose (mg/kg) | Eosinophiles (cells/BALF) | IL-5 (pg/ml BALF) | IL-13 (pg/ml BALF) |
| Normal control | — | 7.5 ± 3.5 | 3.8 ± 3.8 | <4.9 |
| OVA-challenge contr | — | 476.7 ± 142.8 | 418.9 ± 151.0 | 103.2 ± 50.5 |
| Example 3 | 0.1 | 67.2 ± 16.3 | 18.0 ± 8.7 | <4.9 |
| Example 3 | 1 | 36.2 ± 11.3 | 11.3 ± 7.5 | <4.9 |

Mean ± SE (n = 8)

The invention claimed is:
1. A compound of formula (I)

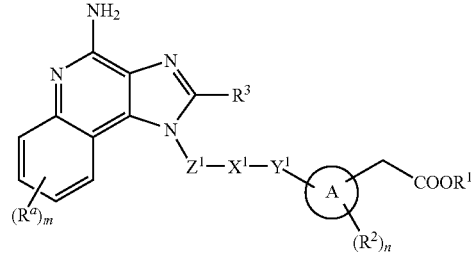

(I)

wherein
$R^1$ represents a straight chain $C_1$-$C_6$ alkyl, optionally substituted by one or more substituents independently selected from halogen, cyano, hydroxyl and $C_1$-$C_3$ alkoxy;
$Z^1$ represents a $C_2$-$C_6$ alkylene group;
$X^1$ represents $NR^5$ or >N—$COR^5$;
$Y^1$ represents $C_1$-$C_6$ alkylene;
each $R^2$ is independently selected from halogen, cyano, hydroxy, thiol, $C_1$-$C_3$ alkyl, $C_1$-$C_3$ hydroxyalkyl, $C_1$-$C_3$ haloalkyl, $C_1$-$C_3$ alkoxy, $C_1$-$C_3$ haloalkoxy, $C_{1-3}$alkylthio, $C_{1-3}$alkylsulfonyl and $C_{1-3}$alkylsulfinyl;
$R^3$ represents $C_{1-6}$alkyl optionally substituted by $C_{1-6}$alkoxy;
each $R^a$ is independently selected from halogen, cyano, hydroxy, thiol, $C_1$-$C_3$ alkyl, $C_1$-$C_3$ hydroxyalkyl, $C_1$-$C_3$ haloalkyl, $C_1$-$C_3$ alkoxy, $C_1$-$C_3$ haloalkoxy, $C_{1-3}$alkylthio, $C_{1-3}$alkylsulfonyl and $C_{1-3}$alkylsulfinyl;
$R^5$ represents hydrogen, a 3- to 8-membered saturated heterocyclic ring comprising a ring group O, $S(O)_p$ or $NR^{10}$, a $C_1$-$C_6$ alkyl group or $C_3$-$C_6$ cycloalkyl group, the latter two groups being optionally substituted by one or more substituents independently selected from $NR^7R^8$ or $R^9$,
or $R^5$ is a $C_1$-$C_6$ alkylene which may be linked to a carbon atom within a $C_2$-$C_6$alkylene group $Z^1$ so as to form a saturated 4-7 membered nitrogen containing ring;
$R^7$ and $R^8$ each independently represent hydrogen, a 3- to 8-membered saturated heterocyclic ring comprising a ring group O, $S(O)_p$ or $NR^{10a}$, $C_1$-$C_6$ alkyl or $C_3$-$C_6$ cycloalkyl, the latter two groups being optionally substituted by one or more groups independently selected from halogen, cyano, $S(O)_qR^{11}$, $OR^{12}$, $CO_2R^{12}$, $OC(O)R^{12}$, $SO_2NR^{12}R^{13}$, $CONR^{12}R^{13}$, $NR^{12}R^{13}$, $NR^{12}SO_2R^{14}$, $NR^{12}COR^{13}$, or a 3- to 8-membered saturated heterocyclic ring comprising a ring group O, $S(O)_p$ or $NR^{10b}$, or R⁷ and R⁸ together with the nitrogen atom to which they are attached form a 3- to 8-membered saturated heterocyclic ring comprising a ring nitrogen atom and optionally one or more further heteroatoms independently selected from nitrogen, oxygen, sulphur and sulphonyl, the heterocyclic ring being optionally substituted by one or more substituents independently selected from halogen, cyano, $S(O)_qR^{15}$, $OR^{15}$, $CO_2R^{15}$, $COR^{15}$, $OC(O)R^{15}$, $SO_2NR^{15}R^{16}$, $CONR^{15}R^{16}$, $NR^{15}R^{16}$, $NR^{15}SO_2R^{17}$, $NR^{15}COR^{16}$, $NR^{15}CO_2R^{16}$, heteroaryl, $C_1$-$C_6$ haloalkyl, $C_3$-$C_8$ cycloalkyl and $C_1$-$C_6$ alkyl, the latter two groups being optionally substituted by one or more groups independently selected from cyano, $S(O)_qR^{18}$, $OR^{18}$, $CO_2R^{18}$, $SO_2NR^{18}R^{19}$, $CONR^{18}R^{19}$ or $NR^{18}R^{19}$;

$R^9$ represents halogen, cyano, $CO_2R^{20}$, $S(O)_qR^{20}$, $OR^{20}$, $SO_2NR^{20}R^{22}$, $CONR^{20}R^{22}$, $NR^{20}SO_2R^{21}$, $NR^{20}CO_2R^{21}$, $NR^{20}COR^{22}$ or a 3- to 8-membered saturated heterocyclic ring comprising a ring group $NR^{10c}$;

$R^{10}$, $R^{10a}$, $R^{10b}$ and $R^{10c}$ independently represent hydrogen, $CO_2R^{23}$, $S(O)_qR^{23}$, $COR^{24}$, or a $C_1$-$C_6$ alkyl, $C_2$-$C_6$ alkenyl, $C_2$-$C_6$ alkynyl or $C_3$-$C_8$ cycloalkyl group, each of which may be optionally substituted by one or more substituents independently selected from halogen, cyano, $OR^{25}$ or $NR^{25}R^{26}$;

$R^{11}$, $R^{12}$, $R^{13}$, $R^{15}$, $R^{16}$, $R^{18}$, $R^{19}$, $R^{20}$, $R^{22}$, $R^{24}$, $R^{25}$ and $R^{26}$ each independently represent hydrogen, $C_1$-$C_6$ alkyl or $C_3$-$C_6$ cycloalkyl;

$R^{14}$, $R^{17}$, $R^{21}$ and $R^{23}$ each independently represent $C_1$-$C_6$ alkyl or $C_3$-$C_6$ cycloalkyl;

m, n, p and q each independently represent an integer 0, 1 or 2; and

A represents a monocyclic or bicyclic $C_6$-$C_{10}$ aryl; or a pharmaceutically acceptable salt thereof.

2. A compound according to claim 1 wherein $R^1$ is methyl or a pharmaceutically acceptable salt thereof.

3. A compound according to claim 1 wherein $Z^1$ is n-propylene or a pharmaceutically acceptable salt thereof.

4. A compound according to claim 1 wherein $X^1$ is a group $NR^5$ or a pharmaceutically acceptable salt thereof.

5. A compound according to claim 4 wherein $X^1$ is >$NCOR^5$ or a pharmaceutically acceptable salt thereof.

6. A compound according to claim 4 wherein $R^5$ is hydrogen or a $C_1$-$C_6$ alkyl or a pharmaceutically acceptable salt thereof optionally substituted by one or more groups $NR^7R^8$ or $R^9$.

7. A compound according to claim 4 wherein $R^5$ is a $C_1$-$C_6$ alkylene or a pharmaceutically acceptable salt thereof which may be linked to a carbon atom within a $C_2$-$C_6$ alkylene group $Z^1$ so as to form a saturated 4-7 membered nitrogen containing ring.

8. A compound according to claim 1 wherein A is phenyl or a pharmaceutically acceptable salt thereof.

9. A compound according to claim 1 where n is 0 or a pharmaceutically acceptable salt thereof.

10. A compound according to claim 1 where $R^3$ is n-butyl, methoxyethyl or ethoxymethyl or a pharmaceutically acceptable salt thereof.

11. A compound according to claim 1 where m is 0 or a pharmaceutically acceptable salt thereof.

12. A compound according to claim 1 selected from:
Methyl 2-(4-((3-(4-amino-2-butyl-1H-imidazo[4,5-c]quinolin-1-yl)propylamino)methyl)phenyl)acetate,
Methyl 2-(3-((3-(4-amino-2-butyl-1H-imidazo[4,5-c]quinolin-1-yl)propylamino)methyl)phenyl)acetate,
Methyl 2-(4-((N-(3-(4-amino-2-butyl-1H-imidazo[4,5-c]quinolin-1-yl)propyl)-2-(dimethylamino)acetamido)methyl)phenyl)acetate,
Methyl 2-(3-((N-(3-(4-amino-2-butyl-1H-imidazo[4,5-c]quinolin-1-yl)propyl)-2-(dimethylamino)acetamido)methyl)phenyl)acetate,
Methyl 2-(3-((4-((4-amino-2-(2-methoxyethyl)-1H-imidazo[4,5-c]quinolin-1-yl)methyl)piperidin-1-yl)methyl)phenyl)acetate di-trifluoroacetate salt,
Methyl [4-({[3-(4-amino-2-butyl-1H-imidazo[4,5-c]quinolin-1-yl)propyl][2-(dimethylamino)ethyl]amino}methyl)phenyl]acetate,
Methyl 2-(3-((N-(3-(4-amino-2-(ethoxymethyl)-1H-imidazo[4,5-c]quinolin-1-yl)propyl)-2-(dimethylamino)acetamido)methyl)phenyl)acetate,
Methyl 2-(3-(((3-(4-amino-2-butyl-1H-imidazo[4,5-c]quinolin-1-yl)propyl)(1-methylpiperidin-4-yl)amino)methyl)phenyl)acetate,
Methyl 2-(4-(((3-(4-amino-2-butyl-1H-imidazo[4,5-c]quinolin-1-yl)propyl)(1-methylpiperidin-4-yl)amino)methyl)phenyl)acetate,
Methyl 2-(4-((N-(3-(4-amino-2-butyl-1H-imidazo[4,5-c]quinolin-1-yl)propyl)-2-(4-methylpiperazin-1-yl)acetamido)methyl)phenyl)acetate,
Methyl 2-(3-(((3-(4-amino-2-butyl-1H-imidazo[4,5-c]quinolin-1-yl)propyl)(3-(dimethylamino)propyl)amino)methyl)phenyl)acetate,
Methyl 2-(3-(((3-(4-amino-2-butyl-1H-imidazo[4,5-c]quinolin-1-yl)propyl)(3-morpholinopropyl)amino)methyl)phenyl)acetate,
Methyl 2-(3-(((3-(4-amino-2-butyl-1H-imidazo[4,5-c]quinolin-1-yl)propyl)(3-(ethyl(methyl)amino)propyl)amino)methyl)phenyl)acetate,
Methyl 2-(3-(((3-(4-amino-2-butyl-1H-imidazo[4,5-c]quinolin-1-yl)propyl)(3-(4-methylpiperazin-1-yl)propyl)amino)methyl)phenyl)acetate,
Methyl 2-(4-((N-(3-(4-amino-2-butyl-1H-imidazo[4,5-c]quinolin-1-yl)propyl)-2-(methylsulfonyl)acetamido)methyl)phenyl)acetate,
Methyl 2-(4-((N-(3-(4-amino-2-butyl-1H-imidazo[4,5-c]quinolin-1-yl)propyl)acetamido)methyl)phenyl)acetate,
Methyl 2-(4-((N-(3-(4-amino-2-butyl-1H-imidazo[4,5-c]quinolin-1-yl)propyl)-2-morpholinoacetamido)methyl)phenyl)acetate,
Methyl 2-(4-((N-(3-(4-amino-2-butyl-1H-imidazo[4,5-c]quinolin-1-yl)propyl)-2-((2-methoxyethyl)(methyl)amino)acetamido)methyl)phenyl)acetate,
Methyl 2-(4-((2-(4-acetylpiperazin-1-yl)-N-(3-(4-amino-2-butyl-1H-imidazo[4,5-c]quinolin-1-yl)propyl)acetamido)methyl)phenyl)acetate,
(R)-Methyl 2-(4-((N-(3-(4-amino-2-butyl-1H-imidazo[4,5-c]quinolin-1-yl)propyl)-2-(3-hydroxypyrrolidin-1-yl)acetamido)methyl)phenyl)acetate,
Methyl 2-(4-((N-(3-(4-amino-2-butyl-1H-imidazo[4,5-c]quinolin-1-yl)propyl)-2-(4-(pyrimidin-2-yl)piperazin-1-yl)acetamido)methyl)phenyl)acetate,
Ethyl 4-(2-((3-(4-amino-2-butyl-1H-imidazo[4,5-c]quinolin-1-yl)propyl)(4-(2-methoxy-2-oxoethyl)benzyl)amino)-2-oxoethyl)piperazine-1-carboxylate,
Methyl 2-(4-((N-(3-(4-amino-2-butyl-1H-imidazo[4,5-c]quinolin-1-yl)propyl)-2-(4-(ethylsulfonyl)piperazin-1-yl)acetamido)methyl)phenyl)acetate,
Methyl 2-(4-((N-(3-(4-amino-2-butyl-1H-imidazo[4,5-c]quinolin-1-yl)propyl)-2-(piperidin-1-yl)acetamido)methyl)phenyl)acetate, Methyl 2-(4-((N-(3-(4-amino-2-butyl-1H-imidazo[4,5-c]quinolin-1-yl)propyl)-2-(4-(tert-butoxycarbonylamino)piperidin-1-yl)acetamido)methyl)phenyl)acetate, Methyl 2-(4-((N-(3-(4-amino-2-butyl-1H-imidazo[4,5-c]quinolin-1-yl)propyl)-2-(4-(tert-butoxycarbonyl(methyl)amino)piperidin-1-yl)acetamido)methyl)phenyl)acetate, Ethyl 2-(1-(2-((3-(4-amino-2-butyl-1H-imidazo[4,5-c]quinolin-1-yl)propyl)(4-(2-methoxy-2-oxoethyl)benzyl)amino)-2-oxoethyl)piperidin-4-yl)acetate, Methyl 1-(2-((3-(4-amino-2-butyl-1H-imidazo[4,5-c]quinolin-1-yl)propyl)(4-(2-methoxy-2-oxoethyl)benzyl)amino)-2-oxoethyl)piperidine-4-carboxylate, Methyl 2-(4-((N-(3-(4-amino-2-(2-methoxyethyl)-1H-imidazo[4,5-c]quinolin-1-yl)propyl)-2-(piperidin-1-yl)acetamido)methyl)phenyl)acetate, Methyl 2-(4-((N-(3-(4-amino-2-(2-methoxyethyl)-1H-imidazo[4,5-c]quinolin-1-yl)propyl)-2-(dimethylamino)acetamido)methyl)phenyl)acetate, Methyl 2-(3-((N-(3-(4-amino-2-(2-methoxyethyl)-1H-imidazo[4,5-c]quinolin-1-yl)propyl)-2-(piperidin-1-yl)acetamido)methyl)phenyl)acetate saccharin salt, Methyl 2-(4-((N-(3-(4-amino-2-(2-methoxyethyl)-1H-imidazo[4,5-c]quinolin-1-yl)propyl)-2-((2-methoxyethyl)(methyl)amino)acetamido)methyl)phenyl)acetate, Methyl 2-(4-((N-(3-(4-amino-2-(2-methoxyethyl)-1H-imidazo[4,5-c]quinolin-1-yl)propyl)-3-(piperidin-1-yl)propanamido)methyl)phenyl)acetate, Methyl 2-(4-(((3-(4-amino-2-(2-methoxyethyl)-1H-imidazo[4,5-c]quinolin-1-yl)propyl)(3-morpholinopropyl)amino)methyl)phenyl)acetate, (S)-Methyl 2-(4-((N-(3-(4-amino-2-(2-methoxyethyl)-1H-imidazo[4,5-c]quinolin-1-yl)propyl)-2-(2-(methoxymethyl)pyrrolidin-1-yl)acetamido)methyl)phenyl)acetate disaccharin salt, (R)-Methyl 2-(4-((N-(3-(4-amino-2-(2-methoxyethyl)-1H-imidazo[4,5-c]quinolin-1-yl)propyl)-2-(2-(methoxymethyl)pyrrolidin-1-yl)acetamido)methyl)phenyl)acetate disaccharin salt, Methyl 2-(4-((N-(3-(4-amino-2-(2-methoxyethyl)-1H-imidazo[4,5-c]quinolin-1-yl)propyl)-2-(pyrrolidin-1-yl)acetamido)methyl)phenyl)acetate disaccharin salt, Methyl 2-(4-((N-(3-(4-amino-2-(2-methoxyethyl)-1H-imidazo[4,5-c]quinolin-1-yl)propyl)-2-((2-hydroxyethyl)(methyl)amino)acetamido)methyl)phenyl)acetate disaccharin salt, Methyl 2-(3-((N-(3-(4-amino-2-butyl-1H-imidazo[4,5-c]quinolin-1-yl)propyl)-2-((2-methoxyethyl)(methyl)amino)acetamido)methyl)phenyl)acetate, Methyl 2-(3-((N-(3-(4-amino-2-butyl-1H-imidazo[4,5-c]quinolin-1-yl)propyl)-2-(butyl(methyl)amino)acetamido)methyl)phenyl)acetate, Methyl 3-((N-(3-(4-amino-2-butyl-1H-imidazo[4,5-c]quinolin-1-yl)propyl)-2-(dipropylamino)acetamido)methyl)phenyl)acetate, Methyl 2-(3-((N-(3-(4-amino-2-butyl-1H-imidazo[4,5-c]quinolin-1-yl)propyl)-2-(bis(2-hydroxyethyl)amino)acetamido)methyl)phenyl)acetate, Methyl 2-(3-((N-(3-(4-amino-2-butyl-1H-imidazo[4,5-c]quinolin-1-yl)propyl)-2-(methyl(tetrahydro-2H-pyran-4-yl)amino)acetamido)methyl)phenyl)acetate, Methyl 2-(3-((N-(3-(4-amino-2-butyl-1H-imidazo[4,5-c]quinolin-1-yl)propyl)-2-(azetidin-1-yl)acetamido)methyl)phenyl)acetate, Methyl 2-(3-((N-(3-(4-amino-2-butyl-1H-imidazo[4,5-c]quinolin-1-yl)propyl)-2-(3-hydroxyazetidin-1-yl)acetamido)methyl)phenyl)acetate, Methyl 2-(3-((N-(3-(4-amino-2-butyl-1H-imidazo[4,5-c]quinolin-1-yl)propyl)-2-(pyrrolidin-1-yl)acetamido)methyl)phenyl)acetate, Methyl 2-(3-((N-(3-(4-amino-2-butyl-1H-imidazo[4,5-c]quinolin-1-yl)propyl)-2-(3-hydroxypyrrolidin-1-yl)acetamido)methyl)phenyl)acetate, (R)-Methyl 2-(3-((N-(3-(4-amino-2-butyl-1H-imidazo[4,5-c]quinolin-1-yl)propyl)-2-(3-hydroxypyrrolidin-1-yl)acetamido)methyl)phenyl)acetate, Methyl 2-(3-((N-(3-(4-amino-2-butyl-1H-imidazo[4,5-c]quinolin-1-yl)propyl)-2-(piperidin-1-yl)acetamido)methyl)phenyl)acetate, Methyl 2-(3-((N-(3-(4-amino-2-butyl-1H-imidazo[4,5-c]quinolin-1-yl)propyl)-2-(4-hydroxypiperidin-1-yl)acetamido)methyl)phenyl)acetate, Methyl 2-(3-((N-(3-(4-amino-2-butyl-1H-imidazo[4,5-c]quinolin-1-yl)propyl)-2-(4-methoxypiperidin-1-yl)acetamido)methyl)phenyl)acetate, Methyl 2-(3-((N-(3-(4-amino-2-butyl-1H-imidazo[4,5-c]quinolin-1-yl)propyl)-2-(4-(dimethylcarbamoyl)piperidin-1-yl)acetamido)methyl)phenyl)acetate, Methyl 2-(3-((N-(3-(4-amino-2-butyl-1H-imidazo[4,5-c]quinolin-1-yl)propyl)-2-morpholinoacetamido)methyl)phenyl)acetate, Methyl 2-(3-((N-(3-(4-amino-2-butyl-1H-imidazo[4,5-c]quinolin-1-yl)propyl)-2-((2S,6R)-2,6-dimethylmorpholino)acetamido)methyl)phenyl)acetate, Methyl 2-(3-((N-(3-(4-amino-2-butyl-1H-imidazo[4,5-c]quinolin-1-yl)propyl)-2-(4-methylpiperazin-1-yl)acetamido)methyl)phenyl)acetate, Methyl 2-(3-((N-(3-(4-amino-2-butyl-1H-imidazo[4,5-c]quinolin-1-yl)propyl)-2-(4-(2-hydroxyethyl)piperazin-1-yl)acetamido)methyl)phenyl)acetate, Methyl 2-(3-((N-(3-(4-amino-2-butyl-1H-imidazo[4,5-c]quinolin-1-yl)propyl)-2-(4-(2-methoxyethyl)piperazin-1-yl)acetamido)methyl)phenyl)acetate, Methyl 2-(3-((2-(4-acetylpiperazin-1-yl)-N-(3-(4-amino-2-butyl-1H-imidazo[4,5-c]quinolin-1-yl)propyl)acetamido)methyl)phenyl)acetate, Methyl 2-(3-((N-(3-(4-amino-2-butyl-1H-imidazo[4,5-c]quinolin-1-yl)propyl)-2-(4-(methylsulfonyl)piperazin-1-yl)acetamido)methyl)phenyl)acetate, Methyl 2-(3-((N-(3-(4-amino-2-butyl-1H-imidazo[4,5-c]quinolin-1-yl)propyl)-2-(azepan-1-yl)acetamido)methyl)phenyl)acetate, Methyl 2-(3-((N-(3-(4-amino-2-butyl-1H-imidazo[4,5-c]quinolin-1-yl)propyl)-2-(1,4-oxazepan-4-yl)acetamido)methyl)phenyl)acetate, Methyl 2-(3-((N-(3-(4-amino-2-butyl-1H-imidazo[4,5-c]quinolin-1-yl)propyl)-2-(4-methyl-1,4-diazepan-1-yl)acetamido)methyl)phenyl)acetate, Methyl 2-(3-((2-(4-acetyl-1,4-diazepan-1-yl)-N-(3-(4-amino-2-butyl-1H-imidazo[4,5-c]quinolin-1-yl)propyl)acetamido)methyl)phenyl)acetate, Methyl 2-(3-((N-(3-(4-amino-2-butyl-1H-imidazo[4,5-c]quinolin-1-yl)propyl)-2-(4-(ethylcarbamoyl)-1,4-diazepan-1-yl)acetamido)methyl)phenyl)acetate, Methyl 2-(3-((N-(3-(4-amino-2-butyl-1H-imidazo[4,5-c]quinolin-1-yl)propyl)-2-(4-(methylsulfonyl)-1,4-diazepan-1-yl)acetamido)methyl)phenyl)acetate, Methyl 2-(4-((N-(3-(4-amino-2-butyl-1H-imidazo[4,5-c]quinolin-1-yl)propyl)-2-(4-(2-methoxyethyl)piperazin-1-yl)acetamido)methyl)phenyl)acetate, Methyl 2-(4-((2-(4-acetyl-1,4-diazepan-1-yl)-N-(3-(4-amino-2-butyl-1H-imidazo[4,5-c]quinolin-1-yl)propyl)acetamido)methyl)phenyl)acetate, Methyl 2-(4-((N-(3-(4-amino-2-butyl-1H-imidazo[4,5-c]quinolin-1-yl)propyl)-2-(4-(methylsulfonyl)-1,4-diazepan-1-yl)acetamido)methyl)phenyl)acetate, Methyl 2-(4-((2-((1-acetylpiperidin-4-yl)(methyl)amino)-N-(3-(4-amino-2-butyl-1H-imidazo[4,5-c]quinolin-1-yl)propyl)acetamido)methyl)phenyl)acetate, Methyl 2-(4-((N-(3-(4-amino-2-butyl-1H-imidazo[4,5-c]quinolin-1-yl)propyl)-2-(dimethylamino)acetamido)methyl)phenyl)acetate dimethane sulfonic acid salt, Methyl 2-(4-((N-(3-(4-amino-2-butyl-1H-imidazo[4,5-c]quinolin-1-yl)propyl)-2-(dimethylamino)acetamido)methyl)phenyl)acetat monosaccharin salt, Methyl 2-(4-((N-(3-(4-amino-2-butyl-1H-imidazo[4,5-c]quinolin-1-yl)propyl)-2-(dimethylamino)acetamido)methyl)phenyl)acetate disaccharin salt, Methyl 2-(4-((N-(3-(4-amino-2-butyl-1H-imidazo[4,5-c]quinolin-1-yl)propyl)-2-(dimethylamino)acetamido)methyl)phenyl)acetate di-1-hydroxy-2-naphthoic acid salt, Methyl 2-(4-((N-(3-(4-amino-2-butyl-1H-imidazo[4,5-c]quinolin-1-yl)propyl)-2-(dimethylamino)acetamido)methyl)phenyl)acetate dibenzenesulfonic acid salt, Methyl 2-(4-((N-(3-(4-amino-2-butyl-1H-imidazo[4,5-c]quinolin-1-yl)propyl)-2-(dimethylamino)acetamido)methyl)phenyl)acetate mandelic acid salt, Methyl 2-(4-((N-(3-(4-amino-2-butyl-1H-imidazo[4,5-c]quinolin-1-yl)propyl)-2-(dimethylamino)acetamido)methyl)phenyl)acetate fumaric acid salt, Methyl 2-(4-((N-(3-(4-amino-2-(2-methoxyethyl)-1H-imidazo[4,5-c]quinolin-1-yl)propyl)-2-(4-methylpiperazin-1-yl)acetamido)methyl)phenyl)acetate, Methyl 2-(4-((N-(3-(4-amino-2-(2-methoxyethyl)-1H-imidazo[4,5-c]quinolin-1-yl)propyl)-2-(4-(2-methoxyethyl)piperazin-1-yl)acetamido)methyl)phenyl)acetate, Methyl 2-(3-((N-(3-(4-amino-2-(2-methoxyethyl)-1H-imidazo[4,5-c]quinolin-1-yl)propyl)-2-(4-methylpiperazin-1-yl)acetamido)methyl)phenyl)acetate, and Methyl 2-(3-((N-(3-(4-amino-2-(2-methoxyethyl)-1H-imidazo[4,5-c]quinolin-1-yl)propyl)-2-(4-(2-methoxyethyl)piperazin-1-yl)acetamido)methyl)phenyl)acetate.

13. A pharmaceutical composition comprising a compound of formula (I) or a pharmaceutically acceptable salt thereof as claimed in claim 1 in association with a pharmaceutically acceptable adjuvant, diluent or carrier.

14. A compound according to claim 1 selected from:

Methyl 2-(4-((3-(4-amino-2-butyl-1H-imidazo[4,5-c]quinolin-1-yl)propylamino)methyl)phenyl)acetate, Methyl 2-(3-((3-(4-amino-2-butyl-1H-imidazo[4,5-c]quinolin-1-yl)propylamino)methyl)phenyl)acetate, Methyl 2-(4-((N-(3-(4-amino-2-butyl-1H-imidazo[4,5-c]quinolin-1-yl)propyl)-2-(dimethylamino)acetamido)methyl)phenyl)acetate, Methyl 2-(3-((N-(3-(4-amino-2-butyl-1H-imidazo[4,5-c]quinolin-1-yl)propyl)-2-(dimethylamino)acetamido)methyl)phenyl)acetate, Methyl 2-(3-((4-((4-amino-2-(2-methoxyethyl)-1H-imidazo[4,5-c]quinolin-1-yl)methyl)piperidin-1-yl)methyl)phenyl)acetate di-trifluoroacetate salt, Methyl [4-({[3-(4-amino-2-butyl-1H-imidazo[4,5-c]quinolin-1-yl)propyl][2-(dimethylamino)ethyl]amino}methyl)phenyl]acetate, Methyl 2-(3-((N-(3-(4-amino-2-(ethoxymethyl)-1H-imidazo[4,5-c]quinolin-1-yl)propyl)-2-(dimethylamino)acetamido)methyl)phenyl)acetate, Methyl 2-(3-(((3-(4-amino-2-butyl-1H-imidazo[4,5-c]quinolin-1-yl)propyl)(1-methylpiperidin-4-yl)amino)methyl)phenyl)acetate, Methyl 2-(4-(((3-(4-amino-2-butyl-1H-imidazo[4,5-c]quinolin-1-yl)propyl)(1-methylpiperidin-4-yl)amino)methyl)phenyl)acetate, Methyl 2-(4-((N-(3-(4-amino-2-butyl-1H-imidazo[4,5-c]quinolin-1-yl)propyl)-2-(4-methylpiperazin-1-yl)acetamido)methyl)phenyl)acetate, Methyl 2-(3-(((3-(4-amino-2-butyl-1H-imidazo[4,5-c]quinolin-1-yl)propyl)(3-(dimethylamino)propyl)amino)methyl)phenyl)acetate, Methyl 2-(3-(((3-(4-amino-2-butyl-1H-imidazo[4,5-c]quinolin-1-yl)propyl)(3-morpholinopropyl)amino)methyl)phenyl)acetate, Methyl 2-(3-(((3-(4-amino-2-butyl-1H-imidazo[4,5-c]quinolin-1-yl)propyl)(3-(ethyl(methyl)amino)propyl)amino)methyl)phenyl)acetate, Methyl 2-(3-(((3-(4-amino-2-butyl-1H-imidazo[4,5-c]quinolin-1-yl)propyl)(3-(4-methylpiperazin-1-yl)propyl)amino)methyl)phenyl)acetate, Methyl 2-(4-((N-(3-(4-amino-2-butyl-1H-imidazo[4,5-c]quinolin-1-yl)propyl)-2-(methylsulfonyl)acetamido)methyl)phenyl)acetate, Methyl 2-(4-((N-(3-(4-amino-2-butyl-1H-imidazo[4,5-c]quinolin-1-yl)propyl)acetamido)methyl)phenyl)acetate, Methyl 2-(4-((N-(3-(4-amino-2-butyl-1H-imidazo[4,5-c]quinolin-1-yl)propyl)-2-morpholinoacetamido)methyl)phenyl)acetate, Methyl 2-(4-((N-(3-(4-amino-2-butyl-1H-imidazo[4,5-c]quinolin-1-yl)propyl)-2-((2-methoxyethyl)(methyl)amino)acetamido)methyl)phenyl)acetate, Methyl 2-(4-((2-(4-acetylpiperazin-1-yl)-N-(3-(4-amino-2-butyl-1H-imidazo[4,5-c]quinolin-1-yl)propyl)acetamido)methyl)phenyl)acetate, (R)-Methyl 2-(4-((N-(3-(4-amino-2-butyl-1H-imidazo[4,5-c]quinolin-1-yl)propyl)-2-(3-hydroxypyrrolidin-1-yl)acetamido)methyl)phenyl)acetate, Methyl 2-(4-((N-(3-(4-amino-2-butyl-1H-imidazo[4,5-c]quinolin-1-yl)propyl)-2-(4-(pyrimidin-2-yl)piperazin-1-yl)acetamido)methyl)phenyl)acetate, Ethyl 4-(2-((3-(4-amino-2-butyl-1H-imidazo[4,5-c]quinolin-1-yl)propyl)(4-(2-methoxy-2-oxoethyl)benzyl)amino)-2-oxoethyl)piperazine-1-carboxylate, Methyl 2-(4-((N-(3-(4-amino-2-butyl-1H-imidazo[4,5-c]quinolin-1-yl)propyl)-2-(4-(ethylsulfonyl)piperazin-1-yl)acetamido)methyl)phenyl)acetate, Methyl 2-(4-((N-(3-(4-amino-2-butyl-1H-imidazo[4,5-c]quinolin-1-yl)propyl)-2-(piperidin-1-yl)acetamido)methyl)phenyl)acetate, Methyl 2-(4-((N-(3-(4-amino-2-butyl-1H-imidazo[4,5-c]quinolin-1-yl)propyl)-2-(4-(tert-butoxycarbonylamino)piperidin-1-yl)acetamido)methyl)phenyl)acetate, Methyl 2-(4-((N-(3-(4-amino-2-butyl-1H-imidazo[4,5-c]quinolin-1-yl)propyl)-2-(4-(tert-butoxycarbonyl(methyl)amino)piperidin-1-yl)acetamido)methyl)phenyl)acetate, Ethyl 2-(1-(2-((3-(4-amino-2-butyl-1H-imidazo[4,5-c]quinolin-1-yl)propyl)(4-(2-methoxy-2-oxoethyl)benzyl)amino)-2-oxoethyl)piperidin-4-yl)acetate, Methyl 1-(2-((3-(4-amino-2-butyl-1H-imidazo[4,5-c]quinolin-1-yl)propyl)(4-(2-methoxy-2-oxoethyl)benzyl)amino)-2-oxoethyl)piperidine-4-carboxylate, Methyl 2-(4-((N-(3-(4-amino-2-(2-methoxyethyl)-1H-imidazo[4,5-c]quinolin-1-yl)propyl)-2-(piperidin-1-yl)acetamido)methyl)phenyl)acetate, Methyl 2-(4-((N-(3-(4-amino-2-(2-methoxyethyl)-1H-imidazo[4,5-c]quinolin-1-yl)propyl)-2-(dimethylamino)acetamido)methyl)phenyl)acetate, Methyl 2-(3-((N-(3-(4-amino-2-(2-methoxyethyl)-1H-imidazo[4,5-c]quinolin-1-yl)propyl)-2-(piperidin-1-yl)acetamido)methyl)phenyl)acetate, Methyl 2-(4-((N-(3-(4-amino-2-(2-methoxyethyl)-1H-imidazo[4,5-c]quinolin-1-yl)propyl)-2-((2-methoxyethyl)(methyl)amino)acetamido)methyl)phenyl)acetate, Methyl 2-(4-((N-(3-(4-amino-2-(2-methoxyethyl)-1H-imidazo[4,5-c]quinolin-1-yl)propyl)-3-(piperidin-1-yl)propanamido)methyl)phenyl)acetate, Methyl 2-(4-(((3-(4-amino-2-(2-methoxyethyl)-1H-imidazo[4,5-c]quinolin-1-yl)propyl)(3-morpholinopropyl)amino)methyl)phenyl)acetate, (S)-Methyl 2-(4-((N-(3-(4-amino-2-(2-methoxyethyl)-1H-imidazo[4,5-c]quinolin-1-yl)propyl)-2-(2-(methoxymethyl)pyrrolidin-1-yl)acetamido)methyl)phenyl)acetate, (R)-Methyl 2-(4-((N-(3-(4-amino-2-(2-methoxyethyl)-1H-imidazo[4,5-c]quinolin-1-yl)propyl)-2-(2-(methoxymethyl)pyrrolidin-1-yl)acetamido)methyl)phenyl)acetate, Methyl 2-(4-((N-(3-(4-amino-2-(2-methoxyethyl)-1H-imidazo[4,5-c]quinolin-1-yl)propyl)-2-(pyrrolidin-1-yl)acetamido)methyl)phenyl)acetate, Methyl 2-(4-((N-(3-(4-amino-2-(2-methoxyethyl)-1H-imidazo[4,5-c]quinolin-1-yl)propyl)-2-((2-hydroxyethyl)(methyl)amino)acetamido)methyl)phenyl)acetate, Methyl 2-(3-((N-(3-(4-amino-2-butyl-1H-imidazo[4,5-c]quinolin-1-yl)propyl)-2-((2-methoxyethyl)(methyl)amino)acetamido)methyl)phenyl)acetate, Methyl 2-(3-((N-(3-(4-amino-2-butyl-1H-imidazo[4,5-c]quinolin-1-yl)propyl)-2-(butyl(methyl)amino)acetamido)methyl)phenyl)acetate, Methyl 3-((N-(3-(4-amino-2-butyl-1H-imidazo[4,5-c]quinolin-1-yl)propyl)-2-(dipropylamino)acetamido)methyl)phenyl)acetate, Methyl 2-(3-((N-(3-(4-amino-2-butyl-1H-imidazo[4,5-c]quinolin-1-yl)propyl)-2-(bis(2-hydroxyethyl)amino)acetamido)methyl)phenyl)acetate, Methyl 2-(3-((N-(3-(4-amino-2-butyl-1H-imidazo[4,5-c]quinolin-1-yl)propyl)-2-(methyl(tetrahydro-2H-pyran-4-yl)amino)acetamido)methyl)phenyl)acetate, Methyl 2-(3-((N-(3-(4-amino-2-butyl-1H-imidazo[4,5-c]quinolin-1-yl)propyl)-2-(azetidin-1-yl)acetamido)methyl)phenyl)acetate, Methyl 2-(3-((N-(3-(4-amino-2-butyl-1H-imidazo[4,5-c]quinolin-1-yl)propyl)-2-(3-hydroxyazetidin-1-yl)acetamido)methyl)phenyl)acetate, Methyl 2-(3-((N-(3-(4-amino-2-butyl-1H-imidazo[4,5-c]quinolin-1-yl)propyl)-2-(pyrrolidin-1-yl)acetamido)methyl)phenyl)acetate, Methyl 2-(3-((N-(3-(4-amino-2-butyl-1H-imidazo[4,5-c]quinolin-1-yl)propyl)-2-(3-hydroxypyrrolidin-1-yl)acetamido)methyl)phenyl)acetate, (R)-Methyl 2-(3-((N-(3-(4-amino-2-butyl-1H-imidazo[4,5-c]quinolin-1-yl)propyl)-2-(3-hydroxypyrrolidin-1-yl)acetamido)methyl)phenyl)acetate, Methyl 2-(3-((N-(3-(4-amino-2-butyl-1H-imidazo[4,5-c]quinolin-1-yl)propyl)-2-(piperidin-1-yl)acetamido)methyl)phenyl)acetate, Methyl 2-(3-((N-(3-(4-amino-2-butyl-1H-imidazo[4,5-c]quinolin-1-yl)propyl)-2-(4-hydroxypiperidin-1-yl)acetamido)methyl)phenyl)acetate, Methyl 2-(3-((N-(3-(4-amino-2-butyl-1H-imidazo[4,5-c]quinolin-1-yl)propyl)-2-(4-methoxypiperidin-1-yl)acetamido)methyl)phenyl)acetate, Methyl 2-(3-((N-(3-(4-amino-2-butyl-1H-imidazo[4,5-c]quinolin-1-yl)propyl)-2-(4-(dimethylcarbamoyl)piperidin-1-yl)acetamido)methyl)phenyl)acetate, Methyl 2-(3-((N-(3-(4-amino-2-butyl-1H-imidazo[4,5-c]quinolin-1-yl)propyl)-2-morpholinoacetamido)methyl)phenyl)acetate, Methyl 2-(3-((N-(3-(4-amino-2-butyl-1H-imidazo[4,5-c]quinolin-1-yl)propyl)-2-((2S,6R)-2,6-dimethylmorpholino)acetamido)methyl)phenyl)acetate, Methyl 2-(3-((N-(3-(4-amino-2-butyl-1H-imidazo[4,5-c]quinolin-1-yl)propyl)-2-(4-methylpiperazin-1-yl)acetamido)methyl)phenyl)acetate, Methyl 2-(3-((N-(3-(4-amino-2-butyl-1H-imidazo[4,5-c]quinolin-1-yl)propyl)-2-(4-(2-hydroxyethyl)piperazin-1-yl)acetamido)methyl)phenyl)acetate, Methyl 2-(3-((N-(3-(4-amino-2-butyl-1H-imidazo[4,5-c]quinolin-1-yl)propyl)-2-(4-(2-methoxyethyl)piperazin-1-yl)acetamido)methyl)phenyl)acetate, Methyl 2-(3-((2-(4-acetylpiperazin-1-yl)-N-(3-(4-amino-2-butyl-1H-imidazo[4,5-c]quinolin-1-yl)propyl)acetamido)methyl)phenyl)acetate, Methyl 2-(3-((N-(3-(4-amino-2-butyl-1H-imidazo[4,5-c]quinolin-1-yl)propyl)-2-(4-(methylsulfonyl)piperazin-1-yl)acetamido)methyl)phenyl)acetate, Methyl 2-(3-((N-(3-(4-amino-2-butyl-1H-imidazo[4,5-c]quinolin-1-yl)propyl)-2-(azepan-1-yl)acetamido)methyl)phenyl)acetate, Methyl 2-(3-((N-(3-(4-amino-2-butyl-1H-imidazo[4,5-c]quinolin-1-yl)propyl)-2-(1,4-oxazepan-4-yl)acetamido)methyl)phenyl)acetate, Methyl 2-(3-((N-(3-(4-amino-2-butyl-1H-imidazo[4,5-c]quinolin-1-yl)propyl)-2-(4-methyl-1,4-diazepan-1-yl)acetamido)methyl)phenyl)acetate, Methyl 2-(3-((2-(4-acetyl-1,4-diazepan-1-yl)-N-(3-(4-amino-2-butyl-1H-imidazo[4,5-c]quinolin-1-yl)propyl)acetamido)methyl)phenyl)acetate, Methyl 2-(3-((N-(3-(4-amino-2-butyl-1H-imidazo[4,5-c]quinolin-1-yl)propyl)-2-(4-(ethylcarbamoyl)-1,4-diazepan-1-yl)acetamido)methyl)phenyl)acetate, Methyl 2-(3-((N-(3-(4-amino-2-butyl-1H-imidazo[4,5-c]quinolin-1-yl)propyl)-2-(4-(methylsulfonyl)-1,4-diazepan-1-yl)acetamido)methyl)phenyl)acetate, Methyl 2-(4-((N-(3-(4-amino-2-butyl-1H-imidazo[4,5-c]quinolin-1-yl)propyl)-2-(4-(2-methoxyethyl)piperazin-1-yl)acetamido)methyl)phenyl)acetate, Methyl 2-(4-((2-(4-acetyl-1,4-diazepan-1-yl)-N-(3-(4-amino-2-butyl-1H-imidazo[4,5-c]quinolin-1-yl)propyl)acetamido)methyl)phenyl)acetate, Methyl 2-(4-((N-(3-(4-amino-2-butyl-1H-imidazo[4,5-c]quinolin-1-yl)propyl)-2-(4-(methylsulfonyl)-1,4-diazepan-1-yl)acetamido)methyl)phenyl)acetate, Methyl 2-(4-((2-((1-acetylpiperidin-4-yl)(methyl)amino)-N-(3-(4-amino-2-butyl-1H-imidazo[4,5-c]quinolin-1-yl)propyl)acetamido)methyl)phenyl)acetate, Methyl 2-(4-((N-(3-(4-amino-2-(2-methoxyethyl)-1H-imidazo[4,5-c]quinolin-1-yl)propyl)-2-(4-methylpiperazin-1-yl)acetamido)methyl)phenyl)acetate, Methyl 2-(4-((N-(3-(4-amino-2-(2-methoxyethyl)-1H-imidazo[4,5-c]quinolin-1-yl)propyl)-2-(4-(2-methoxyethyl)piperazin-1-yl)acetamido)methyl)phenyl)acetate, Methyl 2-(3-((N-(3-(4-amino-2-(2-methoxyethyl)-1H-imidazo[4,5-c]quinolin-1-yl)propyl)-2-(4-methylpiperazin-1-yl)acetamido)methyl)phenyl)acetate, and Methyl 2-(3-((N-(3-(4-amino-2-(2-methoxyethyl)-1H-imidazo[4,5-c]quinolin-1-yl)propyl)-2-(4-(2-methoxyethyl)piperazin-1-yl)acetamido)methyl)phenyl)acetate; or a pharmaceutically acceptable salt of any one thereof.

15. A compound according to claim 1 or a pharmaceutically acceptable salt thereof, wherein $Z^1$ is a $C_2$-$C_6$ alkylene group.

16. A compound according to claim 1 or a pharmaceutically acceptable salt thereof, wherein $Z^1$ is a straight chain $C_2$-$C_4$ alkylene group.

17. A compound according to claim 1 or a pharmaceutically acceptable salt thereof, wherein $R^5$ is $C_1$-$C_3$ alkyl optionally substituted by one or more groups $NR^7R^8$ where $R^7$ and $R^8$ are as defined in claim 1.

18. A compound according to claim 1 or a pharmaceutically acceptable salt thereof, wherein $Y^1$ represents $CH_2$.

19. A compound according to claim 1 or a pharmaceutically acceptable salt thereof, wherein $R^7$ and $R^8$ each independently represent tetrahydropyranyl, N-acetylpiperidinyl or $C_1$-$C_4$ alkyl optionally substituted by $OR^{12}$, wherein $R^{12}$ is as defined in claim 1.

20. A compound according to claim 1 or a pharmaceutically acceptable salt thereof, wherein:
  $R^1$ is methyl;
  $X^1$ is >$NCOR^5$;
  $R^3$ is n-butyl, methoxyethyl or ethoxymethyl;
  $Z^1$ is a straight chain $C_2$-$C_4$ alkylene group;
  $Y^1$ represents $CH_2$;
  $R^5$ is $C_1$-$C_3$ alkyl optionally substituted by one or more groups $NR^7R^8$;
  $R^7$ and $R^8$ each independently represent tetrahydropyranyl, N-acetylpiperidinyl or $C_1$-$C_4$ alkyl optionally substituted by $OR^{12}$, wherein $R^{12}$ is as defined in claim 1; and
  m and n are both 0.

21. A pharmaceutical composition comprising a compound according to claim 20 or a pharmaceutically acceptable salt thereof in association with a pharmaceutically acceptable adjuvant, diluent or carrier.

* * * * *

UNITED STATES PATENT AND TRADEMARK OFFICE
CERTIFICATE OF CORRECTION

PATENT NO. : 8,436,178 B2
APPLICATION NO. : 12/596817
DATED : May 7, 2013
INVENTOR(S) : Bonnert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 617 days.

Signed and Sealed this
Eighth Day of September, 2015

Michelle K. Lee
*Director of the United States Patent and Trademark Office*